(12) United States Patent
Severns et al.

(10) Patent No.: US 11,707,388 B2
(45) Date of Patent: Jul. 25, 2023

(54) METHOD OF MANUFACTURING RFID TAGS

(71) Applicant: Hill-Rom Services, Inc., Batesville, IN (US)

(72) Inventors: Ryan S. Severns, Grand Rapids, MI (US); James D. Voll, Columbus, IN (US); Brett A. Knittle, Oldenburg, IN (US); Gavin M. Monson, Oxford, OH (US); John V. Harmeyer, Cleves, OH (US); Charles A. Lachenbruch, Batesville, IN (US); Frank E. Sauser, Cincinnati, OH (US); Joseph T. Canter, Harrison, OH (US); Yongji Fu, Harrison, OH (US); Kirsten M. Emmons, Batesville, IN (US); David L. Ribble, Indianapolis, IN (US); Neal Wiggermann, Batesville, IN (US); John D. Christie, Batesville, IN (US); Dan R. Tallent, Hope, IN (US); Marwan Nusair, Cincinnati, OH (US); Edward J. Koors, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 17/865,479

(22) Filed: Jul. 15, 2022

(65) Prior Publication Data

US 2022/0362067 A1 Nov. 17, 2022

Related U.S. Application Data

(63) Continuation of application No. 17/242,352, filed on Apr. 28, 2021, now Pat. No. 11,478,383, which is a
(Continued)

(51) Int. Cl.
  *G06K 9/22* (2006.01)
  *A61F 13/42* (2006.01)
  (Continued)

(52) U.S. Cl.
  CPC ........ *A61F 13/42* (2013.01); *A61F 13/15203* (2013.01); *G06K 7/10158* (2013.01);
  (Continued)

(58) Field of Classification Search
  CPC ........... G06K 19/06046; G06K 19/067; G06K 19/07; H01L 2924/00; G07F 19/20
  (Continued)

(56) References Cited

U.S. PATENT DOCUMENTS

| 1,772,232 A | 8/1930 | Guilder |
| 2,127,538 A | 8/1938 | Seiger |

(Continued)

FOREIGN PATENT DOCUMENTS

| CA | 2361145 | 12/1999 |
| CA | 2494896 | 12/1999 |

(Continued)

OTHER PUBLICATIONS

Extended European Search Report for European Patent Application No. 18190478.0 dated Jan. 25, 2019 (6 pages).
(Continued)

*Primary Examiner* — Daniel St Cyr
(74) *Attorney, Agent, or Firm* — Barnes & Thornburg LLP

(57) ABSTRACT

An absorbent article has one or more fluid filter layers to inhibit electrode traces from being exposed to low volumes of fluid to reduce the number of false positives that are indicated by an RFID tag of the incontinence detection pad. An antenna inlay has a sacrificial trace portion to permit testing for proper operation of an RFID chip electrically
(Continued)

coupled to the antenna inlay. After testing, the sacrificial trace portion is severed. A fluid barrier layer blocks fluid from reaching portions of electrode traces that are located on a backsheet outside a periphery of an absorbent core of an incontinence detection pad. The power at which an antenna transmits to wirelessly energize a passive RFID tag of an incontinence detection pad is controlled to reduce the number of false positives indicated by the RFID tag.

20 Claims, 40 Drawing Sheets

Related U.S. Application Data continuation of application No. 16/889,903, filed on Jun. 2, 2020, now Pat. No. 11,020,284, which is a continuation of application No. 16/110,603, filed on Aug. 23, 2018, now Pat. No. 10,716,715.

(60) Provisional application No. 62/660,558, filed on Apr. 20, 2018, provisional application No. 62/648,543, filed on Mar. 27, 2018, provisional application No. 62/551,565, filed on Aug. 29, 2017.

(51) Int. Cl.
| | |
|---|---|
| *A61F 13/15* | (2006.01) |
| *H01Q 1/22* | (2006.01) |
| *G06K 7/10* | (2006.01) |
| *G06K 19/07* | (2006.01) |
| *H01Q 21/08* | (2006.01) |
| *G06K 19/077* | (2006.01) |

(52) U.S. Cl.
CPC ..... *G06K 7/10366* (2013.01); *G06K 19/0709* (2013.01); *G06K 19/07745* (2013.01); *H01Q 1/2216* (2013.01); *H01Q 21/08* (2013.01); *A61F 2013/424* (2013.01)

(58) Field of Classification Search
USPC .................................................. 235/492, 487
See application file for complete search history.

(56) References Cited

U.S. PATENT DOCUMENTS

| | | | |
|---|---|---|---|
| 2,644,050 A | 6/1953 | Seiger | |
| 2,668,202 A | 2/1954 | Kaplan | |
| 2,726,294 A | 12/1955 | Kroening et al. | |
| 2,907,841 A | 10/1959 | Campbell | |
| 3,199,095 A | 8/1965 | Ashida | |
| 3,971,371 A | 7/1976 | Bloom | |
| 4,069,817 A | 1/1978 | Fenote et al. | |
| 4,106,001 A | 8/1978 | Mahoney | |
| 4,163,449 A | 8/1979 | Regal | |
| 4,191,950 A | 3/1980 | Levin et al. | |
| 4,212,295 A | 7/1980 | Snyder | |
| 4,228,426 A | 10/1980 | Roberts | |
| 4,347,503 A | 8/1982 | Uyehara | |
| 4,539,559 A | 9/1985 | Kelley et al. | |
| 4,747,166 A | 5/1988 | Kuntz | |
| 4,965,554 A | 10/1990 | Darling | |
| 5,081,422 A | 1/1992 | Shih | |
| 5,086,294 A | 2/1992 | Schwab, Jr. | |
| 5,137,033 A | 8/1992 | Norton | |
| 5,144,284 A | 9/1992 | Hammett | |
| 5,291,181 A | 3/1994 | De Ponte | |
| 5,438,721 A | 8/1995 | Pahno et al. | |
| 5,459,452 A | 10/1995 | DePonte | |
| 5,491,609 A | 2/1996 | Dankman et al. | |
| 5,537,095 A | 7/1996 | Dick et al. | |
| 5,675,854 A | 10/1997 | Zibelin | |
| 5,760,694 A | 6/1998 | Nissim et al. | |
| 5,790,035 A | 8/1998 | Ho | |
| 5,824,883 A | 10/1998 | Park et al. | |
| 5,910,080 A | 6/1999 | Selton | |
| 5,947,943 A | 9/1999 | Lee | |
| 6,028,241 A | 2/2000 | Armstead | |
| 6,047,419 A | 4/2000 | Fergusaon | |
| 6,104,311 A | 8/2000 | Lastinger | |
| 6,292,102 B1 | 9/2001 | Smith | |
| 6,340,932 B1 | 1/2002 | Rodgers et al. | |
| 6,341,393 B1 | 1/2002 | Votel | |
| 6,351,215 B2 | 2/2002 | Rodgers et al. | |
| 6,362,737 B1 | 3/2002 | Rodgers et al. | |
| 6,384,728 B1 | 5/2002 | Kanor et al. | |
| 6,544,200 B1 | 4/2003 | Smith et al. | |
| 6,552,661 B1 | 4/2003 | Lastinger et al. | |
| 6,583,722 B2 | 6/2003 | Jeutter et al. | |
| 6,603,403 B2 | 8/2003 | Jeutter et al. | |
| 6,621,410 B1 | 9/2003 | Lastinger et al. | |
| 6,639,517 B1 | 10/2003 | Chapman et al. | |
| 6,774,800 B2 | 8/2004 | Friedman et al. | |
| 6,831,562 B2 | 12/2004 | Rodgers et al. | |
| 6,832,507 B1 | 12/2004 | van de Berg et al. | |
| 6,876,303 B2 | 4/2005 | Reeder et al. | |
| 6,914,562 B2 | 7/2005 | Forster | |
| 6,933,849 B2 | 8/2005 | Sawyer | |
| 6,948,205 B2 | 9/2005 | Van Der Wurf et al. | |
| 6,951,596 B2 * | 10/2005 | Green ............... | G06K 19/07718 156/264 |
| 6,982,646 B2 | 1/2006 | Rodgers et al. | |
| 7,017,213 B2 | 3/2006 | Chisari | |
| 7,030,731 B2 | 4/2006 | Lastinger et al. | |
| 7,055,754 B2 | 6/2006 | Forster | |
| 7,071,830 B2 | 7/2006 | Sahiberg et al. | |
| 7,120,952 B1 | 10/2006 | Bass et al. | |
| 7,135,973 B2 | 11/2006 | Kittel et al. | |
| 7,159,774 B2 | 1/2007 | Woodard et al. | |
| 7,170,415 B2 * | 1/2007 | Forster ............... | G06K 19/0739 340/572.9 |
| 7,172,113 B2 | 2/2007 | Olenick et al. | |
| 7,181,206 B2 | 2/2007 | Pedersen | |
| 7,250,547 B1 | 7/2007 | Hofmeister et al. | |
| 7,253,729 B2 | 8/2007 | Lastinger et al. | |
| 7,274,944 B2 | 9/2007 | Lastinger et al. | |
| 7,292,148 B2 | 11/2007 | Forster et al. | |
| 7,302,278 B2 | 11/2007 | Lastinger et al. | |
| 7,305,246 B2 | 12/2007 | Lastinger et al. | |
| 7,308,270 B2 | 12/2007 | Lastinger et al. | |
| 7,336,243 B2 | 2/2008 | Jo et al. | |
| 7,348,930 B2 | 3/2008 | Lastinger et al. | |
| 7,349,701 B2 | 3/2008 | Lastinger et al. | |
| 7,355,090 B2 | 4/2008 | Ales, III et al. | |
| 7,359,675 B2 | 4/2008 | Lastinger et al. | |
| 7,361,251 B2 | 4/2008 | Green et al. | |
| 7,368,032 B2 | 5/2008 | Green et al. | |
| 7,379,024 B2 * | 5/2008 | Forster ............. | G06K 19/07718 343/700 MS |
| 7,400,860 B2 | 7/2008 | Lastinger et al. | |
| 7,424,298 B2 | 9/2008 | Lastinger et al. | |
| 7,460,015 B2 | 12/2008 | Forster et al. | |
| 7,477,151 B2 | 1/2009 | Forster et al. | |
| 7,489,252 B2 | 2/2009 | Long et al. | |
| 7,489,282 B2 | 2/2009 | Lastinger et al. | |
| 7,498,478 B2 | 3/2009 | Long et al. | |
| 7,501,955 B2 | 3/2009 | Forster et al. | |
| 7,501,984 B2 | 3/2009 | Forster et al. | |
| 7,551,089 B2 | 6/2009 | Sawyer | |
| 7,586,385 B2 | 9/2009 | Rokhsaz | |
| 7,595,734 B2 | 9/2009 | Long et al. | |
| 7,595,756 B2 | 9/2009 | Lastinger et al. | |
| 7,598,853 B2 | 10/2009 | Becker et al. | |
| 7,598,862 B2 | 10/2009 | Lastinger et al. | |
| 7,599,699 B2 | 10/2009 | Lastinger et al. | |
| 7,616,959 B2 | 11/2009 | Spenik et al. | |
| 7,629,888 B2 | 12/2009 | Forster et al. | |
| 7,633,378 B2 | 12/2009 | Rodgers et al. | |
| 7,633,394 B2 | 12/2009 | Forster | |
| 7,649,125 B2 | 1/2010 | Ales, III et al. | |
| 7,652,636 B2 | 1/2010 | Forster et al. | |

(56) References Cited

U.S. PATENT DOCUMENTS

| | | |
|---|---|---|
| 7,663,483 B2 | 2/2010 | Spenik et al. |
| 7,667,600 B2 | 2/2010 | Woodbury et al. |
| 7,746,266 B2 | 6/2010 | Zoughi et al. |
| 7,782,212 B2 | 8/2010 | Burns et al. |
| 7,810,267 B2 * | 10/2010 | Saint ............ G09F 3/005 |
| | | 40/633 |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,855,648 B2 | 12/2010 | Vigneron et al. |
| 7,873,319 B2 | 1/2011 | Lastinger et al. |
| 7,922,094 B2 | 4/2011 | Banerjee et al. |
| 7,948,381 B2 | 5/2011 | Lindsay et al. |
| 7,977,529 B2 | 7/2011 | Bergman et al. |
| 7,911,345 B2 | 8/2011 | Yamamoto |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,199,016 B2 | 6/2012 | Forster et al. |
| 8,237,572 B2 | 8/2012 | Clement et al. |
| 8,246,773 B2 | 8/2012 | Green et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,099 B2 | 11/2012 | Potyrailo et al. |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,730,045 B2 | 5/2014 | Forster |
| 8,736,425 B2 | 5/2014 | Potyrailo |
| 8,742,929 B2 | 6/2014 | Sawyer |
| 8,749,319 B2 | 6/2014 | Rokhsaz et al. |
| 8,760,295 B2 | 6/2014 | Forster |
| 8,766,804 B2 | 7/2014 | Reeder et al. |
| 8,842,013 B2 | 9/2014 | Sawyer |
| 8,855,089 B2 | 10/2014 | Lastinger et al. |
| 8,866,615 B2 | 10/2014 | Sawyer |
| 8,872,663 B2 | 10/2014 | Forster |
| 8,874,186 B2 | 10/2014 | Forster |
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,915,583 B2 | 12/2014 | Edwards et al. |
| 8,933,292 B2 | 1/2015 | Abraham et al. |
| 8,946,499 B2 | 2/2015 | Iyer et al. |
| 8,947,236 B2 | 2/2015 | Forster |
| 8,957,277 B2 | 2/2015 | Carty et al. |
| 8,962,909 B2 | 2/2015 | Groosman et al. |
| 8,978,452 B2 | 3/2015 | Johnson et al. |
| 9,000,924 B2 | 4/2015 | Forster et al. |
| 9,048,819 B2 | 6/2015 | Rokhsaz et al. |
| 9,070,060 B2 | 6/2015 | Forster |
| 9,107,776 B2 | 8/2015 | Bergman et al. |
| 9,135,547 B2 * | 9/2015 | Forster ............ G06K 19/07318 |
| 9,160,054 B2 | 10/2015 | Yu et al. |
| 9,317,795 B2 | 4/2016 | Forster |
| 9,323,797 B2 | 4/2016 | Acree |
| 9,366,644 B1 | 6/2016 | Lastinger et al. |
| 9,495,632 B2 | 11/2016 | Green et al. |
| 9,506,886 B1 | 11/2016 | Woodbury et al. |
| 9,649,230 B1 | 5/2017 | Li |
| 9,658,167 B2 | 5/2017 | Forster et al. |
| 9,719,951 B1 | 8/2017 | Woodbury et al. |
| 10,159,607 B2 | 12/2018 | Monson et al. |
| 10,349,881 B1 | 7/2019 | Monson et al. |
| 10,716,715 B2 * | 7/2020 | Severns ............ G06K 7/10366 |
| 11,020,284 B2 * | 6/2021 | Severns ............ G06K 19/0709 |
| 2002/0011932 A1 | 1/2002 | Rodgers et al. |
| 2002/0033757 A1 | 3/2002 | Rodgers et al. |
| 2002/0145525 A1 | 10/2002 | Friedman et al. |
| 2002/0145526 A1 | 10/2002 | Friedman et al. |
| 2003/0019405 A1 | 1/2003 | Ballendat |
| 2003/0030568 A1 | 2/2003 | Lastinger et al. |
| 2005/0003763 A1 | 1/2005 | Lastinger et al. |
| 2005/0003865 A1 | 1/2005 | Lastinger et al. |
| 2005/0046578 A1 | 3/2005 | Pires |
| 2005/0052282 A1 | 3/2005 | Rodgers et al. |
| 2005/0060246 A1 | 3/2005 | Lastinger et al. |
| 2005/0174246 A1 | 8/2005 | Picco et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0164320 A1 | 7/2006 | Lastinger et al. |
| 2006/0220877 A1 | 10/2006 | Ferguson et al. |
| 2006/0270351 A1 | 11/2006 | Lastinger et al. |
| 2007/0159332 A1 | 7/2007 | Koblasz |
| 2007/0187501 A1 | 8/2007 | Lenkl et al. |
| 2007/0202809 A1 | 8/2007 | Lastinger et al. |
| 2007/0270774 A1 | 11/2007 | Bergman et al. |
| 2008/0116990 A1 | 5/2008 | Rokhsaz |
| 2008/0136597 A1 | 6/2008 | Choi et al. |
| 2008/0180217 A1 | 7/2008 | Isabell |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0256679 A1 | 10/2009 | Potyrailo et al. |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2010/0225482 A1 | 9/2010 | Kasai et al. |
| 2011/0025458 A1 | 2/2011 | Rokhsaz et al. |
| 2011/0025473 A1 | 2/2011 | Rokhsaz et al. |
| 2011/0041370 A1 | 2/2011 | Saint et al. |
| 2011/0092890 A1 | 4/2011 | Stryker et al. |
| 2011/0115635 A1 | 5/2011 | Petrovski et al. |
| 2011/0146123 A1 | 6/2011 | Dunn et al. |
| 2011/0153454 A1 | 6/2011 | Dunn et al. |
| 2011/0178375 A1 | 7/2011 | Forster |
| 2011/0263952 A1 | 10/2011 | Bergman et al. |
| 2011/0283459 A1 | 11/2011 | Essers |
| 2011/0289023 A1 | 11/2011 | Forster et al. |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0307309 A1 | 12/2011 | Forster et al. |
| 2011/0309937 A1 | 12/2011 | Bunza et al. |
| 2012/0067374 A1 | 3/2012 | Raspati |
| 2012/0092027 A1 | 4/2012 | Forster |
| 2012/0105233 A1 | 5/2012 | Bobey et al. |
| 2012/0119912 A1 | 5/2012 | Ortega et al. |
| 2012/0165772 A1 | 6/2012 | Groosman et al. |
| 2012/0173440 A1 | 7/2012 | Dehlinger et al. |

(56) References Cited

U.S. PATENT DOCUMENTS

| | | | |
|---|---|---|---|
| 2012/0216607 A1 | 8/2012 | Sjöholm et al. |
| 2012/0217311 A1 | 8/2012 | Rokhsaz et al. |
| 2012/0268278 A1 | 10/2012 | Lewis et al. |
| 2013/0079590 A1 | 3/2013 | Bengtson |
| 2013/0109929 A1 | 5/2013 | Menzel |
| 2013/0123726 A1 | 5/2013 | Yu et al. |
| 2013/0254141 A1 | 9/2013 | Barda et al. |
| 2013/0261409 A1 | 10/2013 | Pathak et al. |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0176307 A1 | 6/2014 | Forster |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0276504 A1 | 9/2014 | Heil et al. |
| 2014/0296808 A1 | 10/2014 | Curran et al. |
| 2015/0080819 A1 | 3/2015 | Chama et al. |
| 2015/0080834 A1 | 3/2015 | Mills |
| 2015/0087935 A1 | 3/2015 | Davis et al. |
| 2015/0227832 A1 | 8/2015 | Diorio et al. |
| 2016/0137396 A1 | 5/2016 | Brownfield |
| 2016/0171850 A1 | 6/2016 | Forster |
| 2016/0189021 A1 | 6/2016 | Forster |
| 2016/0232821 A1 | 8/2016 | Janko |
| 2016/0257858 A1 | 9/2016 | Zajaczkowski et al. |
| 2016/0267769 A1 | 9/2016 | Rokhsaz et al. |
| 2017/0011240 A1 | 1/2017 | Forster |
| 2017/0040692 A1 | 2/2017 | Peralta et al. |
| 2017/0076573 A1 | 3/2017 | Forster |
| 2017/0091498 A1 | 3/2017 | Forster et al. |
| 2017/0098044 A1 | 4/2017 | Lai et al. |
| 2018/0021184 A1 | 1/2018 | Monson et al. |
| 2018/0221216 A1 | 8/2018 | Benz et al. |
| 2019/0060137 A1 | 2/2019 | Severns et al. |
| 2020/0289338 A1 | 9/2020 | Severns et al. |

FOREIGN PATENT DOCUMENTS

| | | |
|---|---|---|
| CN | 102568259 | 7/2012 |
| CN | 202711437 | 1/2013 |
| CN | 102985853 | 3/2013 |
| DE | 4137631 | 5/1992 |
| DE | 69906388 | 2/2004 |
| DE | 69915370 | 3/2005 |
| DE | 69917491 | 5/2005 |
| DE | 60016946 | 6/2006 |
| DE | 102007050074 | 4/2009 |
| EP | 0335279 | 10/1989 |
| EP | 1147603 | 10/2001 |
| EP | 1149305 | 10/2001 |
| EP | 1153317 | 11/2001 |
| EP | 1218771 | 7/2002 |
| EP | 1286179 | 2/2003 |
| EP | 1153317 | 3/2003 |
| EP | 1147603 | 3/2004 |
| EP | 1410353 | 4/2004 |
| EP | 1149305 | 5/2004 |
| EP | 1218771 | 12/2004 |
| EP | 1286179 | 11/2005 |
| EP | 1684615 | 8/2006 |
| EP | 2014267 | 6/2007 |
| EP | 1868553 | 12/2007 |
| EP | 1897278 | 3/2008 |
| EP | 1959900 | 8/2008 |
| EP | 1994650 | 11/2008 |
| EP | 2019659 | 2/2009 |
| EP | 1410353 | 12/2009 |
| EP | 1897278 | 1/2010 |
| EP | 1684615 | 2/2010 |
| EP | 2156222 | 2/2010 |
| EP | 2313044 | 4/2011 |
| EP | 1959900 | 2/2012 |
| EP | 2452183 | 5/2012 |
| EP | 2496197 | 9/2012 |
| EP | 1994650 | 12/2012 |
| EP | 2542200 | 1/2013 |
| EP | 2579069 | 4/2013 |
| EP | 2582341 | 4/2013 |
| EP | 2542200 | 2/2014 |
| EP | 2444039 | 5/2014 |
| EP | 2729107 | 5/2014 |
| EP | 2738748 | 6/2014 |
| EP | 2739254 | 6/2014 |
| EP | 2156222 | 8/2015 |
| EP | 2496197 | 8/2015 |
| EP | 2019659 | 4/2016 |
| EP | 2582341 | 4/2016 |
| EP | 2739254 | 11/2016 |
| GB | 145.859 | 3/1919 |
| GB | 2145859 | 4/1985 |
| GB | 2408204 | 11/2003 |
| WO | WO 89/10110 | 11/1989 |
| WO | WO 94/20002 | 9/1994 |
| WO | WO 00/44091 | 7/2000 |
| WO | WO 01/25817 | 4/2001 |
| WO | WO 02/103645 | 12/2002 |
| WO | WO 2006/108540 | 10/2006 |
| WO | WO 2007/069968 | 6/2007 |
| WO | WO 2008/130298 | 10/2008 |
| WO | WO 2010/001271 | 1/2010 |
| WO | WO 2010/043368 | 4/2010 |
| WO | WO 2011/107580 | 9/2011 |
| WO | WO 2012/136157 | 10/2012 |
| WO | WO 2014/165041 | 10/2014 |
| WO | WO 2017/087452 | 5/2017 |

OTHER PUBLICATIONS

Extended European Search Report for European Patent Application No. 21172302.8; dated Jul. 20, 2021; 6 pages.

* cited by examiner

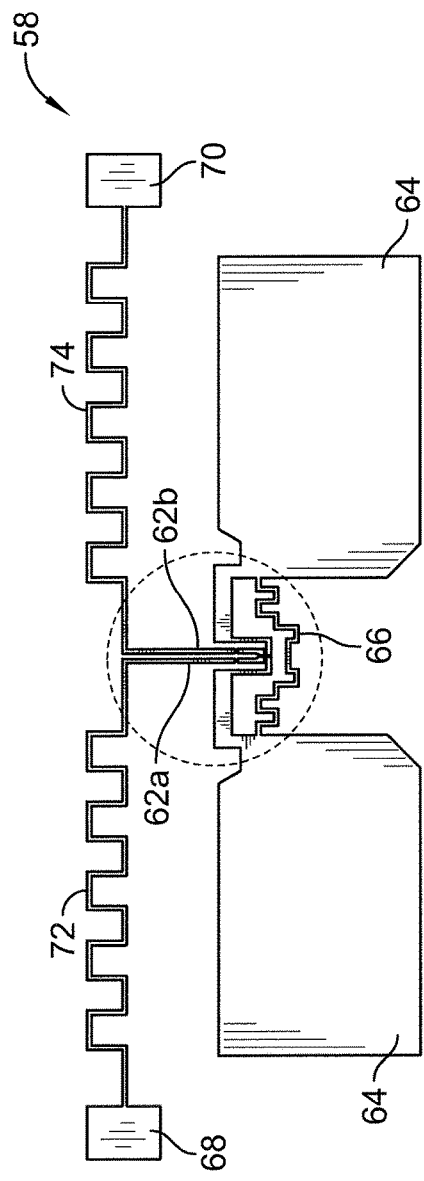
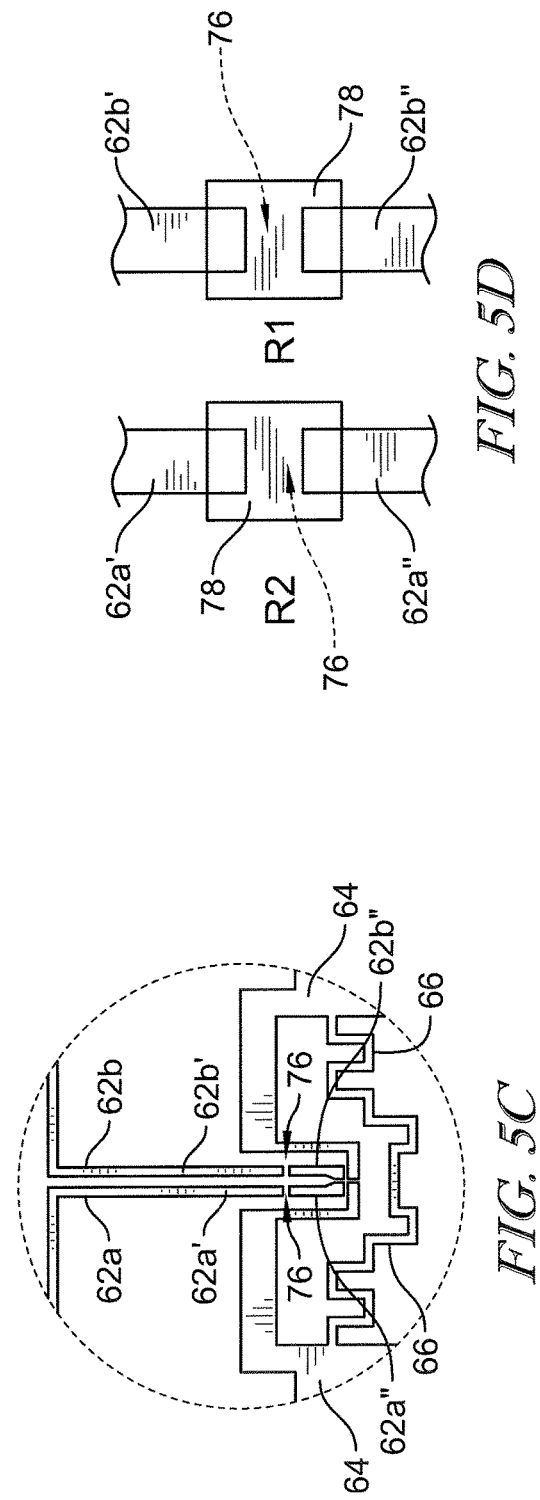
FIG. 5B
FIG. 5C
FIG. 5D

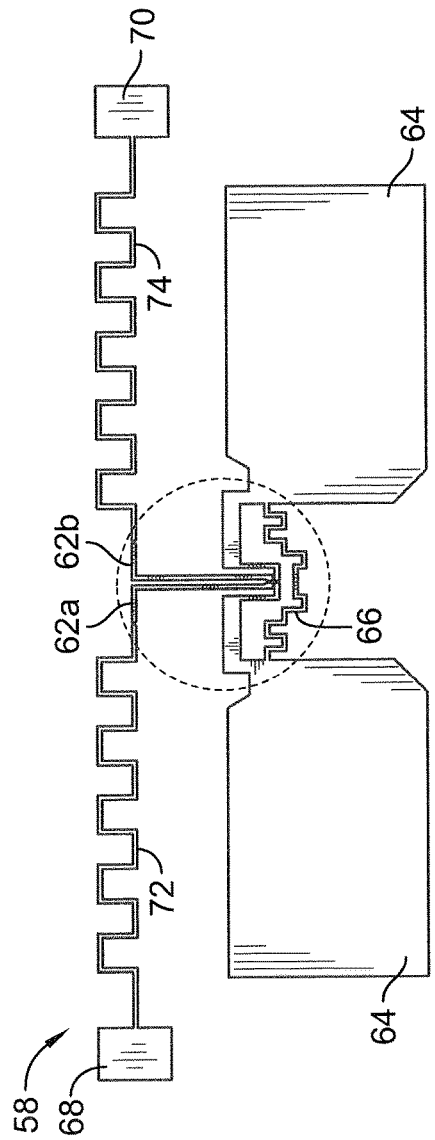
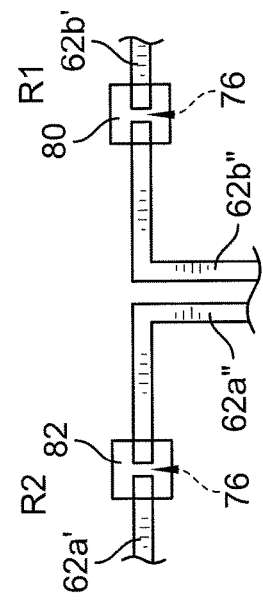
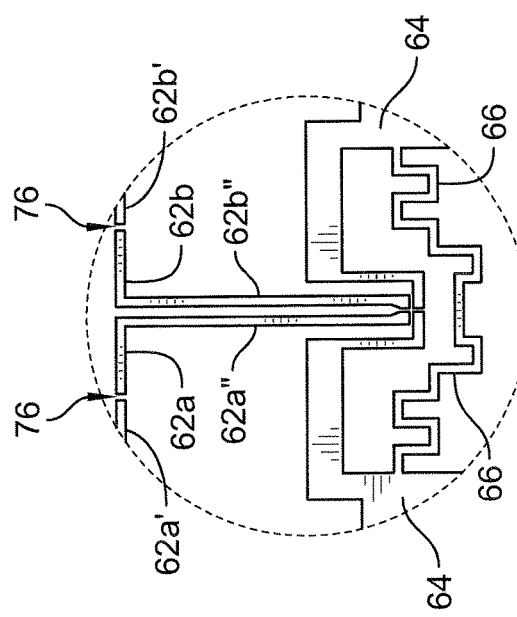
FIG. 6A
FIG. 6C
FIG. 6B

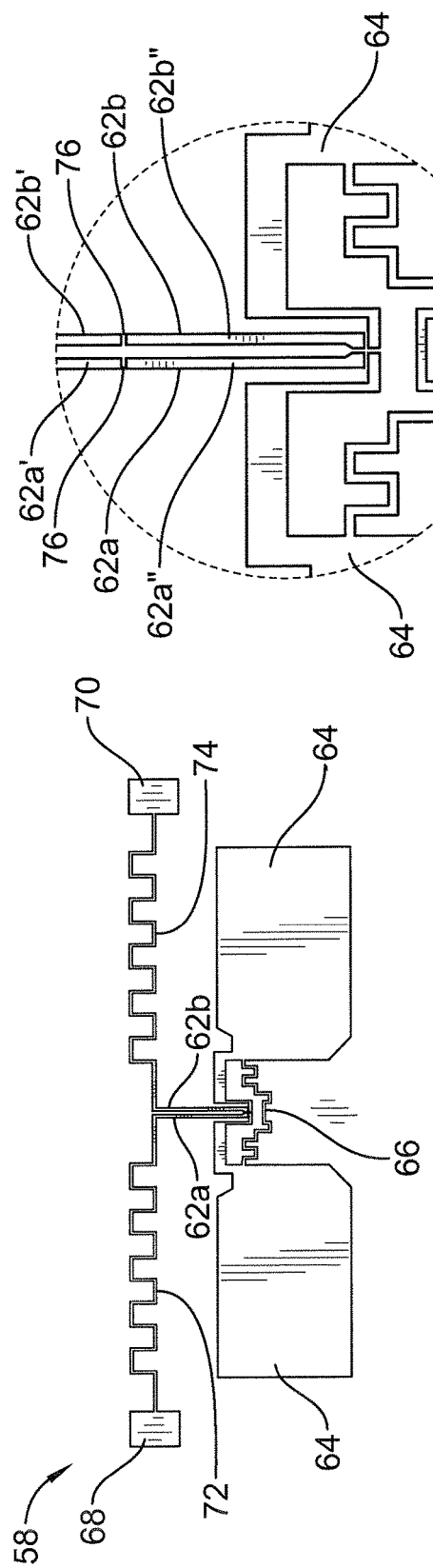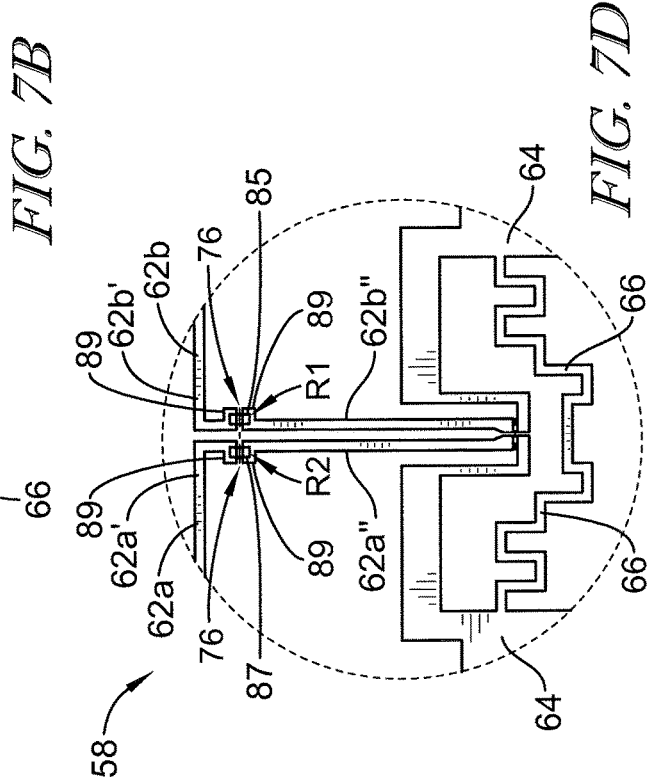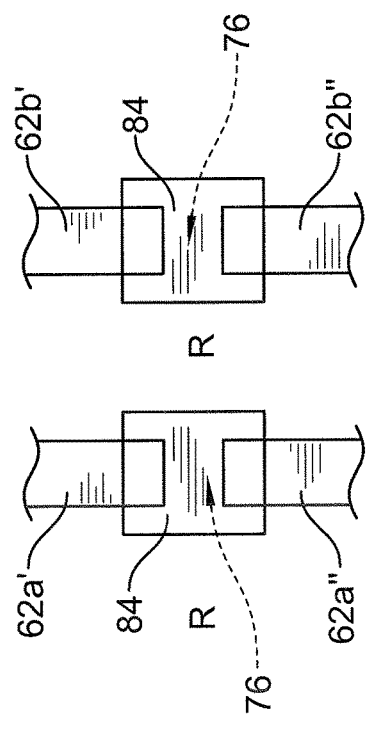

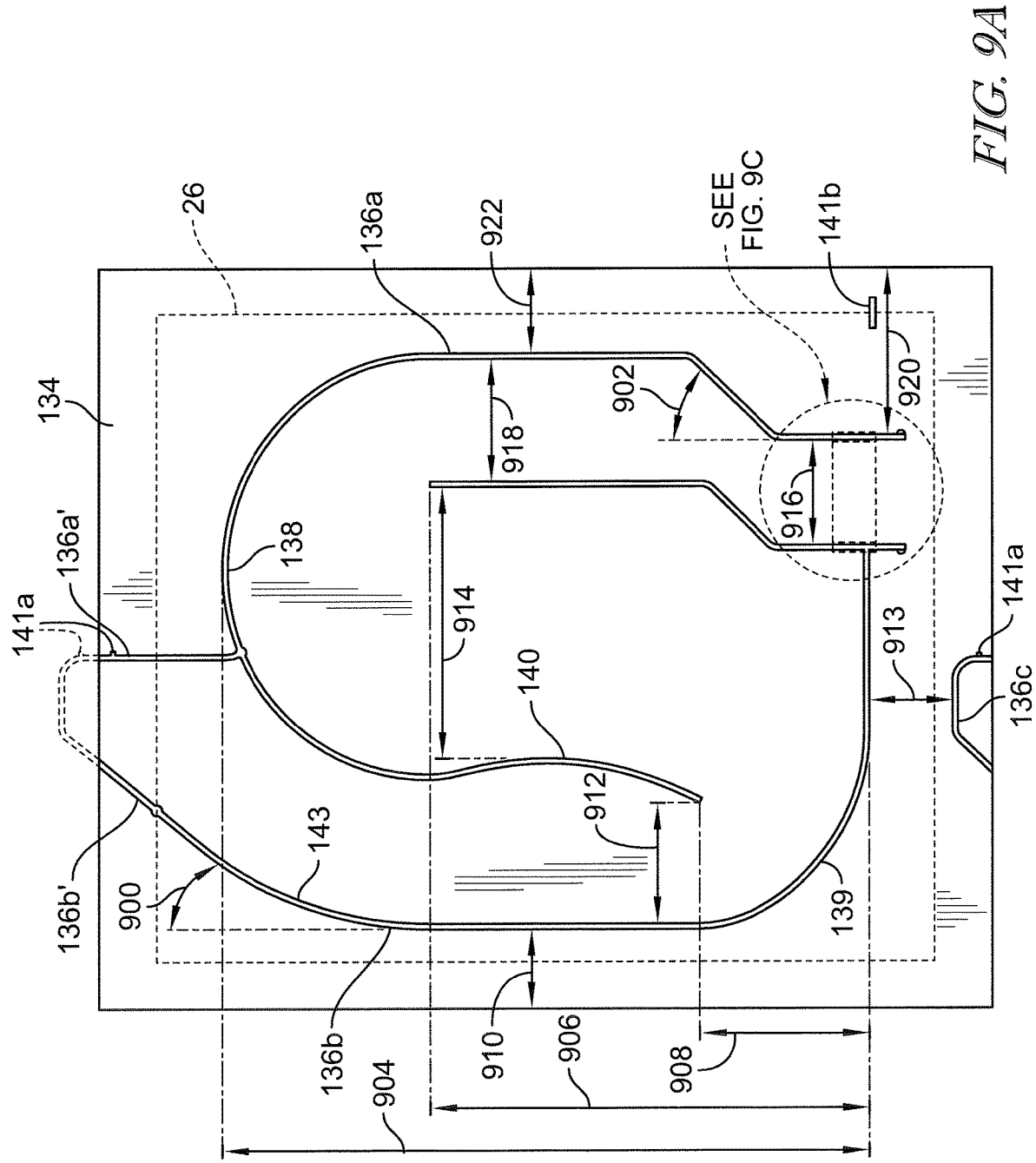

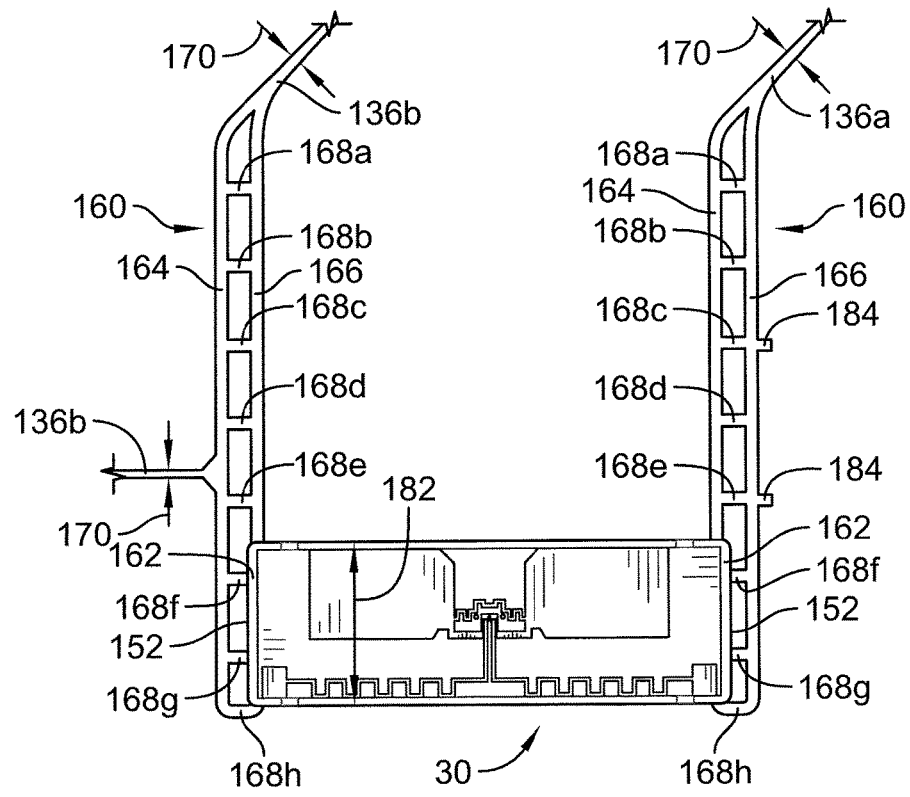
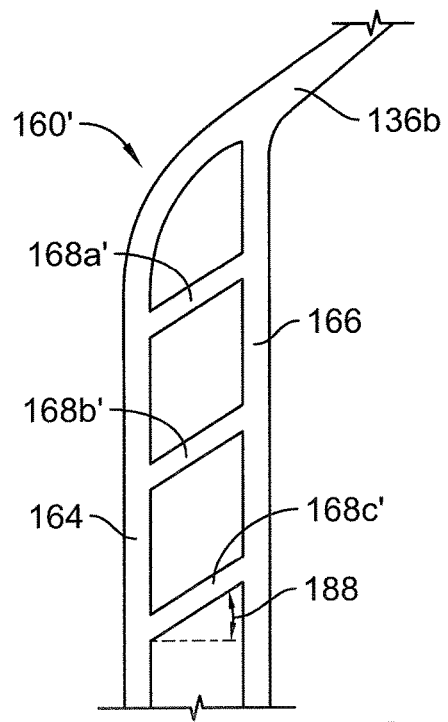
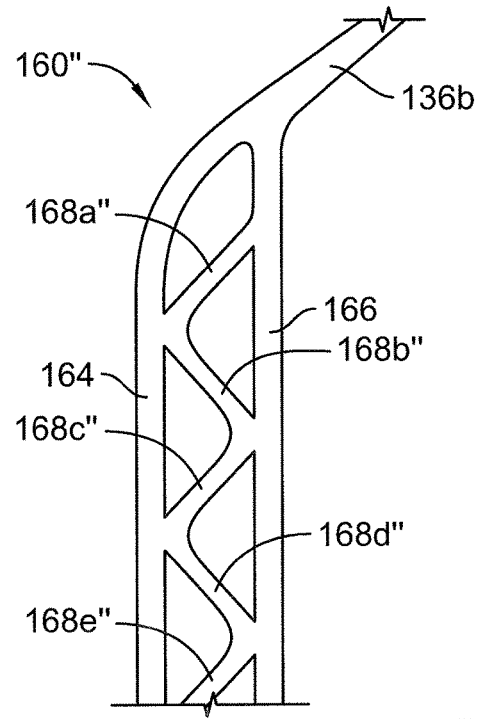
FIG. 14C
FIG. 14D
FIG. 14E

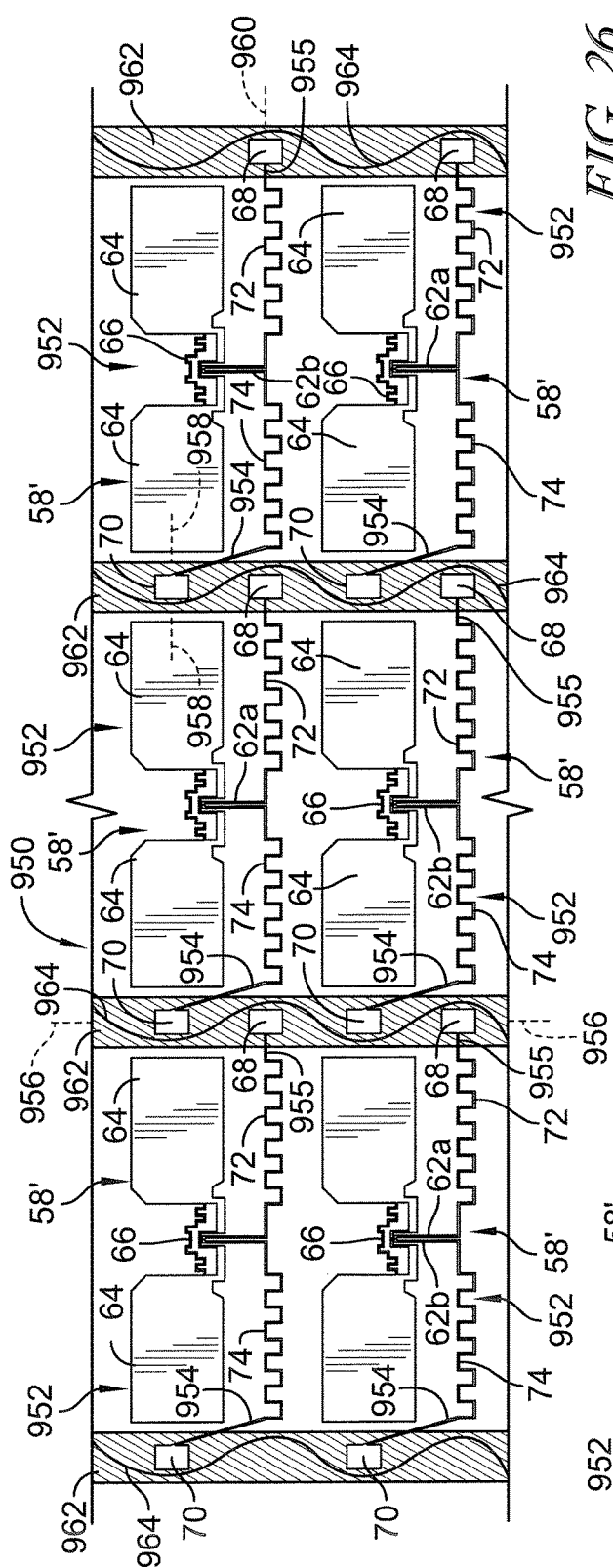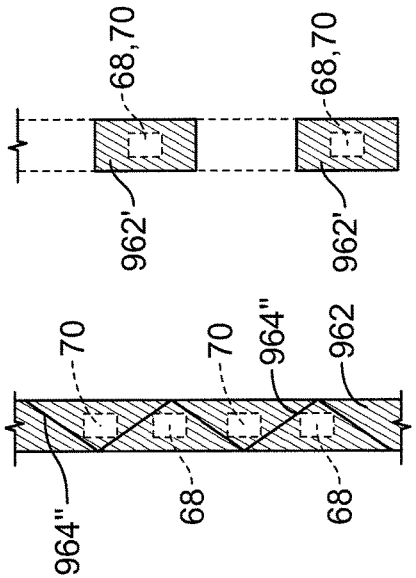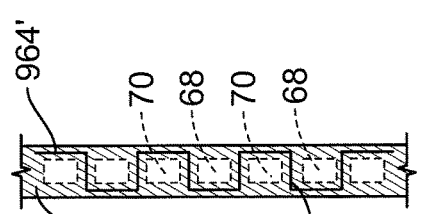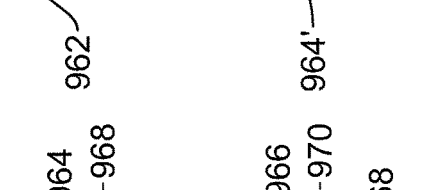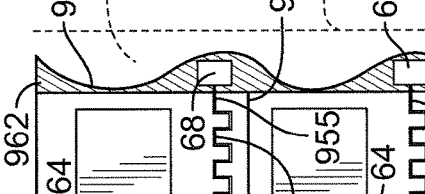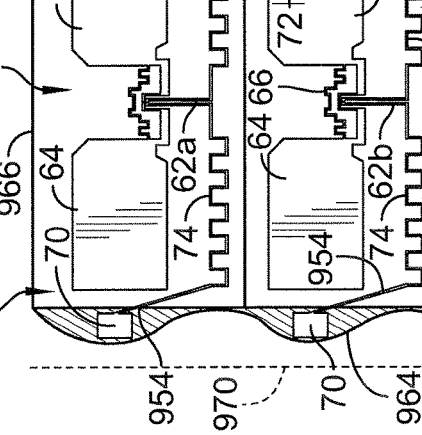

METHOD OF MANUFACTURING RFID TAGS

The present application is a continuation of U.S. application Ser. No. 17/242,352, filed Apr. 28, 2021, now U.S. Pat. Ser. No. 11/478,383, which is a continuation of U.S. application Ser. No. 16/889,903, filed Jun. 2, 2020, now U.S. Pat. No. 11,020,284, which is a continuation of U.S. application Ser. No. 16/110,603, filed Aug. 23, 2018, now U.S. Pat. No. 10,716,715, which claims the benefit, under 35 U.S.C. § 119(e), of U.S. Provisional Application No. 62/551,565, filed Aug. 29, 2017, U.S. Provisional Application No. 62/648,543, filed Mar. 27, 2018, and U.S. Provisional Application No. 62/660,558, filed Apr. 20, 2018, each of which is hereby incorporated by reference herein in its entirety.

BACKGROUND

The present disclosure relates to incontinence detection systems and particularly, to incontinence detection systems that use a pad beneath a person lying in a patient bed. More particularly, the present disclosure relates to incontinence detection systems that are able to communicate wirelessly between the pad and a reader on the patient bed.

Incontinence detection systems that have incontinence detection pads placed beneath a patient on a patient bed are known. For example, U.S. Pat. No. 5,537,095 discloses an incontinence detection pad having electrical circuitry that couples via a wired connection to a controller of a patient bed. Recent efforts have involved the development of wireless communication between the circuitry of the incontinence detection pad and a reader on a patient bed. See, for example, U.S. Patent Application Publication Nos. 2017/0065464 A1 and 2017/0246063 A1, and International Publication No. WO 2017/087452 A1 each of which is hereby incorporated by reference herein for all that it teaches.

Some incontinence detection pads include a layer having electrodes printed thereon and a passive radio frequency identification tag coupled to the electrodes. It is sometimes the case that false positive alerts are generated due to perspiration or medicinal gels, lotions, or creams leeching through the incontinence detection pad and coming into contact with the electrodes. In such situations the patient's skin may act as part of the electrical pathway between the electrodes in combination with the leeched moisture that contacts the electrodes. Accordingly, there is a need to eliminate the number of false positive alerts that occur in the prior art incontinence detection pads. Other improvements in incontinence detection pads and readers are also desirable.

SUMMARY

The present application discloses one or more of the features recited in the appended claims and/or the following features which, alone or in any combination, may comprise patentable subject matter:

According to the present disclosure, an absorbent article may include a topsheet that may be made of a fluid permeable material and a backsheet that may include a first layer of fluid impermeable material. A conductive ink pattern may be provided above the first layer and may be configured to form a first electrode trace and a second electrode trace. A passive radio frequency identification (RFID) tag may be attached to the first layer and may have electrical contacts that may couple to the first and second electrode traces. An absorbent core may be situated between the topsheet and the backsheet. A fluid filter layer may be situated so as to inhibit a low volume of fluid from being able to reach the first and/or second electrode traces beneath the absorbent core. After fluid of a sufficient volume greater than the low volume has passed through the topsheet, the absorbent core, and the fluid filter layer, an electrical pathway may be formed between the first and second electrode traces by the fluid which may enable the passive RFID tag to emit a signal that may indicate an incontinence event has occurred in response to the passive RFID tag being excited by external energy.

In some embodiments, the fluid filter layer may include a hydrophobic polymeric nonwoven material or a hydrophilic material. The hydrophobic polymeric nonwoven material may include, for example, one or more of the following: a spunbond material, a spunlace material, a meltblown material, or a meltspun material. Alternatively or additionally, the hydrophobic polymeric nonwoven material may include a polypropylene or polyethylene material that may have a pore size and basis weight that may be configured to prevent the low volume of fluid from penetrating therethrough due to surface tension of the fluid.

In some embodiments, the fluid filter layer may include a perforated film. Optionally, the perforated film may include one or more of the following: die cut holes, laser cut holes, or holes created by vacuum forming. Further optionally, the perforated film may include one or more of the following: low density polyethylene (LDPE), high density polyethylene (HDPE), polyethylene terephthalate (PET), or polypropylene. In some embodiments, the conductive ink pattern above the first layer may be printed on an underside of the perforated film. In such embodiments, the holes of the perforated film may all be spaced apart from the conductive ink pattern printed on the underside of the perforated film.

In some embodiments, the fluid filter layer may include an adhesive material that may be applied to a bottom of the absorbent core or to the backsheet. The adhesive material may include a hot melt adhesive or a polyethylene powder that is thermally bonded to the filter layer and absorbent core or backsheet as the case may be. For example, the adhesive material may be applied to the bottom of the absorbent core or to the backsheet so as to match a geometry of the first and/or second electrode traces thereby covering the respective first and/or second electrode traces. If desired, the adhesive material may include a hot melt adhesive. Alternatively of additionally, the adhesive material may comprise an adhesive film or may be spray coated on the bottom of the absorbent core. Further alternatively or additionally, the adhesive material may be slot coated on the bottom of the absorbent core. The adhesive material may be configured to have a first width greater than a second width of the first and second electrode traces so that adhesive material may extend beyond opposite sides of the first and second electrode traces. The first width may be from about 3 millimeters (mm) to about 25 mm and the second width may be about 1 mm. The first width may be defined by a shim of a slot coater that is used to apply the adhesive.

In some embodiments, the fluid filter layer may include a hydrophobic coating applied to the absorbent core. The hydrophobic coating may be applied in one or more of the following patterns: dots, stripes, or random pattern. The hydrophobic coating may be sprayed onto the absorbent core or applied as an adhesive film.

In some embodiments, the fluid filter layer may include a soluble coating that may be applied over the first and second electrode traces. For example, the soluble coating may include a water soluble coating. Alternatively or additionally, the soluble coating may include a urine soluble coating.

Optionally, the soluble coating may include a dissolvable ink. The soluble coating may be absent from portions of the first and second electrode traces at which the electrical contacts of the passive RFID tag may couple to the first and second electrode traces.

Alternatively or additionally, the fluid filter layer may include a cellulosic nonwoven material. For example, the cellulosic nonwoven material may include tissue paper.

If desired, the fluid filter layer may be situated above the absorbent core. Optionally, the fluid filter layer also may be situated above the topsheet. Alternatively, the fluid filter layer may be situated beneath the topsheet. Further alternatively, the fluid filter layer may be situated beneath the absorbent core.

In some embodiments, a first outer periphery of the fluid filter layer may be coextensive with a second outer periphery of the absorbent core. Alternatively or additionally, a first outer periphery of the fluid filter layer may be coextensive with a second outer periphery of the topsheet. Further alternatively or additionally, a first outer periphery of the fluid filter layer may be coextensive with a second outer periphery of the backsheet. Optionally, the fluid filter layer may be laminated to the absorbent core using one or more of the following: adhesive, heat bonding, or latex bonding.

In some embodiments, the fluid filter layer may include an adhesive with desiccant media. The adhesive with desiccant media may adhere the topsheet to the absorbent core, for example. Alternatively or additionally, the fluid filter layer may include a desiccant. For example, the desiccant may be sprayed onto the topsheet or the absorbent core or the backsheet.

If desired, the adhesive also may be applied so as to cover a sacrificial electrode trace portion that may be on the backsheet in spaced apart relation with the first and second electrodes. For example, the adhesive also may be applied to portions of the first and second electrode traces that may extend beyond a periphery of the absorbent core.

According to another aspect of the present disclosure, a method of manufacturing a passive RFID tag may include attaching an RFID integrated circuit chip to a first antenna inlay of a backsheet that may carry a plurality of antenna inlays. Each antenna inlay may include an antenna portion, a pair of electrical contact portions, and a sacrificial connecting portion that may interconnect the pair of electrical contact portions. The RFID integrated circuit chip may have electrical contacts that may electrically couple to the electrical contact portions of the first antenna inlay when the RFID integrated circuit chip is attached to the backsheet. The method may further include emitting energy to provide the RFID integrated circuit chip with power via the antenna portion of the first antenna inlay, receiving a return signal from the RFID integrated circuit chip transmitted via the antenna portion of the first antenna inlay, and processing the return signal from the RFID integrated circuit chip to confirm that the RFID integrated circuit chip may be working properly due to the return signal indicating that the respective pair of electrical contact portions and the respective sacrificial connection portion of the first antenna inlay form a completed short circuit. The method may further include cutting the backsheet material at a location which may sever at least a part of the sacrificial connecting portion from the pair of electrical contact portions of the first antenna inlay to place the pair of electrical contact portions of the first antenna inlay in an open circuit configuration and leaving the part of the sacrificial connecting portion behind on a portion of the backsheet that may be associated with a neighboring antenna inlay.

In some embodiments, at least one of the electrical contacts of the RFID integrated circuit chip may include a tamper input.

According to a further aspect of the present disclosure, an antenna inlay may include an antenna portion, a first electrical contact portion, and a second electrical contact portion. The first electrical contact portion may include a first electrical lead that may have a first gap formed therein to provide a first lead segment and a second lead segment. A first resistor may be placed across the gap to electrically interconnect the first and second lead segments.

In some embodiments, the second electrical contact portion may include a second electrical lead that may have a second gap formed therein to provide a third lead segment and a fourth lead segment. A second resistor may be placed across the second gap to electrically interconnect the third and fourth lead segments. Optionally, the second electrical contact portion may be configured as a mirror image of the first electrical contact portion.

In some embodiments including those having just the first gap or those having both the first and second gaps, the antenna portion, first electrical contact portion, and the second electrical contact portion may be coplanar. For example, the antenna portion, first electrical contact portion, and the second electrical contact portion comprise a metallic film. The metallic film may comprise aluminum. Optionally, a thickness of the metallic film may be about 9 micrometers ($\mu$m). Alternatively or additionally, the antenna portion may include a first antenna patch and a second antenna patch. If desired, the second antenna patch may be configured as a mirror image of the first antenna patch.

In some embodiments having both of the first and second gaps, the first resistor and the second resistor may have substantially equivalent resistances or the first resistor and the second resistor may have different resistances. For example, the resistance of at least one of the first and second resistors may be about 2.4 Mega Ohms (M$\Omega$). In one embodiment, the resistance of one of the first and second resistors may be about 2.4M$\Omega$ and the resistance of the other of the first and second resistors may be about 1.0M$\Omega$.

According to yet another aspect of the present disclosure, an absorbent article may include a topsheet that may be made of a fluid permeable material, a backsheet that may include a first layer of fluid impermeable material, and a conductive ink pattern that may be provided above the first layer and that may be configured to form a first electrode trace and a second electrode trace. A passive radio frequency identification (RFID) tag may be attached to the first layer and may have electrical contacts that may couple to the first and second electrode traces. An absorbent core may be situated between the topsheet and the backsheet. The absorbent core may have a first periphery that may be inboard of a second periphery of the topsheet and inboard of a third periphery of the backsheet. A first portion of the first electrode trace may extend beyond the first periphery and a second portion of the second electrode trace may extend beyond the first periphery. A fluid barrier layer may be situated over the first portion of the first electrode trace and over the second portion of the second electrode trace so as to inhibit fluid from being able to reach the first and second portions of the respective first and second electrode traces that may extend beyond the periphery of the absorbent core. After a sufficient volume of fluid has passed through the topsheet and the absorbent core, an electrical pathway may be formed between the first and second electrode traces by the fluid which may enable the passive RFID tag to emit a signal that may indicate an incontinence event has occurred in response to the passive RFID tag being excited by external energy.

In some embodiments, the fluid barrier layer may include an adhesive material that may be applied over the first portion and the second portion of the respective first and second electrode traces outboard of the first periphery. For example, the adhesive material may be applied to a bottom surface of the topsheet or to a top surface of the backsheet. Optionally, the adhesive material may include a hot melt adhesive. Further optionally, the adhesive material may be applied to the top surface of the backsheet by a slot coating process. For example, the slot coating process may use a shim that may have a first set of openings of a first width and a second set of openings each having a second width that may be larger than the first width. The second openings may be in registry with the first and second portions of the respective first and second electrode traces. In some embodiments, the first width may be about 1 mm and the second width may be from about 3 mm to about 25 mm. Optionally, a third width of the first and second electrode traces may be about 1 mm and the first and second portions of the first and second electrode traces may be generally centered within the second width such that adhesive material may extend beyond opposite sides of the first and second portions of the respective first and second electrode traces. The first width may be defined by a shim of a slot coater that may be used to apply the adhesive.

In some embodiments, a portion of the fluid barrier layer may extend over a part of the first and second electrode traces inboard of the first periphery of the absorbent core. In some embodiments, the second periphery of the topsheet may be substantially coextensive with the third periphery of the back sheet.

In some embodiments, the absorbent article may further include a fluid filter layer that may be situated so as to inhibit a low volume of fluid from being able to reach the first and second electrode traces beneath the absorbent core. The fluid filter layer may include a hydrophobic polymeric nonwoven material or a hydrophilic material. For example, the hydrophobic polymeric nonwoven material may include one or more of the following: a spunbond material, a spunlace material, a meltblown material, or a meltspun material. Alternatively or additionally, the hydrophobic polymeric nonwoven material may include polypropylene or polyethylene material having a pore size and basis weight configured to prevent the low volume of fluid from penetrating therethrough due to surface tension of the fluid.

In some embodiments, the fluid filter layer may include a perforated film. For example, the perforated film may include one or more of the following: die cut holes, laser cut holes, or holes created by vacuum forming. Alternatively or additionally, the perforated film may include one or more of the following: low density polyethylene (LDPE), high density polyethylene (HDPE), polyethylene terephthalate (PET), or polypropylene. If desired, the holes of the perforated film all may be spaced apart from the conductive ink pattern that may form the first and second electrode traces.

In some embodiments, the fluid filter layer may include an adhesive material that may be applied to a bottom of the absorbent core or to the backsheet. For example, the adhesive material may be applied to the bottom of the absorbent core or to the backsheet so as to match a geometry of the first and/or second electrode traces thereby covering the respective first and/or second electrode traces beneath the absorbent core. Optionally, the adhesive material may include a hot melt adhesive. Alternatively or additionally, the adhesive material may comprise an adhesive film or may be spray coated on the bottom of the absorbent core. If desired, the adhesive material may be slot coated on the bottom of the absorbent core. The adhesive material may be configured to have a first width that may be greater than a second width of the first and second electrode traces so that adhesive material may extend beyond opposite sides of the first and second electrode traces. For example, the first width may be from about 3 mm to about 25 mm and the second width may be about 1 mm.

In some embodiments, the fluid filter layer may include a hydrophobic coating that may be applied to the absorbent core. For example, the hydrophobic coating may be applied in one or more of the following patterns: dots, stripes, or random pattern. If desired, the hydrophobic coating may be sprayed onto the absorbent core or applied as an adhesive film.

In some embodiments, the fluid filter layer may include a soluble coating that may be applied over at least a portion of the first and second electrode traces. For example, the soluble coating may include a water soluble coating. Alternatively or additionally, the soluble coating may include a urine soluble coating. Further alternatively or additionally, the soluble coating may include a dissolvable ink. The soluble coating may be absent from portions of the first and second electrode traces at which the electrical contacts of the passive RFID tag may couple to the first and second electrode traces.

In some embodiments, the fluid filter layer may include a cellulosic nonwoven material. For example, the cellulosic nonwoven material may comprise tissue paper.

In some embodiments, the fluid filter layer may be situated above the absorbent core. In such embodiments, the fluid filter layer also may be situated above the topsheet. Alternatively, the fluid filter layer may be situated beneath the topsheet. On the other hand, the fluid filter layer may be situated beneath the absorbent core.

In some embodiments, a fourth periphery of the fluid filter layer may be coextensive with the first periphery of the absorbent core. Alternatively or additionally, a fourth periphery of the fluid filter layer may be coextensive with the second periphery of the topsheet. Alternatively, a fourth periphery of the fluid filter layer may be coextensive with the third periphery of the backsheet. If desired, the fluid filter layer may be laminated to the absorbent core using one or more of the following: adhesive, heat bonding, or latex bonding.

In some embodiments, the fluid filter layer may include an adhesive with desiccant media. The adhesive with desiccant media may adhere the topsheet to the absorbent core, for example.

In some embodiments, the fluid filter layer may include a desiccant. Optionally, the desiccant may be sprayed onto the topsheet or the absorbent core or the backsheet.

If desired, the adhesive also may be applied so as to cover a sacrificial electrode trace portion that may be on the backsheet in spaced apart relation with the first and second electrodes. Optionally, the adhesive of the fluid filter layer also may be applied to first and second portions of the respective first and second electrode traces that extend beyond the first periphery of the absorbent core.

According to still a further aspect of the present disclosure, a method of controlling an incontinence detection system includes establishing a first antenna of a plurality of antennae as a transmit antenna that may be used to wirelessly energize a passive RFID tag of an absorbent article at a first power level. The plurality of antennae may include N spaced apart antennae and N may be an integer equal to or greater than three. The method may further include establishing each of the plurality of antennae, except for the first antenna, as receive antennae that each may listen for backscattered data that may be emitted from the passive RFID tag. The method may further include reducing the first power level to a second power level if the receive antennae that are able to read the backscattered data exceeds a predetermined number of receive antennae and the predetermined number may be less than N−1.

In some embodiments, the method may further include analyzing signal to noise ratio between the transmit antenna and each of the receive antenna before reducing the first power level to the second power level. Alternatively or additionally, the method may further include analyzing a receive signal level (RSL) figure of merit (FoM) of the backscattered data before reducing the first power level to the second power level. Optionally, the RSL FoM of multiple emissions of backscattered data may be averaged before reducing the first power level to the second power level. Further alternatively or additionally, the method may further include determining that an external power flag may be set in the backscattered data before reducing the first power level to the second power level.

In some embodiments, the predetermined number of receive antennae may include two receive antennae. Alternatively, the predetermined number of receive antennae may include one receive antenna. In some embodiments, the first power level and the second power level lie within a range of about +20 decibel milliWatt (dBm) to about +33 dBm.

In some embodiments, the method may further include cycling through the plurality of antennae as being established as the transmit antenna with each of the remaining antennae of the plurality of antennae being established as the receive antenna for a period of time. Optionally, the plurality of antennae may be coupled to a bistatic radio frequency (RF) switch matrix which may be operable to establish which antenna of the plurality of antennae is the transmit antenna and to establish which antenna of the plurality of antennae is the receive antenna. The method may further include operating the bistatic RF switch matrix to cause the transmit antenna to transmit using a frequency hopping scheme. The frequency hopping scheme may uses 50 distinct frequencies, for example, with each frequency being used only once in a pseudo-random order before any of the 50 frequencies are repeated. In some embodiments, the 50 frequencies may lie within a range between about 902 MegaHertz (MHz) and 928 MHz.

According to yet a further aspect of the present disclosure, an absorbent article may include a topsheet that may be made of a fluid permeable material, a backsheet that may include a first layer of fluid impermeable material, an absorbent core that may be situated between the topsheet and the backsheet, and an insert layer that may be situated between the backsheet and the absorbent core. The insert layer may include a substrate, a conductive ink pattern that may be provided on the substrate and that may be configured to form a first electrode trace and a second electrode trace. A passive radio frequency identification (RFID) tag may be provided on the substrate and may have electrical contacts that may couple to the first and second electrode traces.

In some embodiments, the substrate may include paper or a cellulosic nonwoven material or tissue paper, for example. If desired, the backsheet may further include a second layer of nonwoven material. The first and second layers of the backsheet may be coupled together with a hot melt adhesive. Alternatively or additionally, the backsheet may further include a second layer of polypropylene and, optionally, these first and second layers of the backsheet may be coupled together with a hot melt adhesive.

In some embodiments, the absorbent article may further include a fluid filter layer that may be situated between the absorbent core and the insert layer. The fluid filter layer may be configured to inhibit a low volume of fluid from being able to reach the first and second electrode traces on the substrate of the insert layer. After fluid of a sufficient volume greater than the low volume has passed through the topsheet, the absorbent core, and the fluid filter layer, an electrical pathway may be formed between the first and second electrode traces by the fluid which may enable the passive RFID tag to emit a signal that may indicate an incontinence event may have occurred in response to the passive RFID tag being excited by external energy.

Optionally, the fluid filter layer may include a hydrophobic polymeric nonwoven material or a hydrophilic material. For example, such a hydrophobic polymeric nonwoven material may comprise one or more of the following: a spunbond material, a spunlace material, a meltblown material, or a meltspun material. If desired, the hydrophobic polymeric nonwoven material may include a polypropylene or polyethylene material having a pore size and basis weight that may be configured to prevent the low volume of fluid from penetrating therethrough due to surface tension of the fluid.

Also according to the present disclosure, an absorbent article may include a topsheet that may be made of a fluid permeable material, an absorbent core that may be situated beneath the topsheet, a substrate that may be situated beneath the absorbent core, a conductive ink pattern that may be provided on the substrate and that may be configured to form a first electrode trace and a second electrode trace, and a passive radio frequency identification (RFID) tag that may be attached to the substrate and that may have electrical contacts that may couple to the first and second electrode traces. The first and second electrode traces each may have a redundancy means for coupling to the electrical contacts of the passive RFID tag to provide redundant electrical pathways between the first and second electrode traces and the electrical contacts.

In some embodiments, the redundancy means may include portions of the first and second traces that each may have a ladder geometry. The ladder geometry of each of the first and second traces may have a pair of elongated sides and a series of rungs that may interconnect the respective elongated sides. Some or all of the rungs may be substantially perpendicular to the elongated sides. Alternatively or additionally, some or all of the rungs may not be perpendicular to the elongated sides such that the rungs each may extend between the elongated sides at an inclined angle.

In some embodiments, the ladder geometry of the first trace may be substantially parallel with the ladder geometry of the second trace. Furthermore, the ladder geometries of the first and second traces may have substantially equivalent lengths. Optionally, the ladder geometry of the first trace may be offset along its length compared to the ladder geometry of the second trace such that first and second ends of the ladder geometry of the first trace may not be aligned with first and second ends, respectively, of the ladder geometry of the second trace.

Optionally, a first spacing between outer edges of the elongated sides of the ladder geometry of the first and second electrode traces may be at least three times a width of portions of the first and second electrode traces that are spaced from the ladder geometry. Further optionally, a first spacing between outer edges of the elongated sides of the ladder geometry of the first and second electrode traces may be at least four times a width of portions of the first and second electrode traces that are spaced from the ladder geometry.

Opposite ends of the passive RFID tag each may overlie respective first elongated sides of the pair of elongated sides of each ladder geometry. In such embodiments, second elongated sides of the pair of elongated sides of each ladder geometry may be outboard of the respective end of the passive RFID tag. If desired, more than one rung of each ladder geometry may extend out and away from the respective end of the passive RFID tag.

In some embodiments, the ladder geometry may have a length that may be at least three times a width dimension of the passive RFID tag. Optionally, first and second registration marks may be aligned with respective rungs of the associated ladder geometry and may extend outwardly from one of the elongated sides of the associated ladder geometry to indicate a mid-region of the length of the ladder geometry at which the passive RFID tag may be aligned when attached to the substrate.

In some embodiments, the redundancy means may include end regions of the first and second electrode traces that may be wider than portions of the first and second electrode traces that are spaced from the end regions. For example, the end regions may be at least three times wider than the portions of the first and second electrode traces that are spaced from the end regions. As another example, the end regions may be at least four times wider than the portions of the first and second electrode traces that are spaced from the end regions.

If desired, the end regions may be formed as solid conductive ink regions. Opposite ends of the passive RFID tag may terminate within the end regions such that portions of the end regions may extend outwardly beyond the opposite ends of the passive RFID tag. In some embodiments, the end regions of the first and second electrode traces may be generally straight, the opposite ends of the passive RFID tag may be generally straight, and the opposite ends of the passive RFID tag may be generally parallel with the end regions. Optionally, the end regions each may have a length that is at least three times a width dimension of the passive RFID tag.

In some embodiments, the redundancy means may include portions of the first and second electrode traces that each may have a comb pattern. For example, the comb pattern of the first and second traces each may include an elongated side and a series of teeth extending from a respective elongated side. If desired, the teeth of each comb pattern may extend in substantially perpendicular relation with the respective elongated side.

The teeth of the comb pattern of the portion of the first electrode trace and the teeth of the comb pattern of the portion of the second electrode trace may extend toward each other. Opposite ends of the passive RFID tag each may overlie a plurality of teeth of the respective comb pattern and the elongated sides of each comb pattern may be outboard of the respective end of the passive RFID tag.

In some embodiments, a first width of the comb pattern of the portions of the first and second electrode traces may be at least three times a second width of thin portions of the first and second electrode traces that are spaced from the respective comb pattern. In some embodiments, a first width of the comb pattern of the portions of the first and second electrode traces may be at least four times a second width of portions of the first and second electrode traces that are spaced from the respective comb pattern. Optionally, each comb pattern may have a length that is at least three times a width dimension of the passive RFID tag.

In some embodiments, the redundancy means may include end regions of the first and second electrode traces that are wider than portions of the first and second electrode traces that are spaced from the end regions. Optionally, each of the end regions may have a series of holes through the conductive ink forming the respective end region such that the substrate may be exposed through the series of holes. At least some of holes of the series of holes of the end regions may be substantially quadrilateral in shape. For example, the substantially quadrilateral shape may include at least one of substantially square, substantially rectangular, or substantially rhomboid. Alternatively or additionally, at least some of holes of the series of holes may be substantially circular in shape.

In some embodiments, each of the end regions may be substantially straight and the circular holes may be aligned along a length of the straight end regions. If desired, each of the end regions may be substantially straight with each end region having a first elongated straight edge and a second elongated straight edge and each circular hole may be located about midway between the first and second elongated straight edges of the respective end region. Opposite ends of the passive RFID tag each may overlie a portion of a plurality of circular holes of each series of circular holes of the respective end region and a portion of each end region may be outboard of the respective end of the passive RFID tag.

With regard to the embodiments having holes of other shapes, each of the end regions may be substantially straight and the series of holes of each end region may be aligned along a length of the respective end region. For example, each end regions may be substantially straight with each end region having a first elongated straight edge and a second elongated straight edge and each hole of the series of holes may be located about midway between the first and second elongated straight edges of the respective end region.

In some embodiments, the end regions may be at least three times wider than portions of the first and second electrode traces that are spaced from the end regions. In some embodiments, the end regions are at least four times wider than portions of the first and second electrode traces that are spaced from the end regions.

Optionally, opposite ends of the passive RFID tag each may overlie a portion of a plurality of holes of each series of holes of the respective end region and a portion of each end region may be outboard of the respective end of the passive RFID tag. The end regions of the first and second electrode traces may be generally straight, the opposite ends of the passive RFID tag may be generally straight, and the opposite ends of the passive RFID tag may be generally parallel with the end regions. If desired, the end regions each may have a length that is at least three times a width dimension of the passive RFID tag.

In some embodiments, the redundancy means may include portions of the first and second traces that are each configured as an elongated loop. Each elongated loop may include a first elongated segment, a second elongated segment that may be substantially parallel with the first elongated segment, and an end segment that may interconnect ends of the first and second elongated segments. If desired, opposite ends of the passive RFID tag may be located over respective spaces between corresponding first and second elongated segments of the associated elongated loop. Optionally, each of the opposite ends of the passive RFID tag may be straight and substantially parallel with the first and second elongated segments of the elongated loops.

In some embodiments, each of the first, second, and end segments may have a width of a first dimension thereacross and portions of the first and second electrode traces spaced from the elongated loops also may have widths thereacross substantially equal to the first dimension. If desired, the elongated loops each may have a length that is at least three times a width dimension of the passive RFID tag.

In some embodiments of the absorbent articles including the redundancy means, the substrate may comprise a backsheet that may include a first layer of fluid impermeable material and a second layer of nonwoven material and the conductive ink may be provided on the first layer of the backsheet. The absorbent article may further include a fluid filter layer that may be situated so as to inhibit a low volume of fluid from being able to reach the first and second electrode traces beneath the absorbent core.

In some embodiments of the absorbent article including the redundancy means, a backsheet may be provided beneath the substrate and the substrate may comprise an insert layer situated between the backsheet and the absorbent core. The substrate may comprise paper or a cellulosic nonwoven material or tissue paper, for example.

According to still another aspect of the present disclosure, an absorbent article may include a substrate, a first electrode on the substrate, a second electrode on the substrate, the second electrode may be spaced from the first electrode, and circuitry that may be coupled to the first and second electrodes. The circuitry may be operable to monitor whether a biofluid may be present on the substrate by determining whether the first and second electrodes are in an open circuit configuration or a closed circuit configuration. The open circuit configuration may be indicative of an absence of biofluid and a closed circuit configuration may be indicative of a presence of biofluid, The absorbent article may further include a plurality of high wick bridges that may interconnect the first and second electrodes.

In some embodiments, the first electrode may include a generally straight first segment, the second electrode may include a generally straight second segment, and at least some of the high wick bridges may include a generally straight main segment that may be substantially perpendicular to the first and second segments. If desired, at least some of the high wick bridges may include a series of hash segments that may be substantially perpendicular with the main segment. In some embodiments, the main segment may bisect each of the hash segments. Alternatively or additionally, the hash segments may be of substantially equivalent lengths.

In some embodiments, the absorbent article may further include a hydrophobic material that may be situated within each of a plurality of zones bounded by respective portions of the first and second electrodes and by respective pairs of adjacent high wick bridges. The hydrophobic material may comprise a hydrophobic coating, for example. Optionally, the hydrophobic material in at least some of the zones may be quadrilateral in shape. Each of the high wick brides may include a main segment and a series of hash segments that may extend across the main segment. Ends of the hash segments may terminate at, or may be in close proximity to, a respective boundary of the hydrophobic material in each zone. If desired, the circuitry may include a radio frequency identification (RFID) tag. For example, the RFID tag may comprise a passive RFID tag.

According to a yet further aspect of the present disclosure, an absorbent article may include a substrate, a first series of spaced apart hydrophilic fluid guide paths that may be located on a right side of the substrate, and a second series of spaced apart hydrophilic fluid guide paths that may be located on a left side of the substrate. The first and second hydrophilic guide paths of the first series and second series may be mirror images of each other. The hydrophilic fluid guide paths may be configured to direct moisture away from a patient that may be situated atop a central region of the substrate.

In some embodiments, each fluid guide path of the first and second series of fluid guide paths may extend from the central region of the substrate beyond a footprint of the patient's body to a side region of the substrate beyond the footprint of the patient's body. Evaporation of moisture in the side regions on opposite sides of the footprint may produce a moisture gradient within the hydrophilic fluid guide paths so that moisture within the footprint may move outwardly to the side regions away from the patient. Alternatively or additionally, pressure produced on the fluid guide paths by the patient in the central region may result in moisture moving outwardly to the side regions away from the patient. If desired, the substrate may be generally rectangular in shape and each fluid guide path of the first and second series of guide paths may be oriented generally along a long dimension of the substrate. The absorbent article may further include a hydrophobic material in a central region of the substrate.

According to still a further aspect of the present disclosure, an absorbent article may include a topsheet that may be made of a fluid permeable material, a backsheet, and a conductive ink pattern that may be provided above the backsheet and that may be configured to form a first electrode and a second electrode. The absorbent article may further include a passive radio frequency identification (RFID) tag that may be between the topsheet and backsheet and that may have electrical contacts that may couple to the first and second electrodes. An absorbent core may be situated between the topsheet and the backsheet and may be above the first and second electrodes. A first fluid filter layer may be situated above the first and second electrodes so as to inhibit a low volume of fluid from being able to reach the first and/or second electrode beneath the absorbent core. After fluid of a sufficient volume greater than the low volume has passed through the topsheet, the absorbent core, and the fluid filter layer, an electrical pathway may be formed between the first and second electrodes by the fluid which may enable the passive RFID tag to emit a signal indicating an incontinence event may have occurred in response to the passive RFID tag being excited by external energy. The absorbent article also may have a second fluid filter layer that may be beneath the first and second electrodes. The second fluid filter layer may inhibit fluid from reaching the first and second electrodes from below.

In some embodiments, the backsheet may include an upper layer and a lower layer and the second fluid filter layer may be situated above the upper layer and below the first and second electrodes. For example, the second fluid filter layer may abut an upper surface of the upper layer and the first and second electrodes may be printed on the second fluid filter layer.

In other embodiments, the backsheet may include an upper layer and a lower layer and the second fluid filter layer may be situated between the upper layer and the lower layer of the backsheet. Thus, an upper surface of the second fluid filter layer may abut a bottom surface of the upper layer of the backsheet and a bottom surface of the second fluid filter layer may abut a top surface of the lower layer of the backsheet.

In still other embodiments, the backsheet may include an upper layer and a lower layer and wherein the second fluid filter layer may be situated beneath the lower layer. For example, an upper surface of the second fluid filter layer may abut a bottom surface of the lower layer of the backsheet.

Optionally, the first and/or second fluid filter layers may include a hydrophobic polymeric nonwoven material or a hydrophilic material. The hydrophobic polymeric nonwoven material may include one or more of the following: a spunbond material, a spunlace material, a meltblown material, or a meltspun material. Alternatively or additionally, the hydrophobic polymeric nonwoven material may include a polypropylene or polyethylene material having a pore size and basis weight configured to prevent fluid from penetrating the first and/or second fluid filter layers due to surface tension of the fluid.

If desired, the first fluid filter layer may include a perforated film and the second fluid filter layer may include a non-perforated film. The perforated film may include one or more of the following: die cut holes, laser cut holes, or holes created by vacuum forming. The perforated film and the non-perforated film may include one or more of the following: low density polyethylene (LDPE), high density polyethylene (HDPE), polyethylene terephthalate (PET), or polypropylene. In some embodiments, the conductive ink pattern above the backsheet may be printed on an underside of the perforated film. In such embodiments, holes of the perforated film all may be spaced apart from the conductive ink pattern that may be printed on the underside of the perforated film.

In some embodiments, the first fluid filter layer may include adhesive material that may be applied to a bottom of the absorbent core and/or the second fluid filter layer may include adhesive material that may be applied to a surface of the backsheet. Optionally, the adhesive material may be applied to the bottom of the absorbent core and to the surface of the backsheet so as to match a geometry of the first and second electrodes thereby to sandwich the first and second electrodes between the adhesive material. The adhesive material may include a hot melt adhesive or a polyethylene powder that is thermally bonded to the first and second fluid filter layers, to the absorbent core, and to the surface of the backsheet.

It is contemplated by this disclosure that the adhesive material may include an adhesive film or may be spray coated on the bottom of the absorbent core and on the surface of the backsheet. Alternatively or additionally, the adhesive material may be slot coated on the bottom of the absorbent core and on the surface of the backsheet. The adhesive material may be configured to have a first width greater than a second width of the first and second electrodes so that adhesive material of the first and second fluid filter layers extends beyond opposite sides of the first and second electrodes. For example, the first width may be from about 3 millimeters (mm) to about 25 mm and the second width may be about 1 mm. The first width may be defined by a shim of a slot coater that may be used to apply the adhesive.

In some embodiments, the first fluid filter layer may include a hydrophobic coating that may be applied to the absorbent core and/or the second fluid filter layer may include a hydrophobic coating that may bed applied to a surface of the backsheet. The hydrophobic coating may be applied in one or more of the following patterns: dots, stripes, or random pattern. Alternatively or additionally, the hydrophobic coating may be sprayed onto the absorbent core and/or the surface of the backsheet or may be applied as an adhesive film to the absorbent core and/or the surface of the backsheet.

Optionally, the first fluid filter layer may include a soluble coating that may be situated over the first and second electrodes and/or the second fluid filter layer may include a non-soluble coating that may be situated beneath the first and second electrodes. For example, the soluble coating may include a water soluble coating, a urine soluble coating, and/or a dissolvable ink. In some embodiments, the soluble coating may be absent from portions of the first and second electrodes at which the electrical contacts of the passive RFID tag may couple to the first and second electrodes.

In some embodiments, the first fluid filter layer may include a cellulosic nonwoven material and/or the second fluid filter layer may include a cellulosic nonwoven material. For example, the cellulosic nonwoven material comprises tissue paper.

If desired, the first fluid filter layer may be situated above the absorbent core. Optionally, the first fluid filter layer also may be situated above the topsheet. Alternatively, the first fluid filter layer may be situated beneath the topsheet. Further alternatively, the first fluid filter layer may be situated beneath the absorbent core.

In some embodiments, a first outer periphery of the first fluid filter layer may be coextensive with a second outer periphery of the absorbent core and/or a third outer periphery of the second fluid filter layer may be coextensive with the second outer periphery of the absorbent core. In other embodiments, a first outer periphery of the first fluid filter layer may be coextensive with a second outer periphery of the topsheet and/or a third outer periphery of the second fluid filter layer may be coextensive with the second outer periphery of the topsheet. In further embodiments, a first outer periphery of the first fluid filter layer may be coextensive with a second outer periphery of the backsheet and/or a third outer periphery of the second fluid filter layer may be coextensive with the second outer periphery of the backsheet.

Optionally, the first fluid filter layer may be laminated to the absorbent core using one or more of the following: adhesive, heat bonding, or latex bonding and/or the second fluid filter layer may be laminated to a surface of the absorbent core using one or more of the following: adhesive, heat bonding, or latex bonding. If desired, the first fluid filter layer and/or the second fluid filter layer may include an adhesive with desiccant media. Alternatively or additionally, the first fluid filter layer and/or the second fluid filter layer may include a desiccant. The desiccant may be sprayed onto the topsheet and/or the absorbent core and/or the backsheet.

In some embodiments, the adhesive also may be applied so as to cover a sacrificial electrode trace portion that may be situated above the backsheet in spaced apart relation with the first and second electrodes. Alternatively or additionally, the adhesive also may be applied to portions of the first and second electrodes that extend beyond a periphery of the absorbent core.

The present disclosure contemplates that the absorbent article of each of the contemplated embodiments mentioned herein may be of a variety of different types. For example, the absorbent article may comprise an incontinence detection pad. Such an incontinence detection pad may be placed between a patient and a mattress of a patient support apparatus that supports the patient in a healthcare facility. Alternatively, the absorbent article may comprise an incontinence detection garment such as a diaper. Further alternatively, the absorbent article may comprise a feminine hygiene product.

According to yet another aspect of the present disclosure, an apparatus may include a backing sheet and a plurality of RFID electrical inlays that may be arranged on the backing sheet. Each RFID electrical inlay may include at least one antenna portion and a pair of electrical contact portions. Each of the pair of electrical contact portions may terminate at an electrical contact pad such that one of the electrical contact pads may be a right pad and such that another electrical contact pad may be a left pad of the respective RFID electrical inlay. Some of the RFID electrical inlays may be arranged on the backing sheet in adjacent first and second columns that may have the right pads of the first column substantially aligned with the left pads of the second column such that the right and left pads of the first and second columns, respectively, may be spaced apart and alternate along a first hypothetical line that may extend through the right and left pads of the first and second columns.

In some embodiments, others of the RFID electrical inlays may be arranged on the backing sheet in a third column adjacent the second column and may have the right pads of the second column substantially aligned with the left pads of the third column such that the right and left pads, of the second and third columns, respectively, may be spaced apart and alternate along a second hypothetical line that may extend through the right and left pads of the second and third columns. A first stripe of electrically conductive adhesive may be arranged on the backing sheet so as to cover the alternating right and left pads of the first and second columns. Alternatively or additionally, a second stripe of electrically conductive adhesive may be arranged on the backing sheet so as to cover the alternating right and left pads of the second and third columns. Further alternatively or additionally, a third stripe of electrically conductive adhesive may be arranged on the backing sheet so as to cover the left pads of the first column and, if desired, a fourth stripe of electrically conductive adhesive may be arranged on the backing sheet so as to cover the right pads of the third column.

Optionally, a width of the first, second, third, and fourth stripes of electrically conductive adhesive, if present, may be less than about twice a width of the respective right and left pads covered by the respective first, second, third, and fourth stripes of electrically conductive adhesive. At least one of the first, second, third, and fourth stripes of electrically conductive adhesive may include a substantially continuous stripe of electrically conductive adhesive. Alternatively, each of the first, second, third, and fourth stripes of electrically conductive adhesive may include a continuous stripe of electrically conductive adhesive. Further alternatively, at least one of the first, second, third, and fourth stripes of electrically conductive adhesive may include an intermittent stripe of electrically conductive adhesive.

In embodiments having two columns of RFID electrical inlays, a stripe of electrically conductive adhesive may be arranged on the backing sheet so as to cover the alternating right and left pads of the first and second columns. Optionally, the strip of electrically conductive adhesive may include a continuous stripe or an intermittent stripe.

In some embodiments, each of the electrical contact portions may include a left undulated segment and a right undulated segment. A first substantially straight segment may extend substantially perpendicular with the first hypothetical line and may interconnect the respective right pad with the corresponding right undulated segment. A second substantially straight segment may extend at an angle with respect to the first hypothetical line and may interconnect the respective left pad with the corresponding left undulated segment.

It is contemplated by this disclosure that the left pad of each RFID electrical inlay may be located beside the at least one antenna such that a second hypothetical line, that may be substantially perpendicular to the first hypothetical line, may extend through a first center of the left pad and may intersect the at least one antenna. Alternatively or additionally, the right pad of each RFID electrical inlay may be located such that a third hypothetical line, that may be substantially perpendicular to the first hypothetical line, may extend through a second center of the right pad and may not intersect the at least one antenna.

According to still another aspect of the present disclosure, a method may include providing a backing sheet that may carry a plurality of RFID electrical inlays. Each RFID electrical inlay may include at least one antenna portion and a pair of electrical contact portions. Each of the pair of electrical contact portions may terminate at an electrical contact pad such that one of the electrical contact pads may be a right pad and such that another electrical contact pad may be a left pad of the respective RFID electrical inlay. Some of the RFID electrical inlays may be arranged on the backing sheet in adjacent first and second columns having the right pads of the first column substantially aligned with the left pads of the second column such that the right and left pads of the first and second columns, respectively, may be spaced apart and alternate along a first hypothetical line that may extend through the right and left pads of the first and second columns. The method may further include cutting the backing sheet along a cutline that may weave back and forth between the alternating right and left pads of the first and second columns.

In some embodiments, after cutting the backing sheet along the cutline, the first column may be separated from the second column and the method may further include attaching the first column to a second backing sheet that may be wider than the first column. If desired, the cutline may be substantially sinusoidal in shape. Alternatively, the cutline may be shaped as a triangle wave or a square wave.

It is contemplated by this disclosure that, after cutting the backing sheet along the cutline, the first column may be separated from the second column and the method may further include cutting the first column widthwise to separate each of the RFID electrical inlays of the first column from one another. The method may further include cutting the second column widthwise to separate each of the RFID electrical inlays of the second column from one another.

In some embodiments, prior to cutting the backing sheet along the cutline, the method may include applying electrically conductive adhesive over the right and left pads of the RFID electrical inlays of the first and second columns. For example, applying the electrically conductive adhesive over the right and left pads of the RFID electrical inlays of the first and second columns may include applying the electrically conductive adhesive as a substantially continuous stripe over the right and left pads of the RFID electrical inlays of the first and second columns.

Optionally, some of the RFID electrical inlays may be arranged on the backing sheet in a third column that may be adjacent the second column with the right pads of the second column substantially aligned with the left pads of the third column such that the right and left pads of the second and third columns, respectively, may be spaced apart and may alternate along a second hypothetical line extending through the right and left pads of the second and third columns. The method may further include cutting the backing sheet along a second cutline that weaves back and forth between the alternating right and left pads of the second and third columns.

In some embodiments, after cutting the backing sheet along the second cutline, the third column may be separated from the second column and the method may further include attaching the third column to a second backing sheet that may be wider than the third column. If desired, the second cutline may be substantially sinusoidal in shape. Alternatively, the second cutline may be shaped as a triangle wave or a square wave.

It is contemplated by this disclosure that, after cutting the backing sheet along the second cutline, the third column may be separated from the second column and the method may further include cutting the third column widthwise to separate each of the RFID electrical inlays of the third column from one another. The method may further include cutting the second column widthwise to separate each of the RFID electrical inlays of the second column from one another.

In some embodiments, prior to cutting the backing sheet along the second cutline, the method may include applying electrically conductive adhesive over the right and left pads of the RFID electrical inlays of the second and third columns. For example, applying the electrically conductive adhesive over the right and left pads of the RFID electrical inlays of the second and third columns may include applying the electrically conductive adhesive as a substantially continuous stripe over the right and left pads of the RFID electrical inlays of the second and third columns.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which:

FIG. 5B is a top plan view of one of the antenna inlays of FIG. 5A;

FIG. 5C is an enlarged top plan view of a portion of FIG. 5B showing two gaps formed in tamper input contact leads of the layer of aluminum where respective resistors are to be attached to the antenna inlay;

FIG. 5D is an enlarged top plan view of a portion of FIG. 5C showing respective resistors attached to the tamper input contact leads across the gaps;

FIG. 6A is a top plan view of an alternative embodiment of one of the antenna inlays of FIG. 5A;

FIG. 6B is an enlarged top plan view of a portion of FIG. 6A showing two gaps formed in tamper input contact leads of the layer of aluminum where respective resistors are to be attached to the antenna inlay;

FIG. 6C is an enlarged top plan view of a portion of FIG. 6B showing respective resistors attached to the tamper input contact leads across the gaps;

FIG. 7A is a top plan view of a second alternative embodiment of one of the antenna inlays of FIG. 5A;

FIG. 7B is an enlarged top plan view of a portion of FIG. 7A showing two gaps formed in tamper input contact leads of the layer of aluminum where respective resistors are to be attached to the antenna inlay;

FIG. 7C is an enlarged top plan view of a portion of FIG. 7B showing respective resistors attached to the tamper input contact leads across the gaps;

FIG. 7D is an enlarged top plan view of a third alternative embodiment of the antenna inlay showing two gaps formed between widened portions provided in tamper input contact leads of the layer of aluminum and showing respective resistors attached to the widened portions;

FIG. 9A is a top plan view of an alternative embodiment backsheet showing the geometry of the electrode traces of the backsheet;

FIG. 14C is a top plan view, similar to FIGS. 14A and 14B, showing the passive RFID tag attached to the electrode traces at a bottom portion of the ladder geometry of the end regions;

FIG. 14D is an enlarged top plan view of an alternative embodiment of a ladder geometry showing rungs being situated at an inclined angle with respect to the elongated sides of the ladder geometry;

FIG. 14E is an enlarged top plan view of an alternative embodiment of a ladder geometry showing rungs being formed by a sinusoidal shaped pattern between the elongated sides of the ladder geometry;

FIG. 26 is a top plan view showing a portion of a film layer carrying six RFID tag circuits, conductive adhesive stripes extending over electrical contact pads of the RFID tag circuits, and substantially sinusoidal cut patterns weaved around the electrical contact pads;

FIG. 27 is a top plan view showing a pair of RFID tag circuits after the substantially sinusoidal cuts shown in FIG. 26 have been made, a set of lateral cuts above and below the respective RFID tag circuits, and a pair of dashed lines indicating that the RFID tag circuits are placed on an optional wider backing layer after the substantially sinusoidal cuts shown in FIG. 26 have been made;

FIG. 28 is a top plan view showing a first alternative embodiment in which a square wave cut pattern is weaved around the electrical contact pads;

FIG. 29 is a top plan view showing a second alternative embodiment in which a triangle wave cut pattern is weaved around the electrical contact pads;

FIG. 30 is a top plan view showing an alternative embodiment in which the conductive adhesive is applied, intermittently, as dashes over the respective electrical contact pads;

DETAILED DESCRIPTION

The following description relates to features of incontinence detection pads that are placed beneath patients on patient support apparatuses such as hospital beds, stretchers, wheelchairs, chairs, and the like. However, the same features may just as well be implemented in other absorbent articles such as incontinence detection garments (e.g., diapers), feminine hygiene products, and the like. Thus, the description below pertains to all types of absorbent articles that absorb and detect biofluids such as urine or blood, for example.

Figure 1:
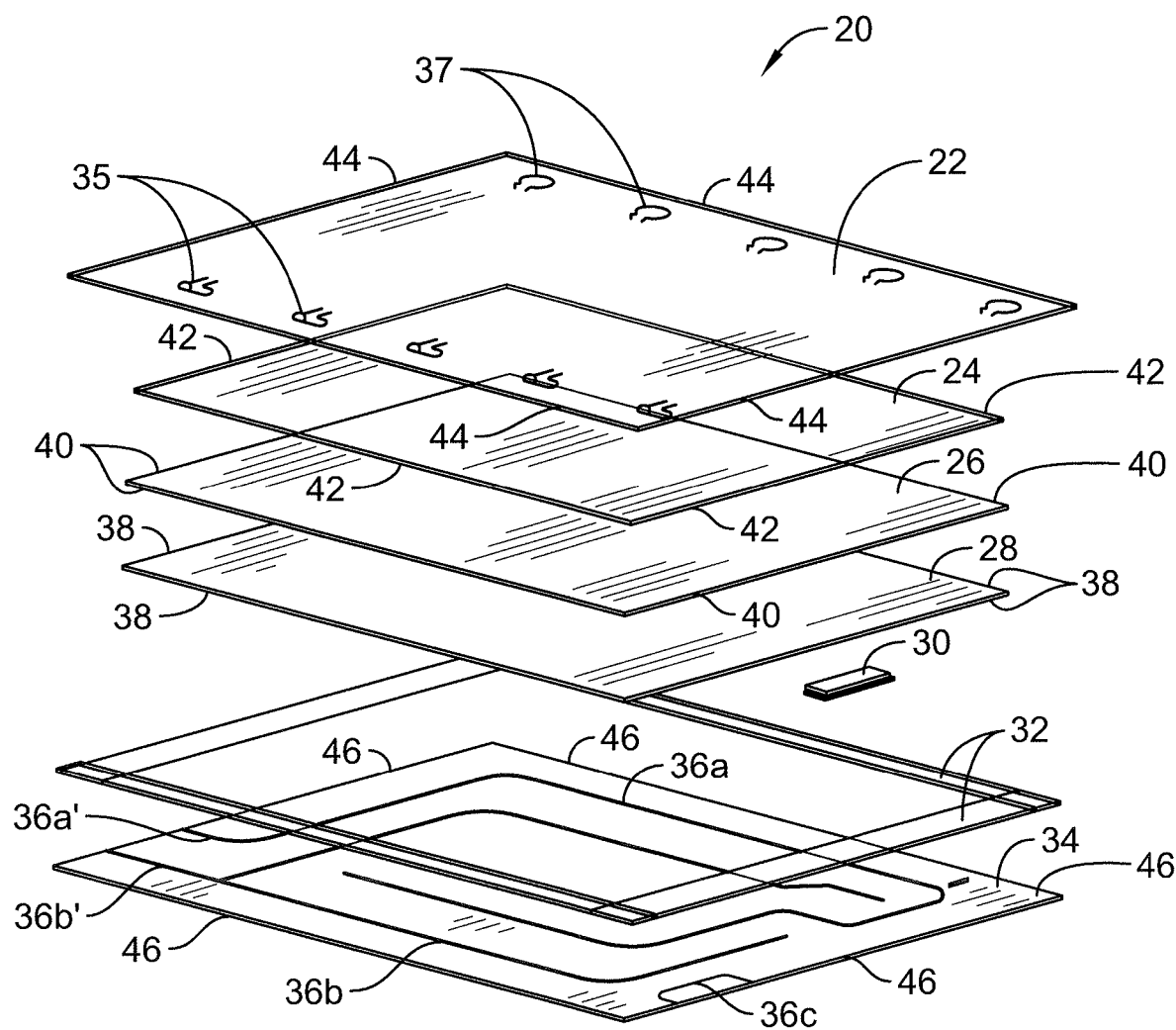
FIG. 1 is an exploded perspective view showing layers of an incontinence detection pad including, from top to bottom, a topsheet of nonwoven material, a layer of slot coated adhesive beneath the topsheet, a moisture absorbent core beneath the layer of adhesive, a low volume filter layer beneath the absorbent core, a passive radio frequency identification (RFID) tag beneath the low volume filter layer, a layer of peripheral hot melt adhesive, and a backsheet having electrodes printed thereon.

As shown in FIG. 1, an incontinence detection pad 20 includes, from top to bottom, a topsheet of nonwoven material 22, a layer of slot coated adhesive 24 beneath the topsheet 22, a moisture absorbent core 26 beneath the layer of adhesive 24, a low volume fluid filter layer 28 beneath the absorbent core 26, a passive radio frequency identification (RFID) tag 30 beneath the low volume fluid filter layer 28, a layer of peripheral hot melt adhesive 32, and a backsheet 34 having first and second electrodes traces 36a, 36b printed thereon. Electrode traces 36a, 36b are sometimes referred to herein as just "electrodes" or just "traces." Elements 22, 24, 26, 30, 32, 34, 36a, 36b are substantially the same as shown and described in International Publication No. WO 2017/087452 A1 which is already incorporated by reference herein. See particularly, FIGS. 31-35 and paragraphs 318-327 of International Publication No. WO 2017/087452 A1, in this regard. Thus, fluid filter layer 28 is an additional element as compared to the incontinence detection pad embodiments shown and described in International Publication No. WO 2017/087452 A1.

Fluid filter layer 28 is configured to inhibit low volumes of fluid from reaching electrodes 36a, 36b and causing RFID tag 30 to emit a false positive signal indicating that an incontinence event has occurred when, in fact, such an event has not occurred. In connection with the illustrative examples contemplated herein in which incontinence detection pad 20 is used primarily for the detection of urinary incontinence, low volumes of fluid are considered to be volumes that are about 40 grams of fluid or less. However, via appropriate selection of materials and geometries for the fluid filter layer 28, other volume thresholds for what is considered to be a low volume of fluid, such as thresholds that are greater than 40 grams or less than 40 grams, are possible according to the teachings of the present disclosure.

As noted above, false positive alerts are sometimes generated due to perspiration or medicinal gels, lotions, or creams leeching through the incontinence detection pad and coming into contact with the electrodes. In such situations the patient's skin may act as part of the electrical pathway between the electrodes in combination with the leeched moisture that contacts the electrodes. As used herein, the term "fluid" is intended to cover all fluid or fluid like substances that may come into contact with incontinence detection pad 20 and complete an electric circuit between electrode traces 36a, 36b, including perspiration, urine, loose feces, lotions, creams, gels, etc. Thus, anything that isn't a dry substance is within the scope of the term "fluid" according to the present disclosure.

Several embodiments are contemplated herein for fluid filter layer 28. In some embodiments, the fluid filter layer 28 includes a hydrophobic polymeric nonwoven material and in other embodiments, the fluid filter layer comprises a hydrophilic material. The hydrophobic polymeric nonwoven material may include, for example, one or more of the following: a spunbond material, a spunlace material, a meltblown material, or a meltspun material. The hydrophobic polymeric nonwoven material may include a polypropylene or polyethylene material having a pore size and basis weight configured to prevent the low volume of fluid from penetrating therethrough due to surface tension of the fluid. For example, in the case of a spunbond nonwoven material, a basis weight in the range of about 2 grams per square meter (gsm) to about 50 gsm may suffice. More particularly, in some embodiments, a basis weight in the range of about 5 gsm to about 20 gsm may suffice. Basis weights above and below these ranges are within the scope of the present disclosure for other embodiments contemplated herein depending upon the desired fluid transfer properties of the fluid filter layer 28 using spunbond nonwoven material.

Figure 13:
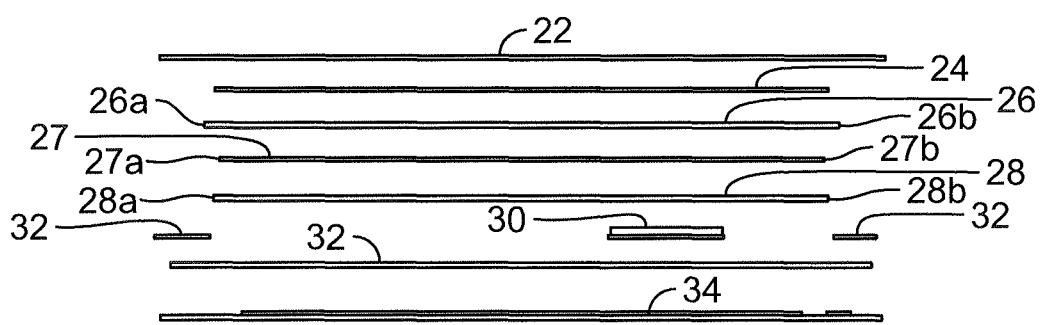
FIG. 13 is an exploded end elevation view of the incontinence detection pad of FIG. 1 showing, from top to bottom, the topsheet of nonwoven material, the adhesive beneath the topsheet, a moisture absorbent core beneath the layer of adhesive, a layer of adhesive beneath the moisture absorbent core, the low volume filter layer beneath the adhesive, the passive RFID tag beneath the low volume filter layer, side and end strips of the layer of peripheral hot melt adhesive, and the backsheet.

Referring now to FIG. 13, an exploded end elevation view of the incontinence detection pad 20 is shown. In the illustrative embodiment, topsheet 22 of pad 20 comprises a polypropylene (PP) spunbond nonwoven layer, adhesive 24 comprises a layer of hot melt adhesive, absorbent core 26 comprises an airlaid material, fluid filter layer 28 comprises an SMS nonwoven barrier layer, and an adhesive layer 27 is provided between core 26 and layer 28 and comprises a sprayed layer of hot melt adhesive. Beneath fluid filter layer 28 in FIG. 13 is the RFID tag 30, the peripheral adhesive 32 at the long sides of pad 20 which comprises a hot melt sprayed adhesive, the peripheral adhesive at one end of the short side of pad 20 which comprises slot coated adhesive, and the backsheet 34.

A suitable topsheet 22 is Berry 0286 material which is a 17 gsm treated PP spunbond material available from Berry Global Inc. of Evansville, Ind. According to this disclosure, a series of foot indicia or graphics 35 and a series of head indicia or graphics 37 is printed near long edges 44 of topsheet 22 as shown in FIG. 1. Further details of such graphics 35, 37 are shown, for example, in FIGS. 59A-62D, 65A-69D, and 70 of International Publication No. WO 2017/087452 A1 which is already incorporated by reference herein. A suitable ink for graphics 35, 37 is Sun Chemical GA0BG00007 Cool Gray 8C Water-Based ink available from Sun Chemical of Parsippany-Troy Hills, N.J.

In some embodiments, adhesive 24, 27, 32 is Full Care 5603 hot melt adhesive available from H.B. Fuller Company of St. Paul, Minn. In some embodiments, layer 24 is a lined, combed, slot coated layer having adhesive applied in rows along the machine direction of topsheet 22 that are about 1 mm wide and that are spaced apart by about 4 mm. Such lined, combed, slot coating of adhesive 24 results in incontinence detection pad 20 having a ribbed or furrowed upper surface texture. The ribbed texture serves to trap any fluid, such as urinary incontinence, on pad 20 and to reduce the chances that the fluid will run off pad 20.

In other embodiments, a different combed, slot coating may be used for layer 24 such as for example, 1 mm glue strips with 1 mm gaps for 50% coverage or 2 mm glue strips with 10 mm gaps for 17% coverage and so on. Peripheral adhesive 32 may be similarly slot coated in any of these manners in some embodiments. In some embodiments, adhesive 32 along the long dimension of pad 20 is spray coated and adhesive 32 along the short dimension of pad 20 is slot coated. In some embodiments, fluid filter layer 28 comprises Berry SM10170UN material which is a 17 gsm hydrophobic SSMMS polypropylene (PP) spunmelt nonwoven material available from Berry Global Inc. of Evansville, Ind. Adhesive 27 between absorbent core 26 and fluid filter layer 28 comprises a randomized, sprayed layer in some embodiments. Absorbent core 26 has a weight of about 135 gsm and comprises Fitesa B871M135S30 airlaid material in some embodiments.

In some embodiments, absorbent core 26 has a width of about 660 mm+/−20 mm between opposite edges 26a, 26b as shown in FIG. 13. Fluid filter layer 28 has a width of about 640 mm+/−10 mm between opposite edges 28a, 28b. Adhesive layer 27 has a width of about 630 mm+/−5 mm between opposite edges 27a, 27b. Layers 27, 28 are centered with respect to the sides 26a, 26b and ends of absorbent core 26. Thus, at the nominal dimensions absorbent core 26 overhangs fluid filter layer 28 by about 10 mm on each side and overhangs layer 27 by about 15 mm on each side. A substantially similar amount of overhang by absorbent core 26 with respect to the ends of layers 27, 28, respectively, is provided in some embodiments.

In some embodiments, the fluid filter layer 28 includes a perforated film. The holes or perforations provided in the perforated film may include one or more of the following: die cut holes, laser cut holes, or holes created by vacuum forming. The perforated film may include one or more of the following types of materials: low density polyethylene (LDPE), high density polyethylene (HDPE), polyethylene terephthalate (PET), or polypropylene. In some alternative embodiments, a conductive ink pattern forming electrode traces 36a, 36b is printed on an underside of the perforated film of the fluid filter layer 28 rather than being printed on an upper surface of the backsheet 34. In such embodiments, the holes of the perforated film are all spaced apart from the conductive ink pattern printed on the underside of the perforated film. In other embodiments having electrode traces 36a, 36b printed on the backsheet 34, as depicted, the holes or perforations of the film are located so as not to overlie any portions of the electrode traces 36a, 36b.

In some embodiments, the fluid filter layer 28 includes an adhesive material applied to a bottom of the absorbent core 26 or to the top surface of the backsheet 34. In some embodiments, such as the embodiment shown in FIGS. 2 and 3, the adhesive material may be applied to the bottom of the absorbent core or to the backsheet so as to match a geometry or pattern of the first and/or second electrode traces 36a, 36b thereby covering the respective first and/or second electrode traces 36a, 36b. Thus, in FIGS. 2 and 3, a fluid filter layer 28a, 28b is provided above both of electrode traces 36a, 36b but in alternative embodiments, only one or the other of fluid filter layers 28a, 28b is provided above the respective electrode trace 36a, 36b.

The adhesive material of fluid filter layer 28a, 28b may include a hot melt adhesive. In some contemplated embodiments, the adhesive material is either spray coated or slot coated on the bottom of the absorbent core or on the top of the backsheet after electrodes 36a, 36b are printed thereon. In other embodiments, fluid filter layer 28a, 28b is made of an adhesive film. In some embodiments, electrodes 36a, 36b have a width of about 1 mm to about 3 mm and the adhesive of layer 28a, 28b has a width about 3 mm to about 25 mm. It is contemplated that the width of adhesive of layer 28a, 28b is wider than the respective electrodes 36a, 36b so as to overhand both sides of electrodes 36a, 36b. A shim of a slot coater used to apply the adhesive in some embodiments has slots that define the width of adhesive layer 28a, 28b.

In some embodiments, the fluid filter layer 28 includes a hydrophobic coating applied to the absorbent core 26. The hydrophobic coating may be applied in one or more of the following patterns: dots, stripes, or random pattern. The hydrophobic coating may be sprayed onto the absorbent core 26 or applied as an adhesive film, for example.

In some embodiments, the fluid filter layer 28 or the fluid filter layer 28a, 28b includes a soluble coating applied over the first and second electrode traces 36a, 36b. For example, the soluble coating may include a water soluble coating and/or a urine soluble coating. In some embodiments, the soluble coating includes a dissolvable ink. The soluble coating is absent from portions of the first and second electrode traces 36a, 36b at which the electrical contacts of the passive RFID tag 30 couple to the first and second electrode traces 36a, 36b.

In some embodiments, the fluid filter layer 28 includes a cellulosic nonwoven material. For example, the cellulosic nonwoven material may include tissue paper. Thus, the cellulosic nonwoven material is akin to a coffee filter, for example.

Figure 2:
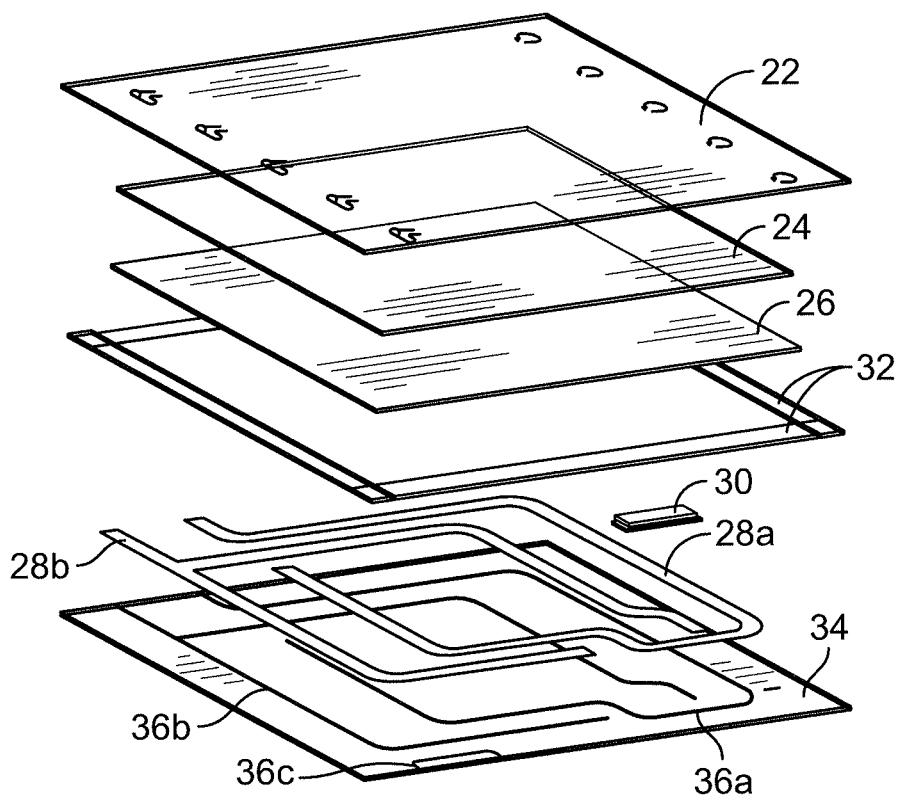
FIG. 2 is an exploded perspective view showing layers of an alternative embodiment of an incontinence detection pad including, from top to bottom, a topsheet of nonwoven material, a layer of slot coated adhesive beneath the topsheet, a moisture absorbent core beneath the layer of adhesive, a layer of peripheral hot melt adhesive, a passive radio frequency identification (RFID) tag beneath the layer of peripheral hot melt adhesive, a low volume filter coating, and a backsheet having electrodes printed thereon, the low volume filter coating being shaped substantially the same as the geometry of the electrodes.
Figure 3:
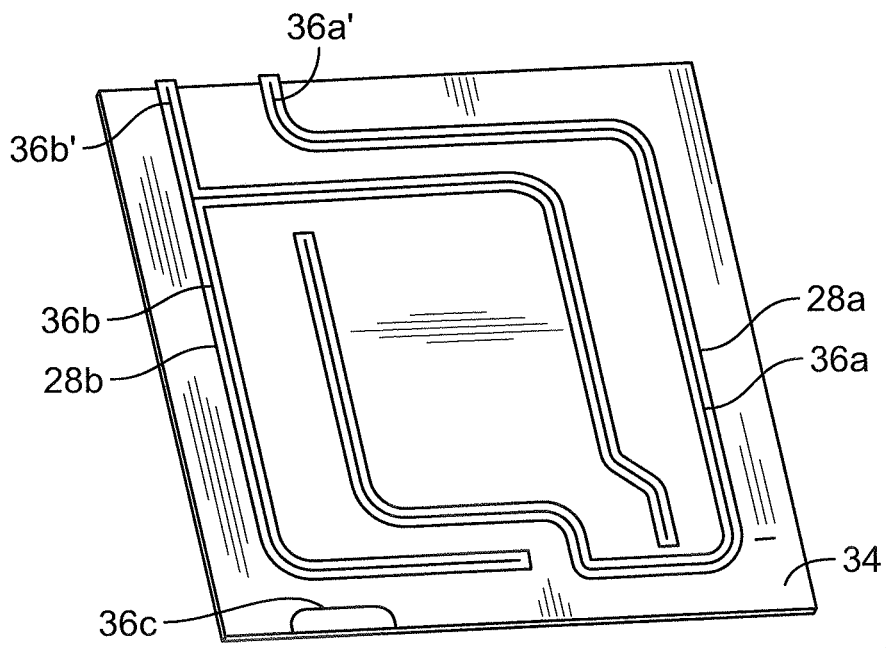
FIG. 3 is a perspective view showing the low volume filter coating situated over the electrodes of the backsheet so as to coat the electrodes.

In the illustrative examples of FIGS. 1-3, the fluid filter layer 28 or the fluid filter layer 28a, 28b, as the case may be, is located beneath the absorbent core 26. However, it is contemplated by this disclosure that, in some embodiments, the fluid filter layer 28 or fluid filter layer 28a, 28b is situated above the absorbent core 26. In such embodiments, the fluid filter layer 28 or fluid filter layer 28a, 28b also may be situated above the topsheet 22. Alternatively, the fluid filter layer 28 or the fluid filter layer 28a, 28b may be situated beneath the topsheet 22 so as to be sandwiched between the topsheet 22 and absorbent core 26, either above or below adhesive layer 24.

In the illustrative example of FIG. 1, each of elements 22, 24, 26, 28, 32, and 34 of the incontinence detection pad 20 is rectangular in shape. Also in the illustrative example of FIG. 1, an outer periphery 38 of the fluid filter layer 28 is coextensive with an outer periphery 40 of the absorbent core 26. Peripheries 38, 40 are also coextensive with an outer periphery 42 of adhesive layer 24 in the illustrative embodiment. In other embodiments, fluid filter layer 28 is larger than depicted so that its outer periphery 38 is coextensive with an outer periphery 44 of the topsheet 22. In such embodiments, periphery 38 of the fluid filter layer 28 is also coextensive with an outer periphery 46 of the backsheet 34. Optionally, the fluid filter layer 28 may be laminated to the absorbent core 26 using one or more of the following: adhesive, heat bonding, or latex bonding.

In some embodiments, the fluid filter layer 28 or the fluid filter layer 28a, 28b may include an adhesive with desiccant media. The adhesive with desiccant media may adhere the topsheet to the absorbent core, for example. A suitable adhesive in this regard may be the FULLCARE™ adhesive available from H. B. Fuller Company of St. Paul, Minn. Alternatively or additionally, the fluid filter layer 28 or the fluid filter layer 28a, 28b may include a desiccant. For example, the desiccant may be sprayed onto the topsheet 22 or the absorbent core 26 or the backsheet 34.

As will be discussed in further detail below in connection with FIGS. 10-12, the adhesive of the fluid filter layer 28 or fluid filter layer 28a, 28b also may be applied so as to cover a sacrificial electrode trace portion 36c that is located above the backsheet 34 in spaced apart relation with the first and second electrodes 36a, 36b. The adhesive also may be applied to portions 36a', 36b' of the first and second electrode traces 36a, 36b that may extend beyond a periphery of the absorbent core.

Figure 4A:
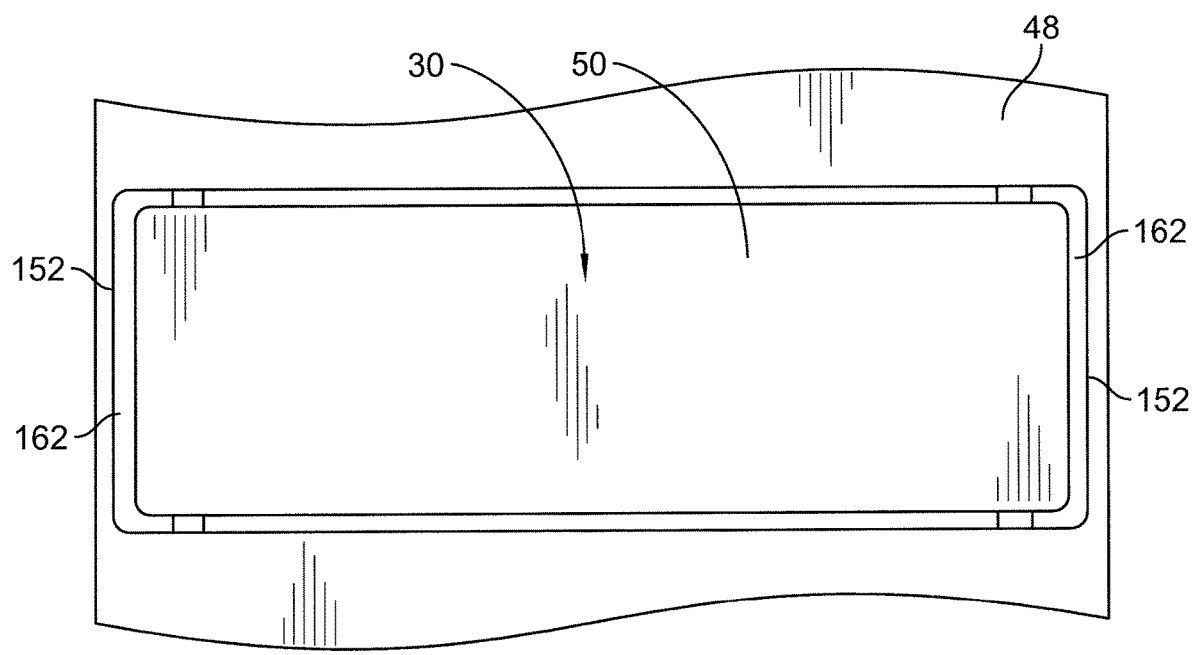
FIG. 4A is a top plan view of the passive RFID tag on a release liner sheet.
Figure 4B:
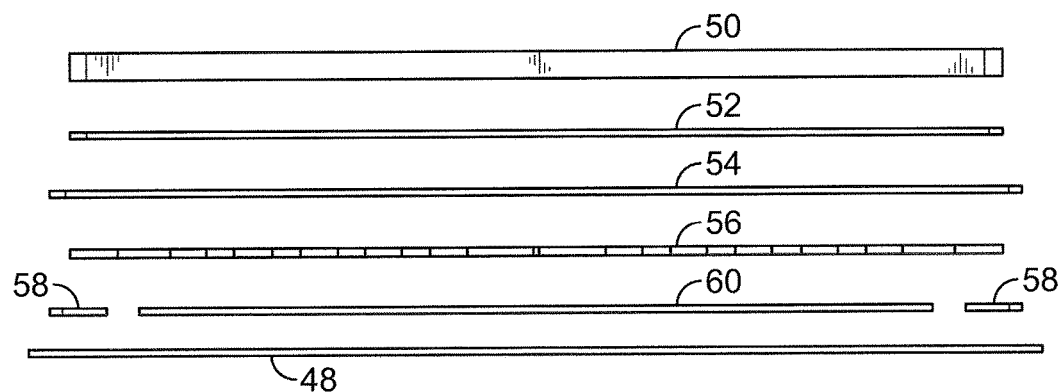
FIG. 4B is an exploded side elevation view of the passive RFID tag and release liner showing, from top to bottom, a foam layer, a foam-to-tag adhesive layer, a conductive adhesive layer, an inlay film, an inlay antenna, a non-conductive adhesive, and the release liner.

Referring now to FIGS. 4A-4D, prior to assembly of the passive RFID tag 30 onto backsheet 34 so as to electrically couple to traces 36a, 36b, tag 30 is situated on a release liner sheet 48. As shown in FIG. 4B, an illustrative embodiment of the passive RFID tag 30 includes, from top to bottom, a foam spacer 50, a foam-to-tag adhesive layer 52, a conductive adhesive layer 54, an inlay film 56, an inlay antenna 58, and a non-conductive adhesive 60. As also shown in FIG. 4B, the release liner 48 is situated beneath inlay antenna 58 and non-conductive adhesive 60. In the illustrative embodiment, release liner 48 comprises a Model No. 17782 L-10 Easy Release Polyethylene Terephthalate (PET) Liner available from Technicote, Inc. of Miamisburg, Ohio. The foam spacer 50 of the illustrative embodiment comprises a Model No. 4 mm Volara 2A XLPE Foam available from Sekisui Voltek, LLC of Coldwater, Mich. The foam-to-tag adhesive 52 and the non-conductive adhesive 60 each comprises 0.0035" L1+DCP adhesive available from 3M of St. Paul, Minn. The conductive adhesive 54 comprises 55 μm 9750 adhesive also available from 3M. Inlay film 56 comprises 50 μm PET film. Inlay antenna 58 comprises 9 μm aluminum.

Figure 4C:
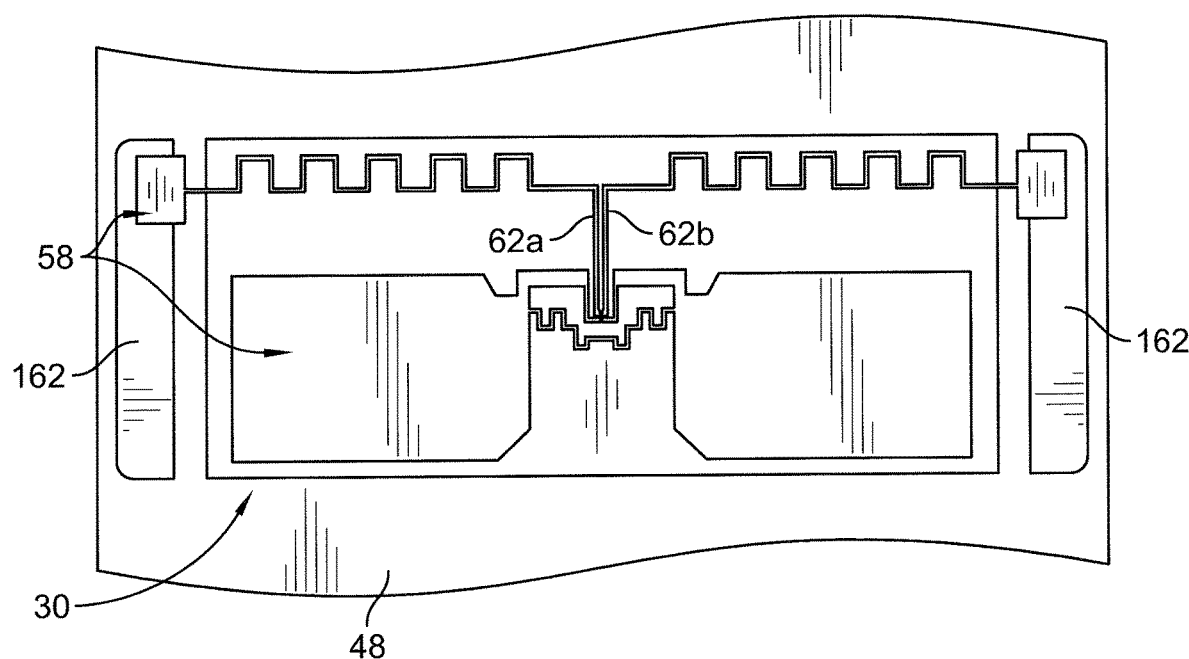
FIG. 4C is a top plan view, similar to FIG. 4A, with the foam layer and foam-to-tag adhesive removed to expose the inlay antenna and electrode-to-tamper-input leads.
Figure 4D:
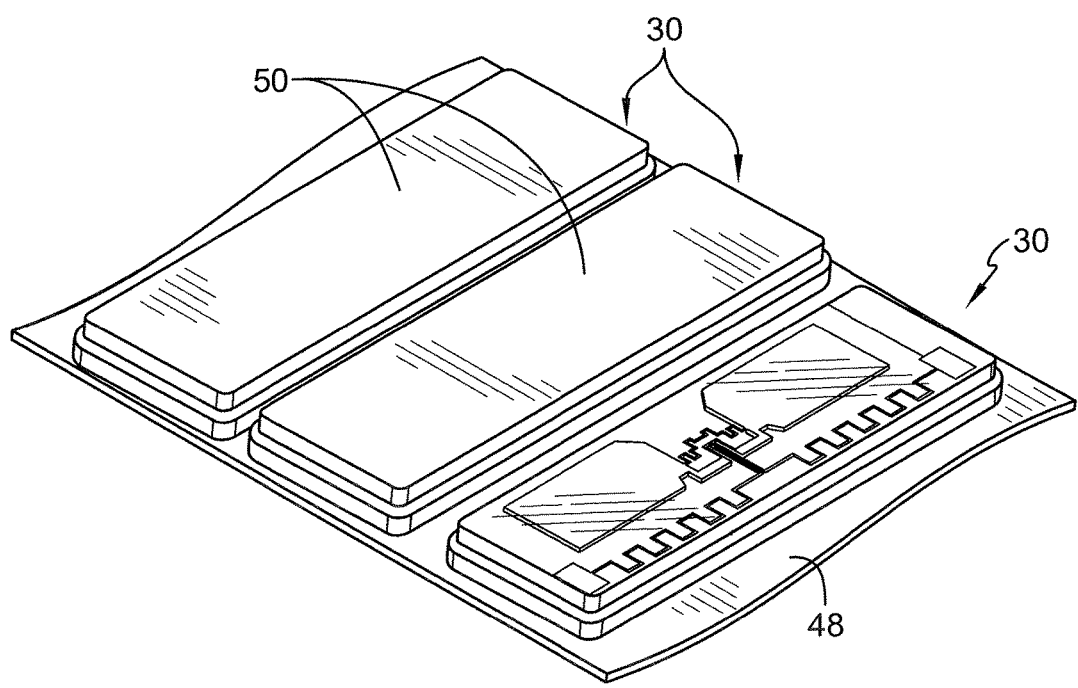
FIG. 4D is a perspective view showing three passive RFID tags on the sheet of underlying release liner.

In FIG. 4C, the foam layer 50 and foam-to-tag adhesive 52 is removed to expose the inlay antenna 58 which includes a first embodiment of electrode-to-tamper-input leads 62a, 62b. In FIG. 4D three passive RFID tags 30 on the sheet of underlying release liner 48 can be seen. The tags 30 are provided on a roll of release liner 48 which is unrolled during the manufacturing process of incontinence detection pads 20. RFID tags 30 and release liner 48 shown in FIGS. 4A-4D are substantially similar to those shown in FIGS. 57 and 58 of International Publication No. WO 2017/087452 A1 and described at paragraphs 336-338 thereof. As noted above International Publication No. WO 2017/087452 A1 is incorporated by reference herein.

Referring now to FIGS. 5A-5D, additional details of one alternative embodiment of an antenna inlay 58 contemplated herein is shown. It has been found that, when RFID tags 30 having antenna inlays 58 like that shown in FIGS. 4A-4C are used, the electromagnetic filed generated from the transmit antenna that powers the RFID tag 30 may induce a current in the tamper input leads 62a, 62b which results in the RFID chip of tag 30 making a false positive reading. That is, the RFID chip sets a tamper bit indicating that the incontinence detection pad 20 is wet when, in fact, it is not wet. Thus, according to the present disclosure, one or more current limiting resistors are provided on the antenna inlay 58 to prevent or reduce the false positives produced by the electromagnetic field emitted by the transmit antenna of an associated reader.

Figure 5A:
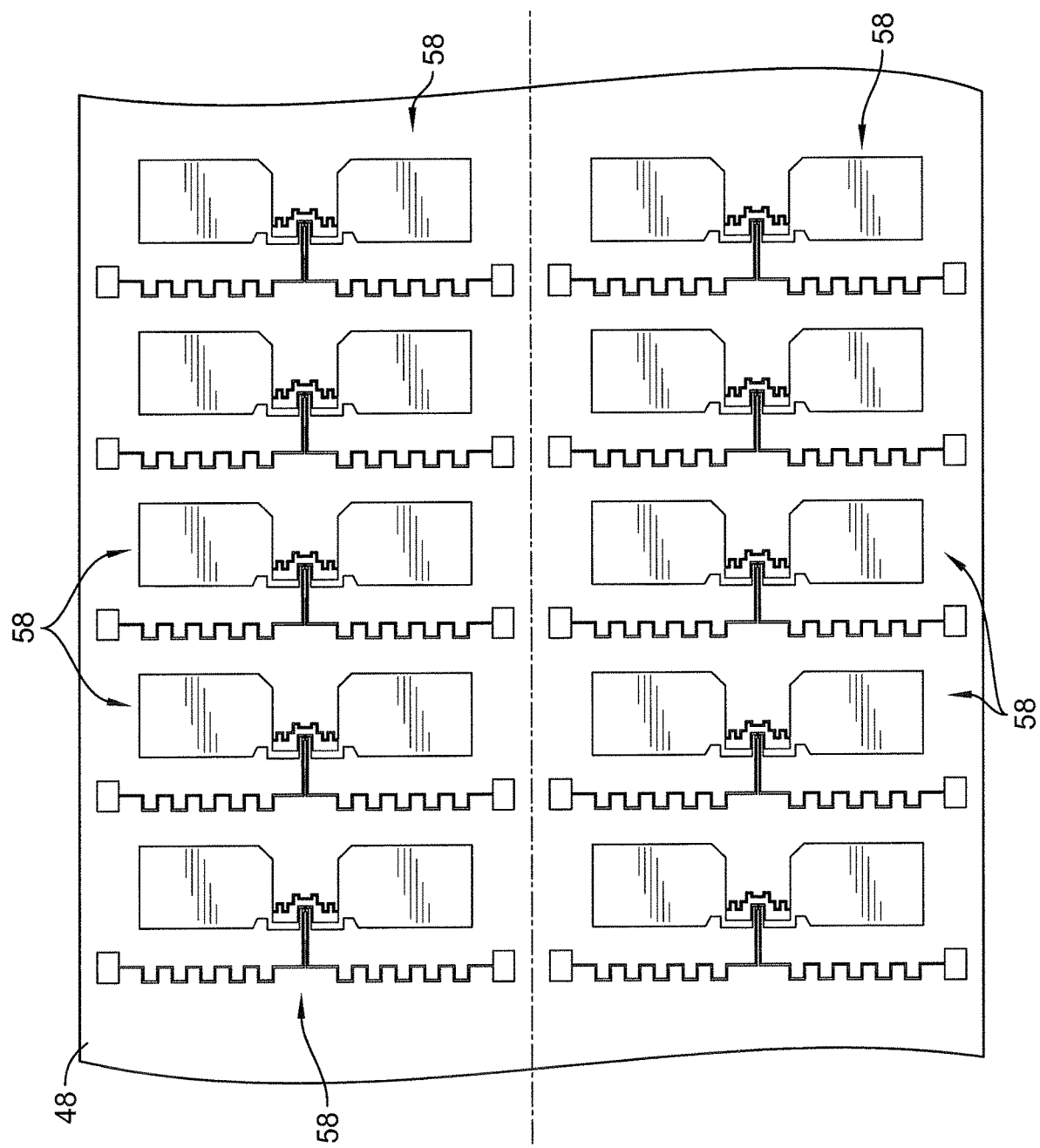
FIG. 5A is a top plan view showing a film layer carrying ten antenna inlays made of aluminum prior to separation from the film layer for installation in the respective RFID tags.

As shown in FIG. 5A, release liner or film layer 48 carries ten antenna inlays 58 made of aluminum prior to installation in the respective RFID tags 30. One of the antenna inlays 58 of the embodiment of FIGS. 5A-5D is shown in FIG. 5B. Inlay 58 includes a pair of large antenna patches 64, a first undulated trace 66 interconnecting patches 64, a first electrical contact 68, a second electrical contact 70, a second undulated trace 72 extending from contact 68 toward contact 70, and a third undulated trace 74 extending from contact 70 toward contact 68. Tamper input leads 62a, 62b extend from respective undulated traces 72, 74 toward undulated trace 66 in spaced parallel relation with each other. Thus, lead 62a, contact 68, and undulated trace 72 form one of the tamper inputs to the RFID chip and lead 62b, contact 70, and undulated trace 74 form the other of the tamper inputs to the RFID chip.

The RFID chip of tag 30 is very small and electrically couples to trace leads 62a, 62b and to antenna patches 64. Suitable RFID chips for use in RFID tags 30 include model nos. G2iL+(SL3S1213FUF or SL3S1213FUD/BG) chips available from NXP Semiconductors N.V. of Eindhoven, Netherlands. In the illustrative example, antenna patches 64 are mirror images of each other and the tamper inputs (one of which comprises elements 62a, 68, 72 and the other of which comprises elements 62b, 70, 74) are mirror images of each other. Elements 62a, 68, 72 and elements 62b, 70, 74 are sometimes referred to herein as electrical contact portions of antenna inlay 58.

As compared to prior art antenna inlays, such as those disclosed in FIG. 57 and described in paragraphs 336-337 of International Publication No. WO 2017/087452 A1 which is already incorporated by reference herein, antenna inlays 58 of the embodiment of FIGS. 5A-5D herein have a gap 76 formed in each lead 62a, 62b, thereby separating first lead 62a into a first lead segment 62a' and a second lead segment 62a" and separating second lead 62b into a third lead segment 64a' and a fourth lead segment 64b" as shown in FIGS. 5C and 5D. In the illustrative example, first and second resistors 78 are attached to leads 62a, 62b such that the first resistor 78 spans the gap 76 of lead 62a thereby electrically coupling lead segment 62a' with lead segment 62a" and such that the second resistor 78 spans the gap 76 of lead 62b thereby electrically coupling lead segment 62b' with lead segment 62b". Thus, in connection with the embodiment of FIGS. 5A-5D, resistors 78 are the current limiting resistors mentioned above. In some embodiments, the first and second resistors 78 both have resistance values of about 2.4MΩ. Suitable resistors 78 in this regard include model no. RC0402FR-0724L 2.4MΩ resistors available from Yageo Corporation of New Taipei City, Taiwan. In other embodiments, however, resistors 78 have resistance values from about 1MΩ to about 2.5MΩ.

Referring now to FIGS. 6A-6C, another alternative embodiment antenna inlay 58 is shown. Antenna inlay 58 of the FIG. 6A-6C embodiment is substantially the same as antenna inlay 58 of the FIG. 5A-5D embodiment except that the location of gaps 76 are different and first and second resistors 80, 82 are used in lieu of resistors 78. Otherwise, the same reference numbers are used in the FIGS. 5A-5D embodiment and the FIGS. 6A-6C embodiment to denote like components. With reference to the orientation of antenna inlay 58 in FIGS. 6A-6C, gaps 76 are provided in horizontal portions of leads 62a, 62b rather than in vertical portions as was the case with the FIGS. 5A-5D embodiment. The location of gaps 76 is shown best in FIG. 6B in this regard. Leads 62a, 62b are upside down L-shaped in the illustrative examples.

The resistance values of resistors 80, 82 are different from each other in some embodiments. In the illustrative example of FIGS. 6A-6C, resistor 80 is a model no. AC0402FR-072ML 2-Mega Ohms 0402 resistor available from Yageo Corporation of New Taipei City, Taiwan and resistor 82 is a model no. RC0402JR-070RL 0-Ohms 0402 resistor also available from Yageo Corporation. Thus, resistor 80 has a resistance of 2MΩ and resistor 82 has a resistance of 0Ω in the illustrative embodiment. In other embodiments, resistors 80, 82 may have resistance values from about 1MΩ to about 2.5MΩ. Thus, according to the present disclosure, only one resistor may be used with antenna inlay 58 to span the respective gap 76 in either lead 62a or lead 62b, as the case may be. In such embodiments, one of leads 62a, 62b may be formed as a continuous lead without any gap 76.

Referring now to FIGS. 7A-7C, yet another alternative embodiment antenna inlay 58 is shown. Antenna inlay 58 of the FIG. 7A-7C embodiment is substantially the same as antenna inlay 58 of the FIG. 5A-5D embodiment except that the location of gaps 76 are different and resistors 84 are used in lieu of resistors 78. Otherwise, the same reference numbers are used in the FIGS. 5A-5D embodiment and the FIG. 7A-7C embodiment to denote like components. With reference to the orientation of antenna inlay 58 in FIGS. 7A-7C, gaps 76 are provided in vertical portions of leads 62a, 62b but are located further upwardly than the gaps 76 of the FIGS. 5A-5D embodiment. The location of gaps 76 is shown best in FIG. 7B in this regard.

The resistance values of both resistors 84 are the same in some embodiments. In the illustrative example of FIGS. 7A-7C, resistor 84 is a model no. ERJ2LW/2BW 0402 resistor available from Panasonic Corporation of Osaka, Japan. Thus, resistors 84 have resistances of 10MΩ in the illustrative example. In other embodiments, resistors 84 may have resistance values from about 1MΩ to about 2.5MΩ. As should be apparent from the embodiments of FIGS. 5A-5D, 6A-6C and 7A-7C, gaps 76 and the respective resistors may be located anywhere along leads 62a, 62b according to the present disclosure.

Referring now to FIG. 7D, yet another alternative embodiment of a portion of antenna inlay 58 is shown. Antenna inlay 58 of the FIG. 7D embodiment is substantially the same as antenna inlay 58 of the FIG. 7A-7C embodiment except that the location of gaps 76 are different and resistors 85, 87 are used in lieu of resistor 84. Otherwise, the same reference numbers are used in the FIGS. 7A-7C embodiment and the FIG. 7D embodiment to denote like components. With reference to the orientation of antenna inlay 58 in FIG. 7D, gaps 76 are provided in vertical portions of leads 62a, 62b but are located further upwardly than the gaps 76 of the FIGS. 7A-7C embodiment. Also, in the FIG. 7D embodiment, extensions 89 are included in trace portions 62a', 62a", 62b', 62b" to provided widened portions of traces 62a, 62b above and below the respective gaps 76. The extensions 89 provide a larger contact area for the electrical contacts of resistors 85, 87 than the embodiments of FIGS. 5A-5D, 6A-6C, and 7A-7C. The extensions 89 of trace portions 62a', 62a" extend in an opposite direction than the extensions 89 of trace portions 62b', 62b". More particular, in the orientation of FIG. 7D, extensions 89 associated with trace portions 62a', 62a" extend to the left and extensions 89 associated with trace portions 62b', 62b" extend to the right.

The resistance value of resistor 85 is different than the resistance value of resistor 87 in some embodiments. In the illustrative example of FIG. 7D, resistor 85 is a 2.4MΩ resistor and resistor 87 is a 1MΩ resistor. Suitable resistors 85 include the model no. RC0402FR-072M4L resistor available from Yageo Corporation of New Taipei City, Taiwan; the model no. RK73H1ETTP2404F resistor available from KOA Corporation of Nagano, Japan; the model no. CRCW04022M40FKED resistor available from Vishay Intertechnology Inc. of Malvern, Pa.; and the model no. CR0402F2M4Q10 resistor available from Ever Ohms Technology Co. Ltd. of Kaohsiung City, Taiwan. Suitable resistors 87 include the model no. RC0402FR-071ML 1MΩ resistor available from Yageo.

The RFID chips used in RFID tags 30 are configured such that sensed resistances between the tamper inputs 62a, 62b that are about 5MΩ to about 6MΩ or less indicate that moisture is present on the incontinence detection pad 20 and is of sufficient volume to be considered an incontinence event. The RFID chips used in RFID tags 30 are also configured such that sensed resistances between the tamper inputs 62a, 62b that are about 20MΩ or more indicates that the incontinence detection pad 20 is considered to be dry. In between these two thresholds is a gray area in which it is uncertain whether the pad 20 is wet or dry. From an alerting standpoint, the pad 20 is still considered to be dry in some embodiments when the resistance between the tamper inputs 62a, 62b is in the gray area between the lower (wet) and upper (dray) resistance thresholds.

The resistors 78, 80, 82, 84, 85, 87 provide isolation for the tamper input pins of the RFID chip connected to leads 62a, 62b from RF energy coupling caused by (a) the proximity of the tamper input lines 62a, 62b to the antenna patches 64 powering the RFID chip of tag 30, and/or (b) the effect of the conductive detection grid (aka electrode traces 36a, 36b) being connected to the tamper inputs. It is also contemplated by this disclosure that a single resistor could be used on a particular input of the RFID chip, such as either on the VDD pin or the Out pin, and achieve the desired isolation from the RF energy. Alternatively, resistors on both of these pins may be used in some embodiments.

Figure 8:
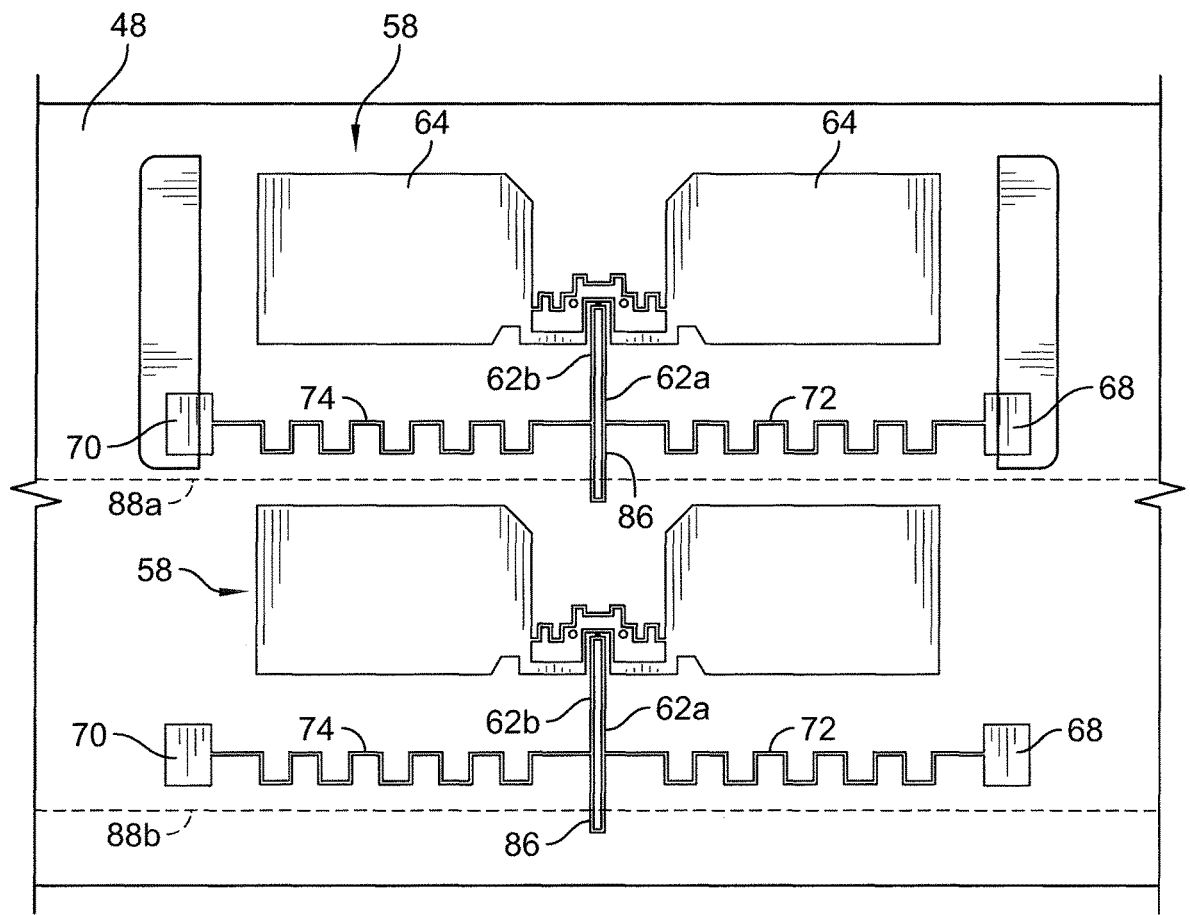
FIG. 8 is a top plan view showing two alternative embodiment antenna inlays on the respective film, each antenna inlay having a sacrificial short formed with the tamper input contact leads so that a test for proper functioning of an RFID chip of the passive RFID tag can be undertaken during manufacture prior to severing of the sacrificial short.

Referring now to FIG. 8, two alternative embodiment antenna inlays 58 on the respective release film 48 each have a sacrificial connecting portion 86 that interconnects the tamper input leads 62a, 62b. The RFID integrated circuit chip has electrical contacts or pins that electrically couple to the leads 62a, 62b of the first antenna inlay (i.e., the upper antenna inlay 58 in FIG. 8) when the RFID integrated circuit chip is attached to the backsheet 48. According to this disclosure, the operation of the RFID chip is tested to confirm that the tamper inputs of the RFID chip, which are coupled to leads 62a, 62b, properly indicate a short circuit prior to installation of the associated RFID tag 30 into an incontinence detection pad 20.

After the RFID chip is attached to the leading inlay 58, energy is emitted to provide the RFID integrated circuit chip with power via the antenna patches 64 of the first antenna inlay 58. A return signal is output by the RFID integrated circuit chip and is transmitted via the antenna patches 64 of the first antenna inlay 58 to the testing equipment which is similar to the readers disclosed in International Publication No. WO 2017/087452 A1 and U.S. application Ser. No. 15/596,036 which are already incorporated by reference herein. See particularly FIGS. 29A-29C of International Publication No. WO 2017/087452 A1 and the related description as well as FIG. 8 of U.S. application Ser. No. 15/596,036 and the related description.

After receiving the return signal, the testing equipment processes the return signal from the RFID integrated circuit chip to confirm that the RFID integrated circuit chip is working properly due to the return signal indicating that the tamper inputs and the respective sacrificial connection portion of the first antenna inlay 58 form a completed short circuit. After the return signal is processed to determine whether the RFID chip passed or failed the test, the release liner 48 is cut at a location indicated by dotted line 88a in FIG. 8. Cutting release liner 48 along dotted line 88a severs at least a part of the sacrificial connecting portion 86 from the pair of leads 62a, 62b of the first antenna inlay 58 to place the leads 62a, 62b of the first antenna inlay 58 in an open circuit configuration and leaving another part of the sacrificial connecting portion 86 behind on a portion of the release liner 48 that is associated with a neighboring antenna inlay 58 (i.e., the antenna inlay 58 at the bottom of FIG. 8). Release liner 48 is sometimes referred to as a "backsheet" herein, even though it is a different element than backsheet 34 of incontinence detection pad 20. Any antenna inlay/RFID chip combinations that fail the test are discarded as scrap. Those that pass the test continue on with the manufacturing process to ultimately be installed on the backsheet 34 of the respective incontinence detection pad 20.

According to the testing procedure just described, each antenna inlay 58 has the sacrificial short 86 formed with the tamper input contact leads 62a, 62b so that a test for proper functioning of an RFID chip of the passive RFID tag 30 can be undertaken during manufacture prior to severing of the sacrificial short. In FIG. 8, a cut line 88b is illustrated in connection with the neighboring antenna inlay 58. It should be understood that third, fourth, fifth and so on antenna inlays 58 follow the antenna inlay 58 beneath the cut line 88b such that the testing operation is carried out in series for each of the antenna inlay/RFID chip combinations. In the illustrative example, the sacrificial connection portions 86 are U-shaped with fairly sharp corners between the vertical and horizontal segments (as viewed in the orientation of FIG. 8). In other embodiments, the sacrificial connection portions 86 may have rounded U-shapes, V-shapes or any other shape that interconnects leads 62a, 62b and passes through the respective cut line, such as illustrative cut lines 88a, 88b.

Referring now to FIG. 9A, an alternative embodiment backsheet 134 is shown having a different geometry or pattern of first and second electrode traces 136a, 136b as compared to the electrode traces 36a, 36b of the backsheet 34 shown in FIGS. 1-3. One of the differences is that trace 136a includes a semicircular trace portion 138 having a radius of about 201.5 mm in the illustrative example. Trace 136a also includes an arcuate trace portion 140 having a radius of about 321.8 mm in the illustrative example. The arcuate trace portion 140 interconnects with one end of the semicircular trace portion 138. Portions 138, 140 arc in opposite directions. Another difference is that sacrificial trace portion 136b' extends at an angle, illustratively 40°, with respect to a long dimension of backsheet 134, whereas portion 36b' on backsheet 34 is oriented parallel with the long dimension of backsheet 34. Other aspects of the patterns of traces 136a, 136b on backsheet can be readily gleaned from a visual inspection of FIG. 9A. Backsheet 134 also has registration marks 141a, 141b that are used during the manufacture of the incontinence detection pad 20 in which backsheet 134 is included.

Still referring to FIG. 9A, the overall length of backsheet 134, and therefore the overall length of the associated pad 20, is about 900 mm and the overall width of backsheet 134, and therefore the overall width of the associated pad 20, is about 750 mm in the illustrative embodiment. Absorbent core 26 is generally centered on backsheet 134 has as a length of about 790 mm and a width of about 660 mm (see the dotted line rectangle in FIG. 9A which represents the footprint of absorbent core 26). Furthermore, angle 900 is about 40 degrees in the illustrative embodiment and angle 902 is about 45 degrees in the illustrative embodiment. Portion 138 of trace 136a has a radius of about 201.5 mm and portion 140 has a radius of about 321.8 mm in the illustrative embodiment as noted above. Also in the illustrative embodiment, portion 139 of trace 136b has a radius of about 201.5 mm and portion 143 of trace 136b has a radius of about 351.5 mm.

Additional dimensions of illustrative backsheet 134 include the following: dimension 904 is about 647.0 mm, dimension 906 is about 443.5 mm, dimension 908 is about 167.8 mm, dimension 910 is about 83.5 mm, dimension 912 is about 127.2 mm, dimension 913 is about 85.5 mm, dimension 914 is about 277.0 mm, dimension 916 is about 110.0 mm, dimension 918 is about 127.0 mm, dimension 920 is about 165 mm, and dimension 922 is about 83.5 mm. It should be appreciated that there is a tolerance range associated with each of the given dimensions. Such tolerance ranges include ranges as high as about +/−4.0 mm and as low as about +/−0.1 mm for the various dimensions and there is also a tolerance range of about +/−0.5 degrees for the angles.

The dimensions given for the illustrative example of FIG. 9A are provided for purposes of comparison such as, for example, dimension 914 is at least twice that of dimension 912 or dimension 918. Also, dimension 914 is at least three times that of dimension 910 or dimension 922. Many other similar comparisons can be made based on each of the given dimensions associated with pad 134 such that each possible comparison is contemplated herein. In the illustrative example, dimension 904 is generally centered along the overall length of backsheet 134. Other information concerning the illustrative backsheet 134, including other dimensions, can be found in FIG. 9A of U.S. Provisional Patent Application 62/551,565 which was filed Aug. 29, 2017 and which is hereby incorporated by reference herein.

Figure 9B:
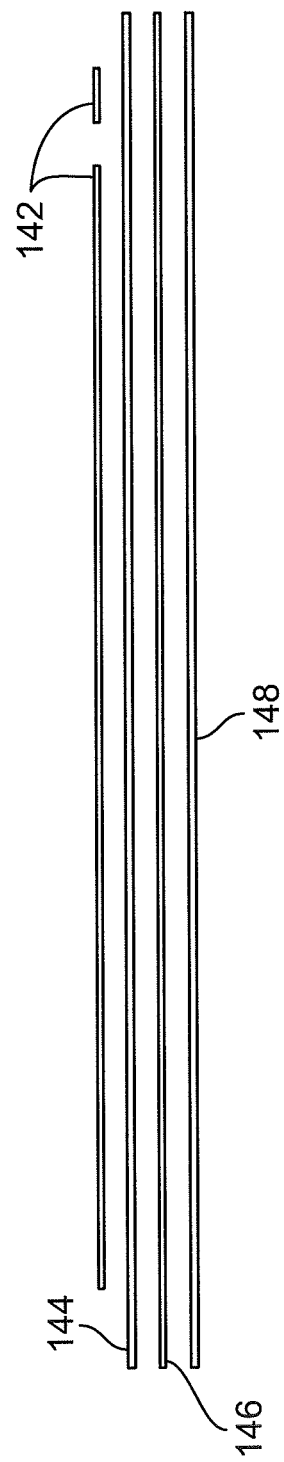
FIG. 9B is an exploded end elevation view of the backsheet of FIG. 9A showing, from top to bottom, the backsheet having carbon conductive ink, a breathable low density polyethylene film, a layer of hot melt adhesive, and a layer of polypropylene spunbond nonwoven material.
Figure 9C:
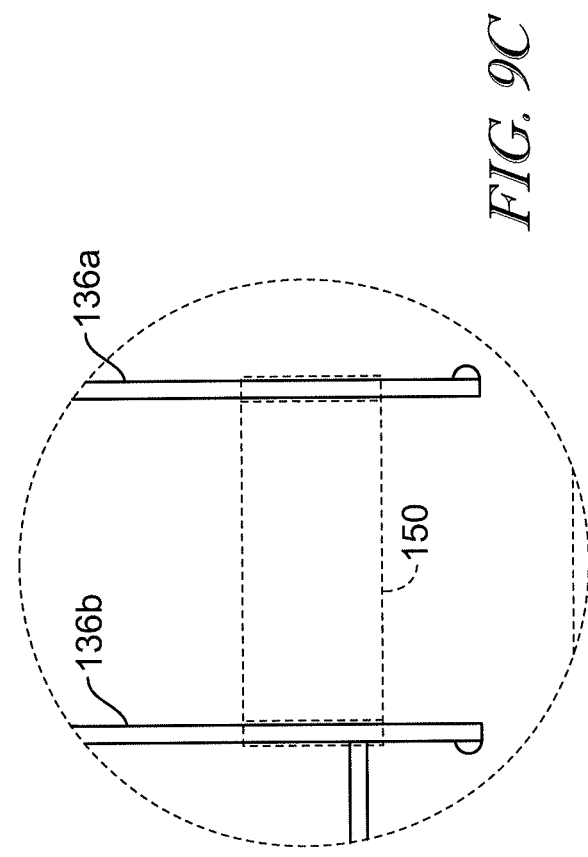
FIG. 9C is an enlarged top plan view of a portion of FIG. 9A showing a tag footprint indicating a location at which the passive RFID tag is attached to the electrodes of the backsheet.

Referring now to FIG. 9B, backsheet 134 includes, from top to bottom, carbon conductive ink 142, a breathable low density polyethylene (LDPE) film 144, a layer of hot melt adhesive 146, and a layer of polypropylene (PP) spunbond nonwoven material 148. An enlarged view of a portion of FIG. 9A is shown in FIG. 9C and depicts a tag footprint 150 indicating a location at which the passive RFID tag 30 is attached to the electrodes 136a, 136b of the backsheet 134.

Figure 10:
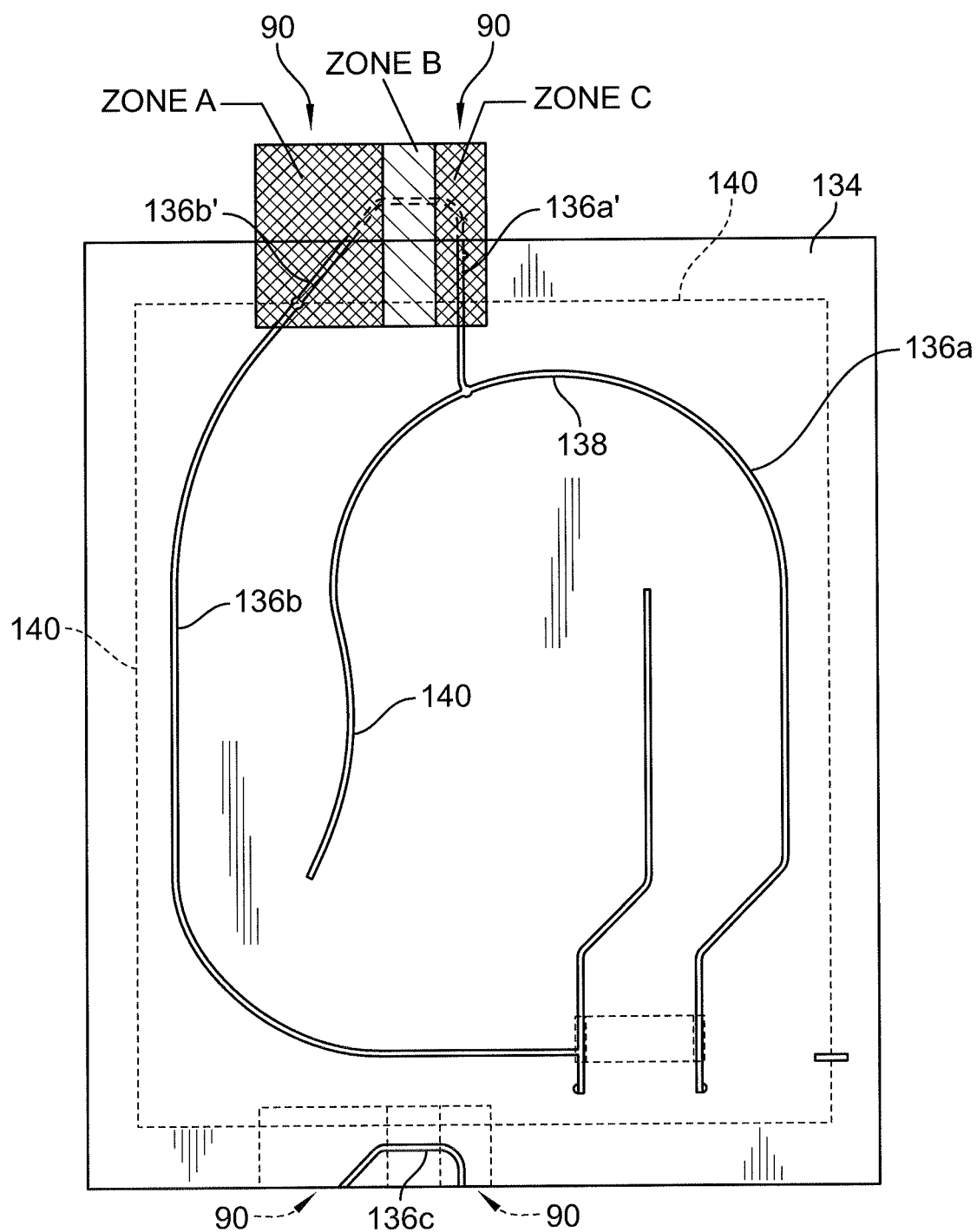
FIG. 10 is a top plan view of the backsheet of FIG. 9A showing a fluid filter layer of adhesive applied over first and second portions of respective first and second electrode traces in a region of the backsheet located substantially outboard of a periphery of an absorbent core which is represented by a dotted rectangle.

Referring now to FIG. 10, backsheet 134 is shown with a fluid barrier layer 90 of adhesive applied over first and second portions 136a', 136b' of respective first and second electrode traces 136a, 136b in a region of the backsheet 134 located substantially outboard of a periphery of an absorbent core (not shown, but substantially the same as absorbent core 26 of FIGS. 1 and 2), the periphery being represented by a dotted rectangle 140 in FIG. 10. The adhesive of barrier layer 90 comprises an extra amount of adhesive as compared to the other portions of the layer of peripheral hot melt adhesive 32 shown in FIGS. 1 and 2, for example. Barrier layer 90 prevents low volumes (or really, any volumes) of moisture from electrically bridging across trace portions 136a', 136b' outboard of periphery 140 which is devoid of any absorbent core material.

Portions 136a', 136b' exist outboard of periphery 140 as a result of the sacrificial trace portion 136c which was once attached to portions 136a', 136b' prior to the preceding backsheet 134 being severed from the illustrative backsheet of FIG. 10 during a manufacturing and testing process of the type described in paragraphs 328-332 in connection with FIG. 36 of International Publication No. WO 2017/087452 A1 which is already incorporated by reference herein. Due to the speed of the manufacturing process, the precise location at which backsheets 134 are severed from each other may vary over time or from backsheet-to-backsheet. Thus, barrier layer 90 is applied to adjacent backsheets 134 so as to assure coverage of trace portions 136a', 136b' regardless of the location at which the backsheets are severed. Accordingly, a small amount of barrier layer 90, on the order of about 10 mm to about 30 mm, extends inboard of periphery 140 in the illustrative embodiment.

As shown in FIG. 10, barrier layer 90 includes zones A and C from among zones A, B and C. The intermediate zone B has an amount of adhesive coverage that is substantially the same as the rest of peripheral adhesive 32. Thus, zone B, technically, is not considered to part of the barrier layer 90. In reality and as will be described in further detail below in connection with FIG. 12, a slot coating process is used to apply the adhesive of barrier layer 90 simultaneously with the application of adhesive of the laterally extending portions of peripheral adhesive 32.

Figure 11:
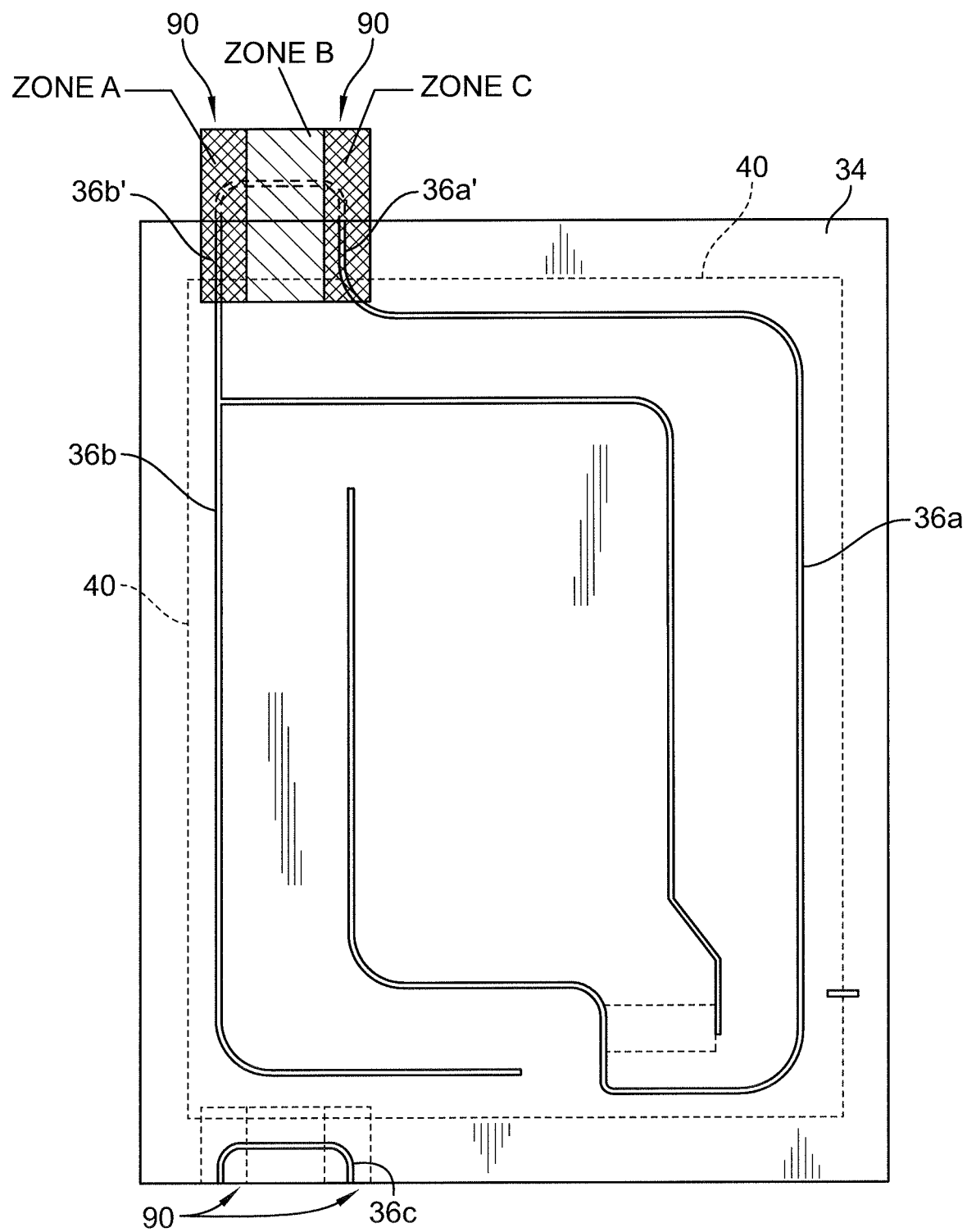
FIG. 11 is a top plan view, similar to FIG. 10, of the backsheet of FIGS. 1-3 showing a fluid filter layer of adhesive applied over first and second portions of respective first and second electrode traces in a region of the backsheet located substantially outboard of a periphery of an absorbent core which is represented by a dotted rectangle.

Referring now to FIG. 11, barrier layer 90 is shown on backsheet 34. The description above of FIG. 10 is, therefore, equally applicable to FIG. 11 except where noted below. That is, fluid barrier layer 90 on backsheet 34 is provided for the same purpose and in substantially the same manner as provided on backsheet 134. The main difference is that trace portion 36b' of backsheet 34 is parallel with the long dimension of backsheet 34 rather than being angled as was the case with backsheet 134. As a result, zone A of barrier layer 90 of backsheet 34 does not need to be as wide as zone A of barrier layer 90 of backsheet 134. In some embodiment, zones A and C of backsheet 34 and zone C of backsheet 134 are about 3 mm to about 25 mm in width. Zone A of backsheet 134 is on the order of about 75 mm to about 100 mm in width.

Figure 12:
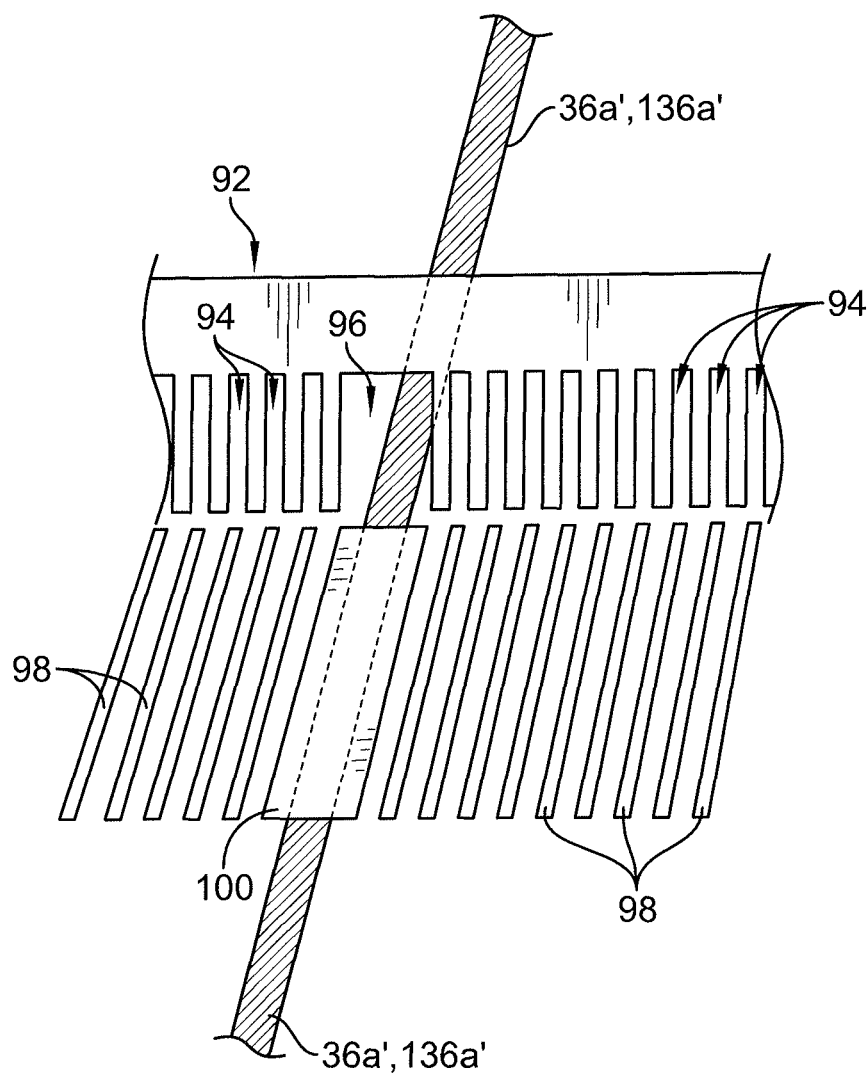
FIG. 12 is a perspective view of a portion of a slot coater shim having a first set of openings of narrow width and a second opening having a width that is wider than the narrow width, the second opening being in registry with a portion of a respective electrode trace.

Referring now to FIG. 12, a portion of a slot coater shim 92 having a first set of openings 94 of narrow width and a second opening 96 having a width that is wider than the narrow width 94. In some embodiments, openings 94 are sized so that stripes of adhesive or glue 98 have a width of about 1 mm and opening 96 is sized to that a strip of glue or adhesive 100 has a width of about 3 mm to about 25 mm. Opening 96 is in registry with portion 36a' of respective electrode trace 36a, or portion 136a' of respective electrode trace 136a, as the case may be. Thus, stripe of glue 100 covers electrode trace portions 36a', 136a'. In the illustrative embodiment, trace portions 36a', 136a' are centered within stripe of glue 100. It should be understood that, in connection with angled trace portion 136b', slot coater shim 92 has another opening (not shown) that is wider than opening 96 but otherwise substantially similar to opening 96. The wider opening is configured so that a stripe of glue or adhesive having a width of about 75 mm to about 100 mm is provided on backsheet 134 over trace portion 136b'. In the case of trace portion 36b', slot coater shim 92 includes another slot 96 in registry with trace portion 36b'. In an alternative embodiment, slot coater shim 92 as a single large opening that results in barrier layer 90 spanning the entirety of zones A, B and C shown in FIGS. 10 and 11.

Referring now to FIGS. 14A-18, several examples of different alternative geometries at the end regions of traces 136a, 136b of incontinence detection pad 20 are shown. These same geometries may just as well be included in the incontinence detection pad 20 having traces 36a, 36b. In some contemplated embodiments, backsheet 34 and backsheet 134 each include a thin, flexible, stretchable, polyethylene film laminated to a polypropylene spunbond nonwoven material. In such embodiments, the RFID tag 30 has a substrate that includes a thin, yet rigid polyethylene terephthalate (PET) film adhered to the backsheet 34, 134 using a double-sided conductive nonwoven scrim adhesive.

When adhered together and stretched, the printed PE film backsheet 34, 134 can stretch while the PET of the RFID tag 30 does not. Due to this disparity in tensile properties, conductive trace breaks have been observed at the intersection point of the printed trace and RFID tag 30 in the embodiments of backsheets 34, 134 like those shown in FIGS. 10 and 11 because RFID tag 30 completely overlaps the respective traces 36a, 36b, 136a, 136b such that opposite ends 152 of RFID tag 30 each lie outboard of the respective portion of trace 36a, 36b, 136a, 136b to which it is coupled. Such breaks at the intersection between RFID tag 30 and traces 36a, 36b, 136a, 136b typically results in a loss of one or more legs (e.g., portions of traces 36a, 36b, 136a, 136b beyond the break and spaced from the RFID tag 30) of the circuit, reducing the ability of pad 20 to detect incontinence in the respective broken leg segment.

The alternative trace geometries at the end regions of traces 136a, 136b shown in FIGS. 14A-18 are improved printed trace designs that result in redundant (e.g., 4 to 5, or even more in some embodiments) contact points to the RFID tag 30 on each side, per electrode 136a, 136b, as opposed to the designs of FIGS. 10 and 11 which have single contact points. Thus, there are multiple electrical pathways to the RFID tag 30 from the main portions of traces 136a, 136b that lead up to the end region geometries. The main portions of traces 136a, 136b are considered to be all portions of traces 136a, 138 that are not part of the redundancy means of the traces 136a, 136b. Such end region geometries of traces 136a, 136b shown in FIGS. 14A-18 are within the scope of the term "redundancy means" as used in the claims of the present application. These disclosed geometries of FIGS. 14A-18 improve the robustness of the pad 20 under severe stress such as may occur during patient repositioning or other handling.

Figure 14A:
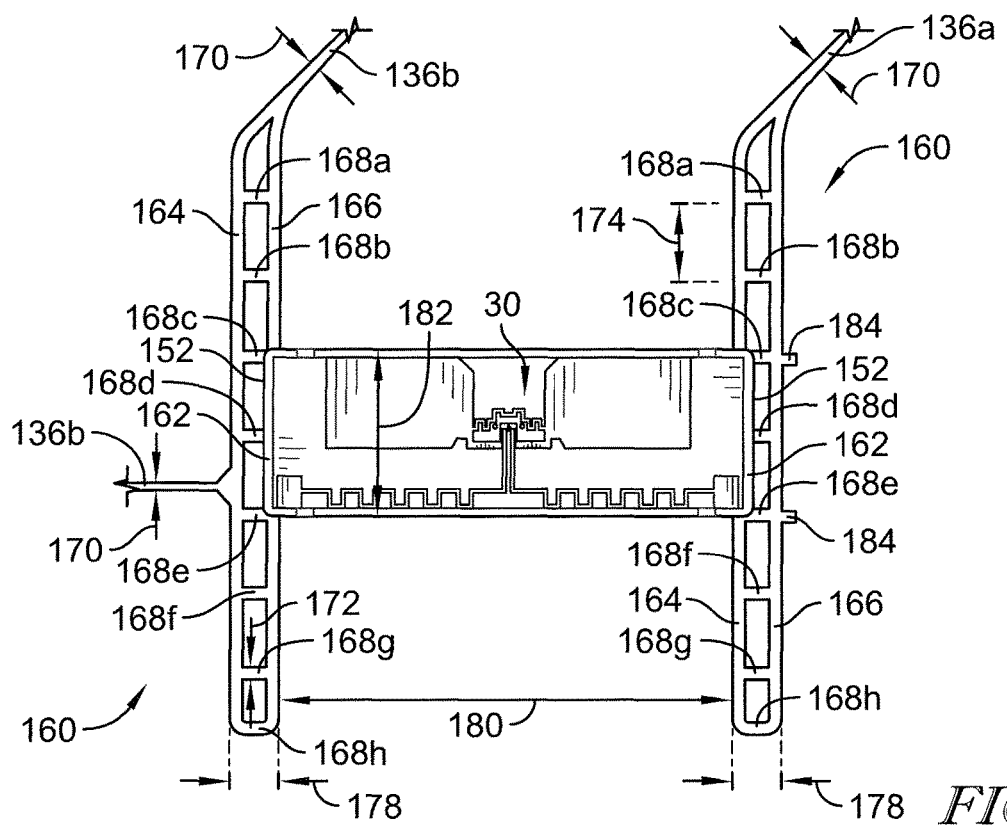
FIG. 14A is a top plan view of an alternative embodiment of electrode trace geometry on a portion of a backsheet where the passive RFID tag couples to the electrode traces showing end regions of the electrode traces each having a "ladder" geometry with a series of rungs interconnecting respective pairs of elongated sides and showing the passive RFID tag attached to the electrode traces about midway between the top and the bottom of the ladder geometry of the end regions.
Figure 14B:
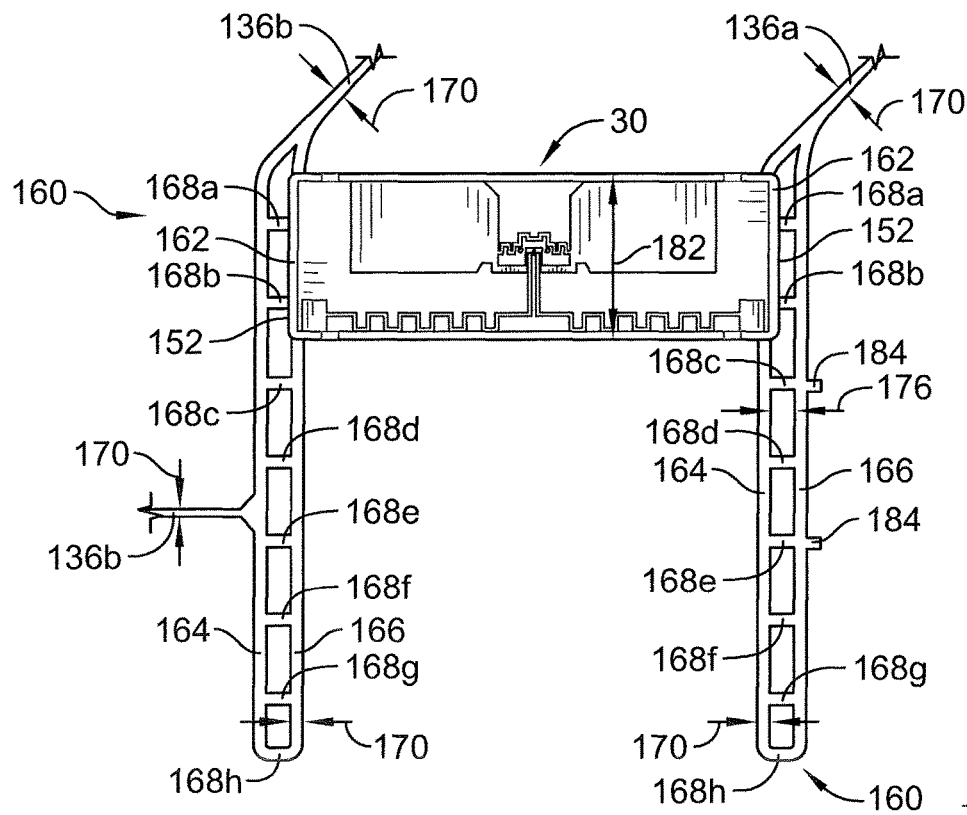
FIG. 14B is a top plan view, similar to FIG. 14A, showing the passive RFID tag attached to the electrode traces at a top portion of the ladder geometry of the end regions.

Referring now to FIGS. 14A-14C, the first and second electrode traces 136a, 136b each includes a redundancy means 160 for coupling to the electrical contacts 162 of the passive RFID tag 30 to provide redundant electrical pathways between the first and second electrode traces 136a, 136b and the electrical contacts 162. Redundancy means 160 of FIGS. 14A-14C comprise portions of the first and second traces 136a, 136b that each has a ladder geometry. The ladder geometry of each of the first and second traces 136a, 136b includes first and second elongated sides 164, 166 and a series of rungs 168a-168b that interconnects the respective elongated sides 164, 166. At the upper ends of redundancy means 160, as oriented in FIGS. 14A-14C, each of the elongated sides 164, 166 merges into the respective main portion of corresponding electrode traces 136a, 136b as the case may be.

All of the rungs 168a-168h of redundancy means 160 are substantially perpendicular to the elongated sides 164, 166 in the illustrative embodiment of FIG. 14A-14C. In other embodiments, some or all of the rungs are not perpendicular to the elongated sides 164, 166 such that the rungs each extend between the elongated sides at an inclined angle as shown in FIG. 14D, for example, in which three exemplary rungs 168a', 168b', 168c' are shown at an inclined angle on a portion of an alternative redundancy means 160' at the end region of electrode 136b. The other rungs (not shown) of the redundancy means 160' of FIG. 14D are similarly inclined.

In the illustrative example, a width 170 of the main portions of traces 136a, 136b is about 3 mm. Elongated sides 164, 166 of ladder geometries 160 have the same width 170 of about 3 mm as main portions of traces 136a, 136b in some embodiments. Further illustratively, a width 172 of each rung 168a-168h is about 2.6 mm. A spacing 174 between a bottom of any particular rung 168a-168f and a bottom of the next adjacent rung 168b-168g therebelow is about 19.5 mm in the illustrative example. This same spacing 174 is about 19.5 mm if measured between centers of the rungs or from tops of the rungs. The spacing between like portions (e.g., bottoms or tops or centers) of rungs 168g and 168h is less than 19.5 in the illustrative example.

A spacing 176 between an inner edge of elongated side 164 and an inner edge of the associated elongated side 166 is about 7.0 mm in the illustrative embodiment. Thus, a spacing 178 between an outer edge of elongated side 164 and an outer edge of the associated elongated side 166 is about 13.0 mm in the illustrative example (i.e., 3 mm width 170 of elongated side 164+7.0 mm spacing 176 in the gap between sides 164, 166+3 mm width 170 of elongated side 166 +/− the various tolerances above or below these dimensions). Thus, spacing 178 is at least three times width 170 of portions of the first and second traces 136a, 136b that are spaced from the ladder geometries 160. In fact in the illustrative example, spacing 178 of 13.0 mm is more than four times width 170 of 3 mm.

A spacing 180, shown in FIG. 14A, between inboard edges of elongated sides 164, 166 of the redundancy means 160 is about 110.0 mm in the illustrative example. The inboard edges of sides 164, 166 are considered to be the sides closest to the center of RFID tag 30. The spacing between opposite ends 152 of RFID tag 30 is about 120 mm. Thus, opposite end regions of the passive RFID tag 30 each overlie respective portions of one of the elongated sides 164, 166 of each of the pair of elongated sides 164, 166 of each ladder geometry 160. In the orientation shown in FIGS. 14A-14C, the left end region of tag 30 overlies a portion of elongated side 166 of the left hand ladder geometry 160 and the right end region of tag 30 overlies a portion of elongated side 164 of the right hand ladder geometry 160. Such an arrangement result in the other elongated sides 164, 166 of the pair of elongated sides 164, 166 of each ladder geometry 160 being situated outboard of the respective end 52 of the passive RFID tag 30. More particularly in the orientation shown in FIGS. 14A-14C, elongated side 164 of the left hand ladder geometry 160 is outboard of the left end 152 of tag 30 and elongated side 166 of the right hand ladder geometry 160 is outboard of the right end 52 of tag 30. By placing tag 30 relative to ladder geometries 160 in this manner, the electrical contacts 162 of tag 30 each overlie a respective one of elongated sides 164, 166.

In FIG. 14A, tag 30 is situated about midway between the top and bottom of the redundancy means 160. In FIG. 14B, tag 30 is situated close to the very top of the redundancy means 160. In FIG. 14C, tag 30 is situated at the bottom of the redundancy means. Thus, the ladder geometries 160 have an overall length that is at least three times a width 182 of RFID tag 30. In the illustrative example, width 182 is about 42 mm and therefore, the overall length of ladder geometries 160 is at least about 126 mm. In the illustrative example, ladder geometries are about 150 mm in length. To provide a visual indication of where tag 30 should be placed in its preferred position midway between the top and bottom of ladder geometries 160, rungs 168c, 168e each have projections 184 extending outwardly from elongated side 166 of the right hand ladder geometry by about 5.0 mm. Projections 184 serve as first and second registration marks that are aligned with respective rungs 168c, 168e to indicate a mid-region of the length of the ladder geometry 160 at which the passive RFID tag 30 is aligned when attached to the substrate 134.

When tag 30 is attached to redundancy means 160 about midway between the top and bottom thereof as shown in FIG. 14A, portions of electrical contacts 162 of passive RFID tag 30 overlap portions of rungs 168c, 168d, 168e on the right side and left side of tag 30, a portion of elongated side 166 at the left side of tag 30, and a portion of elongated side 164 at the right side of tag. Thus, there are five points of contact between each electrical contact 162 of tag 30 at the left and right sides of tag 30 and redundancy means 160 in the FIG. 14A example. These points of contact are included as part of redundant electrical paths from the main portions of traces 136a, 136b and the electrical contacts 162 of tag 30. Thus, if a crack or break develops at any of these points of contact, there are other electrical paths for current to flow to or from electrical contacts 162 of tag 30 as the case may be. Only if all of the points of contact break between the redundancy means 160 and one or the other of electrical contacts 162 will the passive RFID tag 30 be unable to read a closed circuit resulting from wetness bridging between traces 136a, 136b.

When tag 30 is attached to the top region of the redundancy means 160 as shown in FIG. 14B, portions of electrical contacts 162 of passive RFID tag 30 overlap portions of rungs 168a, 168b on the right side and left side of tag 30, a portion of elongated side 166 at the left side of tag 30, and a portion of elongated side 164 at the right side of tag. Thus, there are four points of contact between each electrical contact 162 of tag 30 at the left and right sides of tag 30 and redundancy means 160 in the FIG. 14B example. Similarly, when tag 30 is attached to the bottom region of the redundancy means 160 as shown in FIG. 14C, portions of electrical contacts 162 of passive RFID tag 30 overlap portions of rungs 168f, 168g on the right side and left side of tag 30, a portion of elongated side 166 at the left side of tag 30, and a portion of elongated side 164 at the right side of tag. One might consider the bottoms of electrical contacts 162 to be overlapping portions of rungs 168h in addition to or in lieu of overlapping the bottom end of respective elongated sides 164, 166, as the case may be. In either case, there are four points of contact between each electrical contact 162 of tag 30 at the left and right sides of tag 30 and redundancy means 160 in the FIG. 14C example. Thus, there are redundant electrical paths from the main portions of traces 136a, 136b and the electrical contacts 162 of tag 30 in the FIGS. 14B and 14C examples as well.

Referring now to FIG. 14D, an alternative embodiment redundancy means 160' is shown. Redundancy means 160' is substantially similar to redundancy means 160 and so only a portion of redundancy means 160' is shown. The description above of redundancy means 160 is equally applicable to redundancy means 160' unless specifically noted otherwise. The difference between redundancy means 160' and redundancy means 160 is that the rungs of the ladder geometry are inclined at a non-perpendicular angle to the elongated sides 164, 166. In the illustrative example, rungs 168a', 168b', 168c' are shown but other rungs of redundancy means 160' are similarly inclined including the bottom rung in some embodiments. In a variant embodiment, all rungs except for the bottom rung are inclined and the bottom rung is substantially perpendicular to elongated sides 164, 166 like rung 168h in the embodiment of FIGS. 14A-14C. Also in the illustrative example, angle 188 is about 30 degrees, but angle 188 may be greater or lesser than 30 degrees (e.g., 5 degrees to 85 degrees or even more or less than these numbers) in other embodiments.

In the illustrative example of FIG. 14D, rungs 168a', 168b' and 168c' incline upwardly from left elongated side 164 to right elongated side 166. It is contemplated that the other rungs of redundancy means 160' are similarly inclined. In a variant embodiment, rungs 168a', 168b', 168c', etc. are inclined in the opposite direction. That is, in the variant embodiment, rungs 168a', 168b', 168c', etc. incline upwardly from right elongated side 166 to left elongated side 164. In still another variant, alternating rungs 168a', 168b', 168c', etc. are inclined upwardly and downwardly, one after the other, between elongated sides 164, 166. FIG. 14D shows the redundancy means 160' associated with electrode 136b. It should be understood that the redundancy means 160' associated with electrode 136a is similarly shaped.

In still another variant embodiment, shown in FIG. 14E, the rungs of a redundancy means 160" are formed by a sinusoidal shaped pattern of conductive material provided in the space between elongated sides 164, 166. In FIG. 14E, rungs 168a", 168b", 168c", 168d", 168e" formed by the sinusoidal shaped pattern can be seen. Additional rungs are formed in a similar manner. The bottom rung, like rung 168h of FIGS. 14A-14C, can either be a horizontal segment or a segment of the sinusoidal shaped pattern. FIG. 14E shows the redundancy means 160" associated with electrode 136b. It should be understood that the redundancy means 160" associated with electrode 136a is similarly shaped.

Figure 14F:
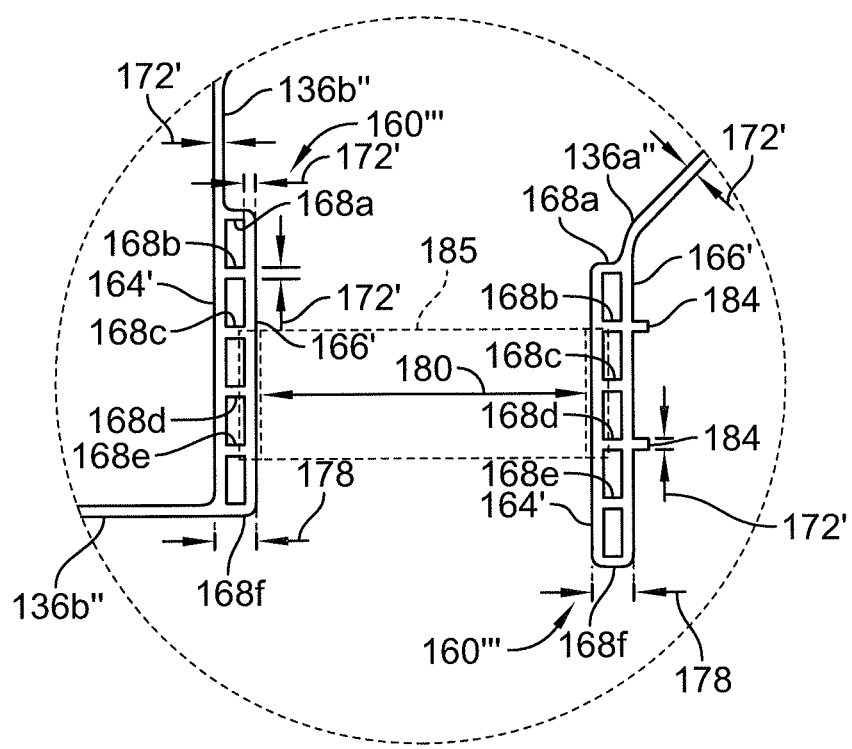
FIG. 14F is an enlarged top plan view, similar to FIG. 14A, showing the ladder geometries at the end regions of the first and second electrode traces being offset generally vertically in the depicted orientation such that the upper and lower ends of the ladder geometries of the first and second electrode traces are not aligned horizontally.

Referring now to FIG. 14F, another embodiment of a redundancy means 160''' is shown. Redundancy means 160''' is substantially similar to redundancy means 160 and so the description above of redundancy means 160 is equally applicable to redundancy means 160''' unless specifically noted otherwise. Redundancy means 160''' is located at end regions of first and second electrode traces 136a", 136b" which are shown in more detail in FIG. 25 which is discussed below. Like the previous redundancy means embodiments described herein, redundancy means 160''' is configured for coupling to the electrical contacts 162 of the passive RFID tag 30 to provide redundant electrical pathways between the first and second electrode traces 136a", 136b" and the electrical contacts 162.

Redundancy means 160''' of FIG. 14F each has a ladder geometry but without as many rungs as redundancy means 160. More particularly, ladder geometry of each of the first and second traces 136a", 136b" includes first and second elongated sides 164', 166' and a series of rungs 168a-168f that interconnects the respective elongated sides 164', 166'. Elongated side 166' of electrode trace 136a" is basically an extension of the main portion of electrode trace 136a" with each rung 168a-168f projecting therefrom to the left in a substantially perpendicular manner as shown in FIG. 14F. Each rung 168a-168f of electrode trace 136a" terminates at the respective elongated side 164'. Similarly, elongated side 164' of electrode trace 136b" is basically an extensions of the main portion of electrode trace 136b" with each rung 168a-168f projecting therefrom to the right in a substantially perpendicular manner as shown in FIG. 14F. Each rung 168a-168f of electrode trace 136b" terminates at the respective elongated side 166'.

A tag footprint 185 is shown in FIG. 14F (in phantom) to indicate the location at which tag 30 is preferably placed when mounted to the substrate on which electrodes 136a", 136b" are printed. The tag footprint 185 is about 42 mm wide and about 120 mm long to match the dimensions of tag 30. To provide a visual indication of where tag 30 should be placed in its preferred position roughly in a central region between the top and bottom of ladder geometries of redundancy means 160''', a pair of projections 184 extend outwardly from elongated side 166' of the right hand ladder geometry by about 5.0 mm. Projections 184 serve as first and second registration marks that are slightly misaligned from respective rungs 168b, 168d to indicate a mid-region of the length of the ladder geometry 160''' at which the passive RFID tag 30 should be aligned when attached to the substrate having electrodes 136a", 136b". In the illustrative embodiment of FIG. 14F, a thickness 172' of electrodes 136a", 136b", elongated sides 164' 166', rungs 168a-168f, and projections 184 is each about 3.0 mm.

Another key difference between redundancy means 160 and redundancy means 160''' is that ladder geometry at the end region of electrode trace 136a" is offset along its length relative to the ladder geometry at the end region of electrode trace 136b". As is apparent in FIG. 14F, the ladder geometries of traces 136a", 136b" are parallel to each other and are of substantially equivalent length. In the illustrative example, the spacing between adjacent rungs 168a-168f is about 16.5 mm. The offset between the ladder geometries is also about 16.5 mm in the illustrative example. Thus, rung 168a of the ladder geometry of electrode trace 136a" is generally aligned with rung 168b of the ladder geometry of electrode trace 136b" and rung 168e of the ladder geometry of electrode trace 136a" is generally aligned with rung 168f of the ladder geometry of electrode trace 136b". In other words, the opposite ends of the ladder geometries, defined by rungs 168a and 168f, are misaligned.

Figure 15:
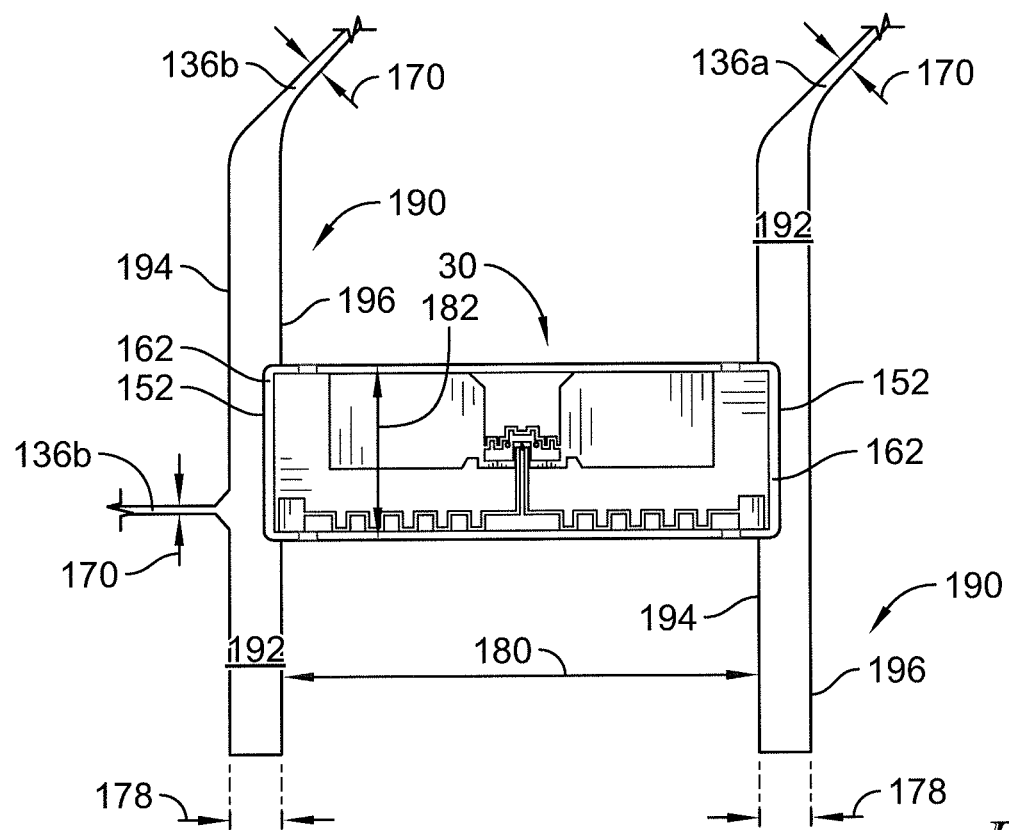
FIG. 15 is a top plan view of another alternative embodiment of electrode trace geometry on a portion of a backsheet where the passive RFID tag couples to the electrode traces showing end regions of the electrode traces each being larger in width as compared to other portions of the electrode traces and showing the passive RFID tag coupled to the larger end regions of the electrode traces.

Referring now to FIG. 15, redundancy means 190 is shown in which end regions 192 of electrode traces 136a, 136b are formed as elongated solid conductive ink regions or strips. Opposite ends 162 of passive RFID tag 30 terminate within the end regions 192 such that portions of the end regions 192 extend outwardly beyond the opposite ends 152 of the passive RFID tag 30. In the illustrative example, the end regions 192 of the first and second electrode traces 136a, 136b are generally straight and are each defined along the majority of their length by a generally straight first side edge 194 and a generally straight second side edge 196 which is parallel with the first side edge 194. The opposite ends 152 of the passive RFID tag 30 are also generally straight. When tag 30 is attached to backsheet 134 having redundancy means 190, the opposite ends 152 of the passive RFID tag 30 are generally parallel with the end regions 192, or more particularly, are generally parallel with edges 194, 196 of end regions 192.

In the illustrative example of FIG. 15, the end regions 192 each have a length that is at least three times the width dimension 182 of the passive RFID tag 30. For example, redundancy means 190 has a length that is similar to that of redundancy means 160 in some embodiments. Thus, the overall length of end regions 192 is at least about 126 mm and, in the illustrative example, is about 150 mm in length. Furthermore, dimensions 170, 178, 180 shown in FIG. 15 are substantially the same as these same dimensions shown in FIG. 14A. Thus, in FIG. 15, dimension 170 is about 3 mm, dimension 178 is about 13.0 mm, and dimension 180 is about 110.0 mm. As noted above, the length dimension of tag 30 between opposite ends 152 is about 120.0 mm. Thus, end regions 192 are configured so that solid conductive ink is outboard of opposite ends 152 of tag 30 when tag 30 is mounted properly to backsheet 134 as shown in FIG. 15. Tag 30 can be mounted closer to a top region or closer to a bottom region of redundancy means 190 if desired.

There are practically an unlimited or infinite number of electrical flow paths between the main portions of electrode traces 136a, 136b and the electrical contacts 162 at the opposite ends 152 of tag 30. Thus, there are only a couple scenarios at the redundancy means 190 in which the passive RFID tag 30 will be unable to read a closed circuit resulting from wetness bridging between traces 136a, 136b. One is if a break or crack totally severs end regions 190 from edge 194 to edge 196 at a location between the segments 136a, 136b and the respective electrical contact 162 of tag 30. Another is if a break or crack forms along or near the complete perimeter of the portion of tag 30 that overlaps one or the other (or both) of regions 192 of redundancy means 190 at the interface between electrical contacts 162 and regions 192.

Figure 16:
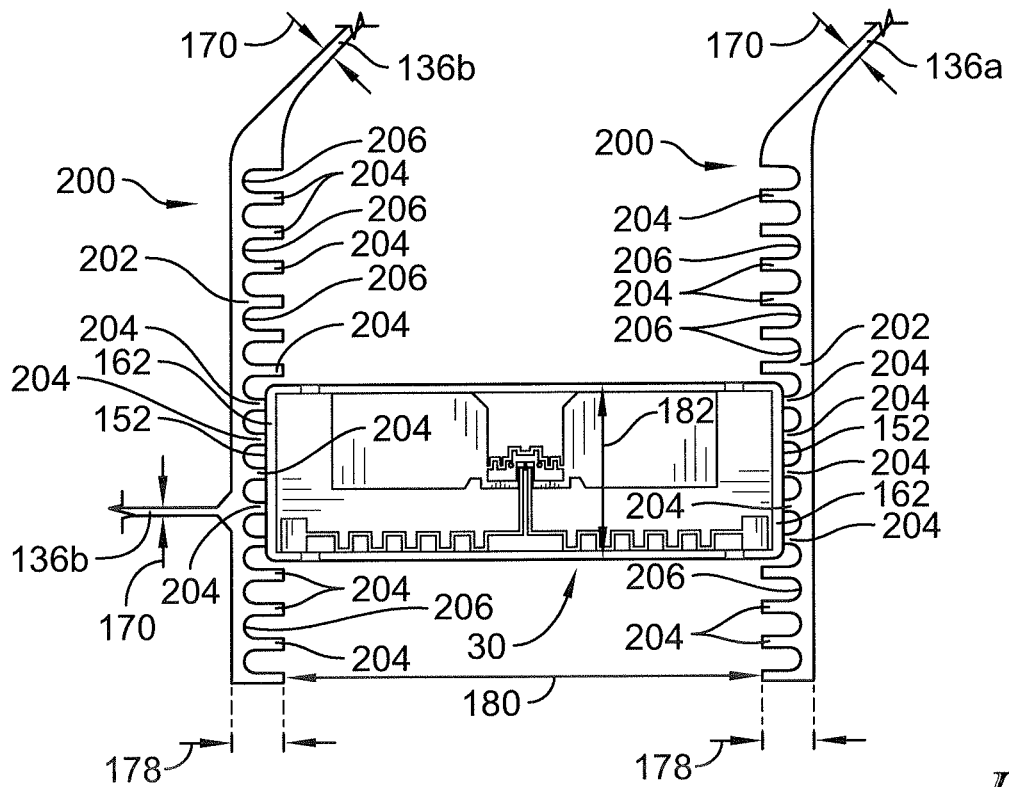
FIG. 16 is a top plan view of a further alternative embodiment of electrode trace geometry on a portion of a backsheet where the passive RFID tag couples to the electrode traces showing end regions of the electrode traces each having a "comb pattern" geometry with a series of teeth extending from a respective elongated side and showing the passive RFID tag attached to the comb pattern geometry of the end regions.

Referring now to FIG. 16, redundancy means 200 is shown in which portions of the first and second electrode traces 136a, 136b are each configured to have a comb pattern. Each comb pattern of the redundancy means 200 includes an elongated side or spine 202 and a series of teeth 204 extending from the respective elongated side 202. If the illustrative embodiment, the teeth 204 of each comb pattern extend in substantially perpendicular relation with the respective elongated side 200. Furthermore, dimensions 170, 178, 180, 182 shown in FIG. 16 are substantially the same as these same dimensions shown in FIG. 14A. Thus, in FIG. 16, dimension 170 is about 3 mm, dimension 178 is about 13.0 mm, dimension 180 is about 110.0 mm, and dimension 182 is about 42 mm.

The teeth 204 of the comb pattern of the portion of the first electrode trace 136a and the teeth 204 of the comb pattern of the portion of the second electrode trace 136b extend toward each other. In the illustrative embodiment, redundancy means 200 has semicircular troughs 206 between teeth 204 in between the locations at which teeth 204 merge with spine 202. In other embodiments, troughs 206 have a shape other than semicircular, such as being square shaped, V-shaped, etc. Opposite ends 152 of the passive RFID tag 30 each may overlie a plurality of teeth 204 of the respective comb pattern. However, the elongated sides 202 of each comb pattern are located outboard of the respective ends 152 of the RFID tag 30 as shown in FIG. 16.

In the illustrative embodiment, electrical contacts 162 at the opposite ends 152 of tag 30 each overlap five of teeth 204. Thus, there are five electrical paths from main portions of electrodes 136a, 136b to the respective electrical contacts 162 of tag 30 in the illustrative example of FIG. 16. If desired, tag 30 can be attached to redundancy means 200 closer to the top or bottom thereof and electrical contacts 162 will each overlap five teeth 204 assuming the tag 30 is not positioned too far below the bottom-most tooth 204 or too far above the top-most tooth 2004. In the illustrative example, each comb pattern of redundancy means 200 has a length that is at least three times width dimension 182 of the passive RFID tag 30.

Figure 17:
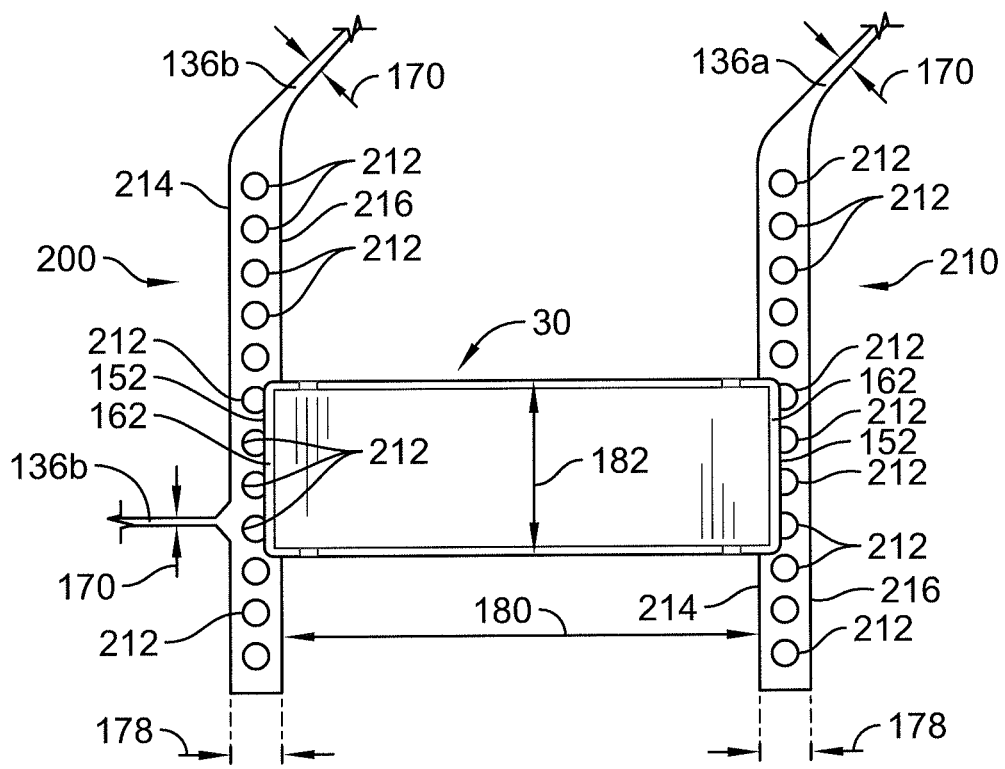
FIG. 17 is a top plan view of yet another alternative embodiment of electrode trace geometry, similar to the embodiment of FIG. 15, on a portion of a backsheet where the passive RFID tag couples to the electrode traces showing end regions of the electrode traces each having a series of holes therein and showing the passive RFID tag attached to the electrode traces at the end regions.

Referring now FIG. 17, redundancy means 210 is shown in which each of the end regions of electrodes 136a, 136b are substantially straight and have a series of circular holes 212 that are aligned along the length of the straight end regions of the redundancy means 210. In the illustrative example of FIG. 17, each end region of redundancy means 210 has a first elongated straight edge 214 and a second elongated straight edge 216 and each circular hole 212 is located about midway between the first and second elongated straight edges 214, 216 of the respective end region. Furthermore, dimensions 170, 178, 180, 182 shown in FIG. 17 are substantially the same as these same dimensions shown in FIG. 14A. Thus, in FIG. 17, dimension 170 is about 3 mm, dimension 178 is about 13.0 mm, dimension 180 is about 110.0 mm, and dimension 182 is about 42 mm.

Opposite ends 152 of the passive RFID tag 30 each overlie a portion of a plurality of the circular holes 212 of each series of circular holes 212 of the respective end region and a portion of each end region is outboard of the respective end 152 of the passive RFID tag 30. Thus, the conductive ink between the holes 212 over which ends 152 of tag 30 are positioned are included in redundant electrical paths to electrical contacts 162 of tag 30. In the illustrative example, ends 152 of tag 30 each overlie four holes 212. In the illustrative example, redundancy means 210 has a length that is at least three times width 182 of tag 30. Thus, tag 30 can be coupled to redundancy means 210 above and below the position shown in FIG. 17.

Based on the above discussion, it is apparent that redundancy means 160, 160', 210 each include enlarged end regions of electrode traces 136a, 136b that have a series of holes through the conductive ink forming the respective end region such that the substrate, such as backsheet 134, is exposed through the series of holes. With regard to redundancy means 160, 160', at least some of holes of the series of holes of the end regions are substantially quadrilateral in shape. For example, the substantially quadrilateral shape of redundancy means 160 is substantially rectangular between the adjacent rungs 168a-168h. In a variant embodiment, the substantially quadrilateral shape of holes of a redundancy means includes holes that are substantially square. In the case of redundancy means 160', the substantially quadrilateral shape between the rungs is substantially rhomboid. The term "rhomboid" herein is intended to cover a rhombus having sides of substantially equal length and rhomboids having sides of unequal length. In the case of redundancy means 210, the holes 212 of the series of holes 212 are each substantially circular in shape.

By providing redundancy means 160, 160', 210 with holes along the respective lengths thereof, less conductive ink is used to print the respective redundancy means 160, 160', 210 as compared to redundancy means 190 of FIG. 15 which does not include any holes of any shape along it length. This represents a cost savings for redundancy means 160, 160', 210 as compared to redundancy means 190. However, the tradeoff is that there are less electrical paths between main portions of electrode traces 136a, 136b and electrical contacts 162 of tag 30 used with redundancy means 160, 160', 210 as compared to redundancy means 190.

This disclosure also contemplates embodiments of redundancy means having holes of other shapes. In some such embodiments, each of the end regions of traces 136a, 136b are substantially straight and the series of holes, of whatever shape, of each end region are aligned with each other along the length of the respective end region. For example, each end regions may be substantially straight with each end region having a first elongated straight edge (e.g., edge 214) and a second elongated straight edge (e.g., edge 216) and each hole of the series of holes may be located about midway between the first and second elongated straight edges of the respective end region. In some embodiments, the end regions may be at least three times wider than main portions of the first and second electrode traces 136a, 136b that are spaced from the end regions. For example, in the illustrative embodiments of redundancy means 160, 160', 210, dimension 178 is at least three times dimension 170. In fact, in connection with redundancy means 160, 160', 210, the end regions of electrode traces 136a, 136b are at least four times wider than the main portions of the first and second electrode traces 136a, 136b that are spaced from the end regions.

Regardless of the shape of the holes provided in the redundancy means, opposite ends 152 of the passive RFID tag 30 each overlie a portion of a plurality of such holes of each series of holes of the respective end region and a portion of each end region is outboard of the respective end 152 of the passive RFID tag 30. In the illustrative examples, the end regions of the first and second electrode traces 136a, 136b are generally straight and the opposite ends 152 of the passive RFID tag 30 are generally straight, such that the opposite ends 152 of the passive RFID tag 30 are generally parallel with the end regions. In the illustrative examples, the end regions each may have a length that is at least three times the width dimension 182 of the passive RFID tag 30. In other embodiments, the end portions are less than three times the width 182 of tag 30 or more than four times the width of tag 30.

Figure 18:
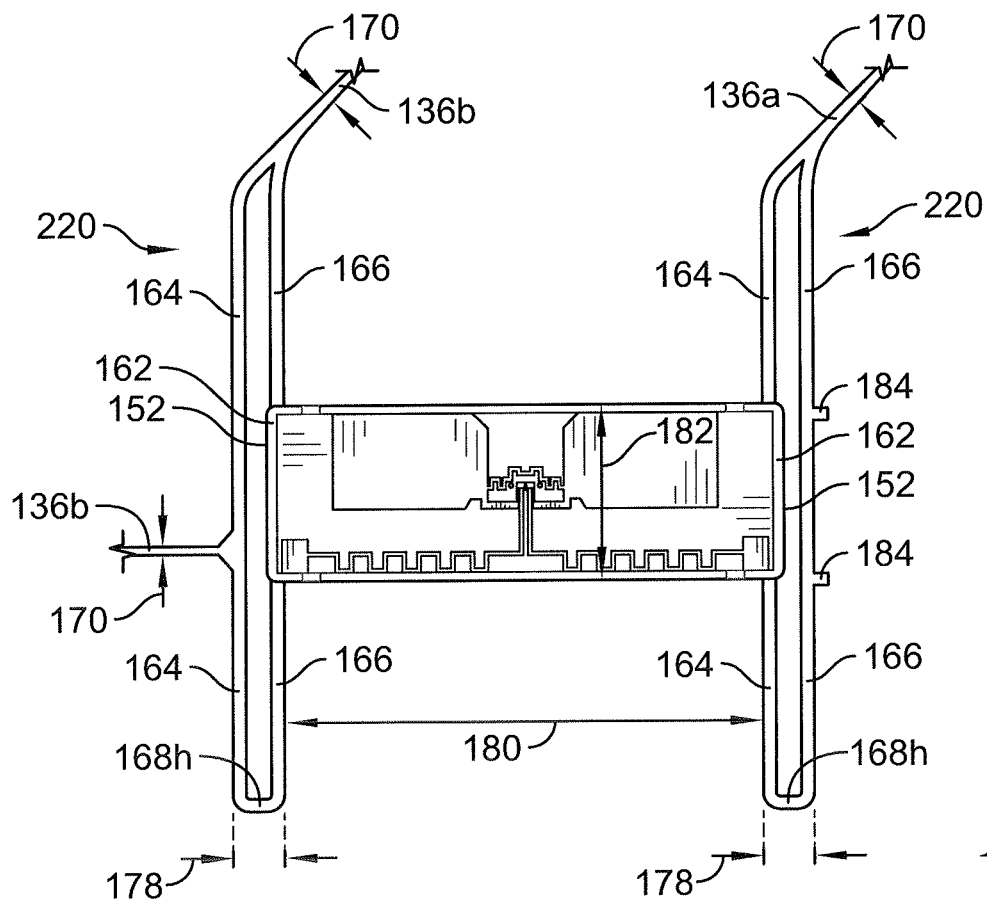
FIG. 18 is a top plan view of still another alternative embodiment of electrode trace geometry, similar to the embodiment of FIG. 14A-14C, on a portion of a backsheet where the passive RFID tag couples to the electrode traces showing end regions of the electrode traces each having elongated loops and showing the passive RFID tag attached to inner segments of the elongated loop of the electrode traces at the end regions.

Referring now to FIG. 18, redundancy means 220 includes portions of the first and second traces 136a, 136b that are each configured as an elongated loop. Each elongated loop of redundancy means 220 is basically the same as the ladder geometry of redundancy means 160 but with rungs 168a-168g omitted. Thus, similar reference numbers are used in FIG. 18 for portions of redundancy means 220 that are substantially the same as like portions of redundancy means 160 of FIGS. 14A-14C. Illustratively, the elongated loops of redundancy means 220 each include a first elongated segment 164, a second elongated segment 166 that is substantially parallel with the first elongated segment 164, and an end segment 168h that interconnects lower ends of the first and second elongated segments 164, 166 in the orientation shown in FIG. 18.

Upper ends of segments 164, 166 of the elongated loops, as oriented in FIG. 18, merge gradually into main portions of electrode traces 136a, 136b. In the illustrative example, opposite ends 152 of the passive RFID tag 30 are located over respective spaces between corresponding first and second elongated segments 164, 166 of the associated elongated loop. In the illustrative example, each of the opposite ends 152 of the passive RFID tag are straight and substantially parallel with the first and second elongated segments 164, 166 of the elongated loops. In some embodiments, each of the first, second, and end segments 164, 166, 168h has a width of a first dimension thereacross and portions of the first and second electrode traces spaced from the elongated loops also may have widths substantially equal to the first dimension thereacross. The first dimension is about 2.6 mm to about 3.0 mm in some embodiments, for example.

In the illustrative example, the elongated loops of redundancy means 220 each have two points of contact with the respective electrical contact 162 of tag 30. Specifically, segment 166 has two points of contact with the left electrical contact 162 of tag 30 and segment 164 has two points of contact with the right electrical contact 162 of tag 30, as oriented in FIG. 18. Thus, if the upper portion of segment 166 of the left elongated loop breaks or cracks, an electrical pathway from the main portion of electrode 136b to the left electrical contact 162 of tag 30 still exists along segment 164, end segment 168h, and the bottom portion of segment 166. Similarly, if the upper portion of segment 164 of the right elongated loop breaks or cracks, an electrical pathway from the main portion of electrode 136a to the right electrical contact 162 of tag 30 still exists along segment 166, end segment 168h, and the bottom portion of segment 164.

Still referring to FIG. 18, passive RFID tag 30 is coupled to redundancy means 220 such that upper and lower edges of tag 30 are generally aligned with registration marks 184 that project outwardly from segment 166 of the right loop of redundancy means 220. In the illustrative example, the elongated loops each have a length that is at least three times width dimension 182 of the passive RFID tag 30. Thus, if desired, tag 30 can be coupled to the elongated loops of redundancy means 220 at positions above and below the illustrative position shown in FIG. 18.

While redundancy means 220 has only two points of contact with each of electrical contacts 162 of tag 30, less conductive ink is need to make the elongated loops of redundancy means 220 as compared to the other geometries of redundancy means 160, 160', 190, 200, 210 which have more points of contact with electrical contacts 162 of tag 30. As was the case with redundancy means 160, 160', 190, 200, 210 described above, dimensions 170, 178, 180, 182 are also shown in FIG. 18 in connection with the discussion of redundancy means 220. Therefore, the discussion above regarding dimensions 170, 178, 180, 182 and the relative comparisons between the dimensions is equally applicable to FIG. 18. It should also be appreciated that all dimensions mentioned herein, including dimensions 170, 178, 180, 182, are merely examples of suitable dimensions and that other embodiments having dimensions different than those specifically mentioned herein are within the scope of the present disclosure.

According to the present disclosure, in some embodiments of the incontinence detection pad 20 that includes redundancy means 160, 160', 190, 200, 210, 220, the associated substrate on which the redundancy means 160, 160', 190, 200, 210, 220 is provided may comprise the backsheet 34, 134 which, in turn, may include a first layer of fluid impermeable material and a second layer of nonwoven material as mentioned above. In such embodiments, the conductive ink forming the respective traces 136a, 136b and redundancy means 160, 160', 190, 200, 210, 220 is printed or otherwise deposited on the first layer of the backsheet 34, 134. The present disclosure also contemplates embodiments in which the incontinence detection pad 20 having redundancy means 160, 160', 190, 200, 210, 220 further includes fluid filter layer 28, 28a, 28b, as the case may be, that is situated so as to inhibit a low volume of fluid from being able to reach the first and second electrode traces 136a, 136b beneath the absorbent core 26.

Figure 19:
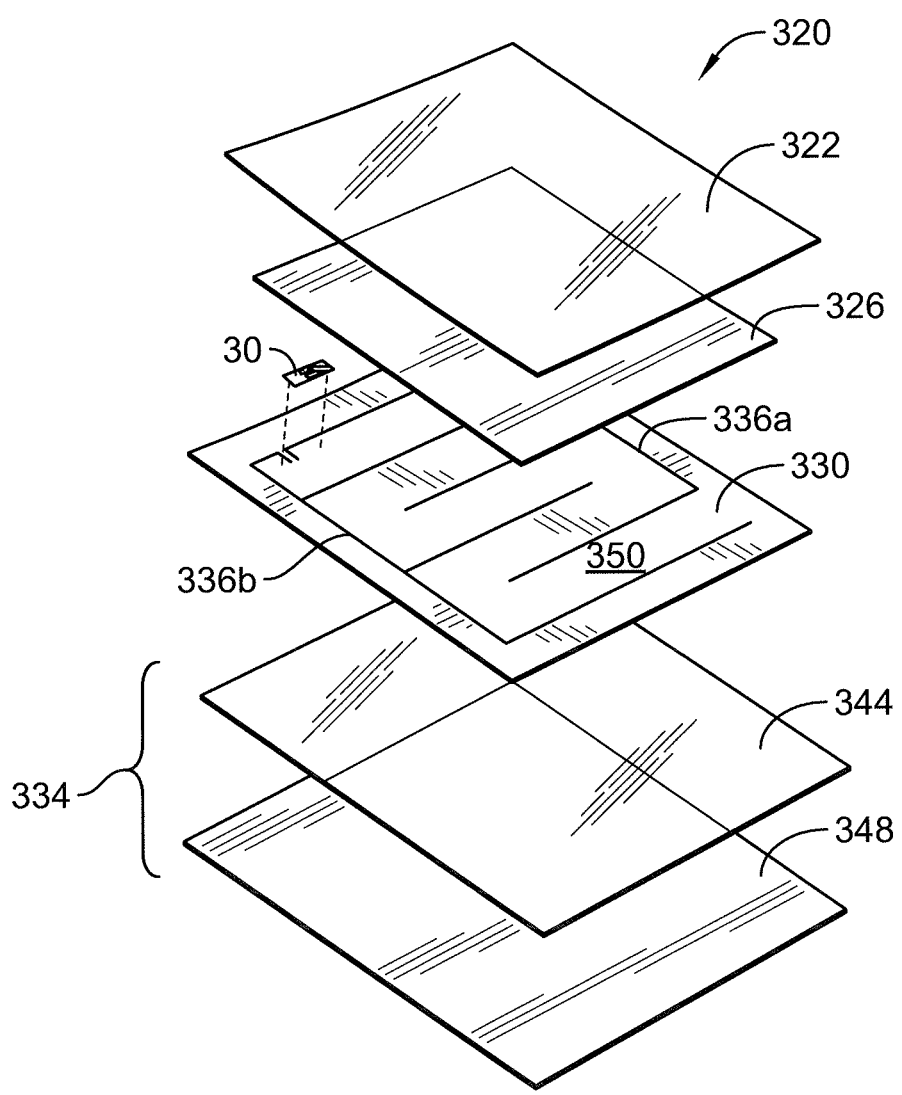
FIG. 19 is an exploded perspective view showing layers of an alternative embodiment of an incontinence detection pad including, from top to bottom, a topsheet of nonwoven material, a moisture absorbent core beneath the topsheet, a passive radio frequency identification (RFID) tag beneath the moisture absorbent core, an insert layer also beneath the moisture absorbent core and having electrodes printed thereon, a first layer of a backsheet beneath the insert layer, and a second layer of the backsheet beneath the first layer of the backsheet.

Referring now to FIG. 19, an alternative embodiment of an incontinence detection pad 320 includes, from top to bottom, a topsheet 322 of nonwoven material, a moisture absorbent core 326 beneath the topsheet, passive RFID tag 30 beneath the moisture absorbent core 326, an insert layer 330 also beneath the moisture absorbent core 326 and having electrodes 336a, 336b printed thereon, a first layer 344 of a backsheet 334 beneath the insert layer 330, and a second layer 348 of the backsheet 334 beneath the first layer 344 of the backsheet 334. In some embodiments, topsheet 322 is made of a fluid permeable material and first layer 344 of backsheet 334 is made of a fluid impermeable material. The adhesive used to couple topsheet 322, absorbent core 326, insert layer 330, and layers 344, 348 of backsheet 334 together is not shown in FIG. 19 but such adhesive is similar to that described above in connection with the disclosed embodiments of incontinence detection pad 20.

As shown in FIG. 19, absorbent core 326 and insert layer 330 are both situated between the topsheet 322 and the backsheet 334. More particularly, insert layer 330 is situated between the backsheet 334 and the absorbent core 326. The insert layer 330 includes a substrate 350 and a conductive ink pattern that is provided on the substrate and that is configured to form a first electrode trace 336a and a second electrode trace 336b. The passive RFID tag 30 is also provided on the substrate 350 and has electrical contacts that couple to the first and second electrode traces 336a, 336b.

There are a number of manufacturers that make absorbent pads for placement beneath patients to absorb and retain incontinence to prevent the incontinence from leaking onto the beds of the patients. Such absorbent pads oftentimes include topsheet 322, absorbent core 326, and a multi-layer backsheet 334 like those depicted in FIG. 19. However, these manufacturers do not make absorbent pads that have any electrical circuitry like that provided by electrode traces 336a, 336b and passive RFID tag 30. By providing the electrode traces 336a, 336b and tag 30 on substrate 350 of insert layer 330, the insert layer 330 can be added into existing absorbent pads during the manufacturing process to upgrade such pads into incontinence detection pads having circuitry to detect the incontinence and provide a wireless output signal indicative of the detected incontinence.

Construction of the existing absorbent pads occurs at very high speeds with rolls of material being provided for each of the topsheet 322, absorbent core 326, and a multi-layer backsheet 334. These are unrolled, adhered together, and cut at a rate of up to 300 pads per minute in some embodiments. In order to maintain such high manufacturing speeds when insert layer 330 is added into the combination, the present disclosure contemplates that the printing of traces 336a, 336b onto substrate 350 and the attachment of tag 30 to substrate 350 occurs separately from the manufacturing process which unrolls, adheres, and cuts the topsheet 322, absorbent core 326, and a multi-layer backsheet 334. Thus, rolls of insert layers 330 are manufactured for subsequent use. In some embodiments, the rolls of insert layers 330 are then laminated to respective rolls of absorbent core material such that the insert layers 330 and absorbent core 326 are supplied in the same roll of material. The roll of laminated insert layers 330 and absorbent cores 326 is then used in the manufacturing process just like the rolls of absorbent core material that does not include any insert layers 330 laminated thereto. In order to contain or minimize cost, this disclosure contemplates that substrate 350 of insert layer 330 comprises a relatively inexpensive material. For example, in some embodiments, the substrate 350 is made of a paper or a cellulosic nonwoven material or tissue paper.

In an alternative embodiment, the substrate 350 of the insert layer 330 comprises a standard sheet of paper (e.g., 8.5 inch by 11 inch sheet of paper or an A4 sheet of paper) and electrodes 336a, 336b are printed on the standard sheet of paper with RFID tag 30 also being attached to sheet of paper with its inputs coupled to electrodes 336a, 336b. The insert layer 330 formed by the sheets of paper with traces 336a, 336b and tag 30 thereon are then assembled into a standard incontinence pad during manufacture to convert it to an incontinence detection pad with wireless communication capability.

As noted above, the backsheet 334 includes first and second layers 344, 348. The first and second layers 344, 348 of the backsheet 334 are coupled together with a hot melt adhesive in some embodiments. Alternatively or additionally, the backsheet 334 further include a second layer 348 of polypropylene and, optionally, these first and second layers 344, 348 of the backsheet are coupled together with a hot melt adhesive.

In some embodiments, the incontinence detection pad 320 further include a fluid filter layer which is substantially similar to those discussed above in connection with FIGS. 1 and 2. It is contemplated that the fluid filter layer is situated between the absorbent core 326 and the insert layer 330. The fluid filter layer of pad 320 is configured to inhibit a low volume of fluid from being able to reach the first and second electrode traces 336a, 336b on the substrate 350 of the insert layer 330. After fluid of a sufficient volume greater than the low volume has passed through the topsheet 322, the absorbent core 326, and the fluid filter layer (e.g., layer 28, 28a, 28b, as the case may be), an electrical pathway is formed between the first and second electrode traces 336a, 336b by the fluid which enables the passive RFID tag 30 to emit a signal, in response to the passive RFID tag 30 being excited by external energy, that indicates an incontinence event may have occurred.

Optionally, the fluid filter layer of incontinence detection pad 320 is made from any of the materials mentioned above in connection with fluid filter layers 28, 28a, 28b, including being made from a hydrophobic polymeric nonwoven material or a hydrophilic material. For example, such a hydrophobic polymeric nonwoven material may comprise one or more of the following: a spunbond material, a spunlace material, a meltblown material, or a meltspun material. If desired, the hydrophobic polymeric nonwoven material may include a polypropylene or polyethylene material having a pore size and basis weight that may be configured to prevent the low volume of fluid from penetrating therethrough due to surface tension of the fluid. In some embodiments of the incontinence detection pad 320, the electrode traces 336a, 336b include redundancy means 160, 160', 190, 200, 210, 220 as described above.

In still another variant embodiment, substrate 350 of the insert layer 330 comprises a liquid filter layer, similar to layer 28 described above, and electrodes 336a, 336b are printed on the liquid filter layer with RFID tag 30 also being attached to liquid filter layer with its inputs coupled to electrodes 336a, 336b. Sheets of low density polyethylene (LDPE), high density polyethylene (HDPE), polyethylene terephthalate (PET), or polypropylene are examples of suitable material which may serve the dual purpose as liquid filter layers and substrates 350 of insert layers 330. In such embodiments, it is contemplated that the dual purpose liquid filter layer/substrates 350 are inserted into standard incontinence pads upside down, or in other words with the electrode traces 336a, 336b and tag 30 on the bottom surface of the substrate 350, assuming the backsheet 334 is below the substrate 350 and the topsheet 322 is above the substrate 350 as shown in FIG. 19, for example. In such embodiments, fluid volumes above the low volume of fluid that is blocked by the liquid filter layer, will eventually leech or absorb through the liquid filter layer/substrate 350 and bridge the electrodes 336a, 336b to form a closed circuit configuration indicating that the pad 320 is wet.

Adaptive Power Control

Use of RFID tags for incontinence detection has proven to be anything but straightforward. There are many nuances to interacting with the RFID tag, given the wide dynamic range of signals that the tag is likely to experience being firmly in the nearfield radiation zone of the antenna, being from 0 to at most ½ λ from the antenna. Receive signal strength at the tag can vary from an essentially unattenuated, +37 dBm signal, down to the edge of the detection (−18 dBm for the embodiments contemplated herein and in International Publication No. WO 2017/087452 A1 and U.S. application Ser. No. 15/596,036 which are already incorporated herein by reference, collectively "the incontinence detection systems") and below. Excessive transmit power has been shown to cause spurious false wet indications in the RFID tag, causing convoluted detection algorithms to be implemented in order to attempt to weed out successive strings of wet indications that may or may not be valid.

There are several indications available to the system that the inlay has either ample signal or more than ample signal required to perform its function. These may be exploited to control the output RF power in a more logical fashion than just transmitting +32 dBm into the +5 dBm gain antenna just because that is what is required in certain patient/pad configurations to allow the required pad read reliability to be realized across the entire defined read range for all patient body mass indexes (BMI's) in the range for which known non-bariatric beds are typically rated.

There are a number of indicators that the system either has ample signal or too much signal for the current patient/pad configuration (e.g., how the patient is placed on the pad and where the pad is on the defined read grid). Firstly, there is an indication in the status read back from the RFID tag that shows when an external power flag is set. The RFID chip of the RFID tags contemplated for use in the incontinence detection application is passively powered (parasitically from the EM field around the transmit antenna) and if a tamper input of the RFID chip shows that the chip thinks it is being externally powered, then there is clearly too much signal present and the power transmitted to the RFID tag can be reduced.

Another indicator that there is ample or too much signal is the number of transmit/receive (TX/RX) antenna combinations from which the RFID tag may be read. In some of the contemplated incontinence detection systems, there are a total of 12 combinations of one transmit antenna and three receive antennas (a total of 4 antennas, any one of which may be used as either a TX or a RX antenna). If a significant number of the combinations yield good reads, the system may be on the edge of having too much power available in some of the combinations.

Hardware of a reader that controls the transmissions from the designated TX antenna and that reads data received by one or more of the RX antennae has a feature which allows a receive signal level (RSL) figure of merit (FoM) to be read from a receiver of the hardware. In the past, this signal has been shown to be noisy and unreliable, but if applied to each TX/RX combination individually (i.e. a total of 12 FoM for receive quality) and sufficient averaging applied, a reliable indicator may be constructed which shows how well an RFID tag is receiving based on the strength of its transmit signal. This can be used as a clue as to how the channel is behaving on a TX/RX combination basis. At this point, a power control algorithm can be implemented on either a global level (one-size fits all transmit power, with the strongest combinations setting the power level) or on an individual TX/RX pair basis.

Because the incontinence detection systems exhibit good short term stability in terms of the RFID tag signal levels, both receive and transmit (there is no Rayleigh fading or time varying channel effects such as are seen in a mobile telephone environment), the signals exhibit cyclostationarity. There are nulls in the receive signal for different locations on the defined detection grid superimposed on the bed surface, but again they are cyclostationary and vary slowly with time, allowing for a small signal linearization approximation to be used. This should allow for a dynamic control of the output power to accommodate a wide range of path losses such as have been seen and documented in the development of the incontinence detection systems.

The transmit chain of the incontinence detection systems can output from +20 dBm to +33 dBm (e.g., more than a 10 dB range) under software control without any hardware modifications at all. Changes in pad/patient configuration can easily be accounted for when the receive FoM's deteriorate at the receiver, allowing for the output power to be changed to bring the system into the optimal configuration for reading a tag in a given location, which counter-intuitively, is not necessarily the configuration where the maximum number of reads of an RFID tag located in a given place with a given patient configuration. Two RFID tag parameters are simultaneously being balanced against each other, e.g. P (successful valid read) and P (RF power induced false wet). Both are controlled and influenced by the transmit output power. Using a TX/RX pair computed signal to noise ratio (SNR) RSL FoM to guide TX power can result in the optimal P (successful valid read) while minimizing P (false wet indication).

The output power to the transmit antenna is adjusted via software from a RFID reader chip, the AS3993/ST25RU2993 reader chip in some embodiments, of a power controller. In such embodiments, there is a register that provides 19 dB range from 0 dBm out to −19 dBm out by varying the RF output level from the reader chip. This signal is then amplified by a driver and final amplifier of the power controller. See FIGS. 29A-29C and the related discussion, particularly FIG. 29C, of International Publication No. WO 2017/087452 A1 which is already incorporated herein by reference. The 19 dB of dynamic range on the output is not actually obtained because the final RF amplifier is very heavy in gain compression (at least about 6 dB to about 9 dB). By adjusting an attenuator network on an output of the driver amplifier, a range of about 13 dB on the power output, roughly from about +18 dBm to about +31 dBm or so is achievable.

Figure 20:
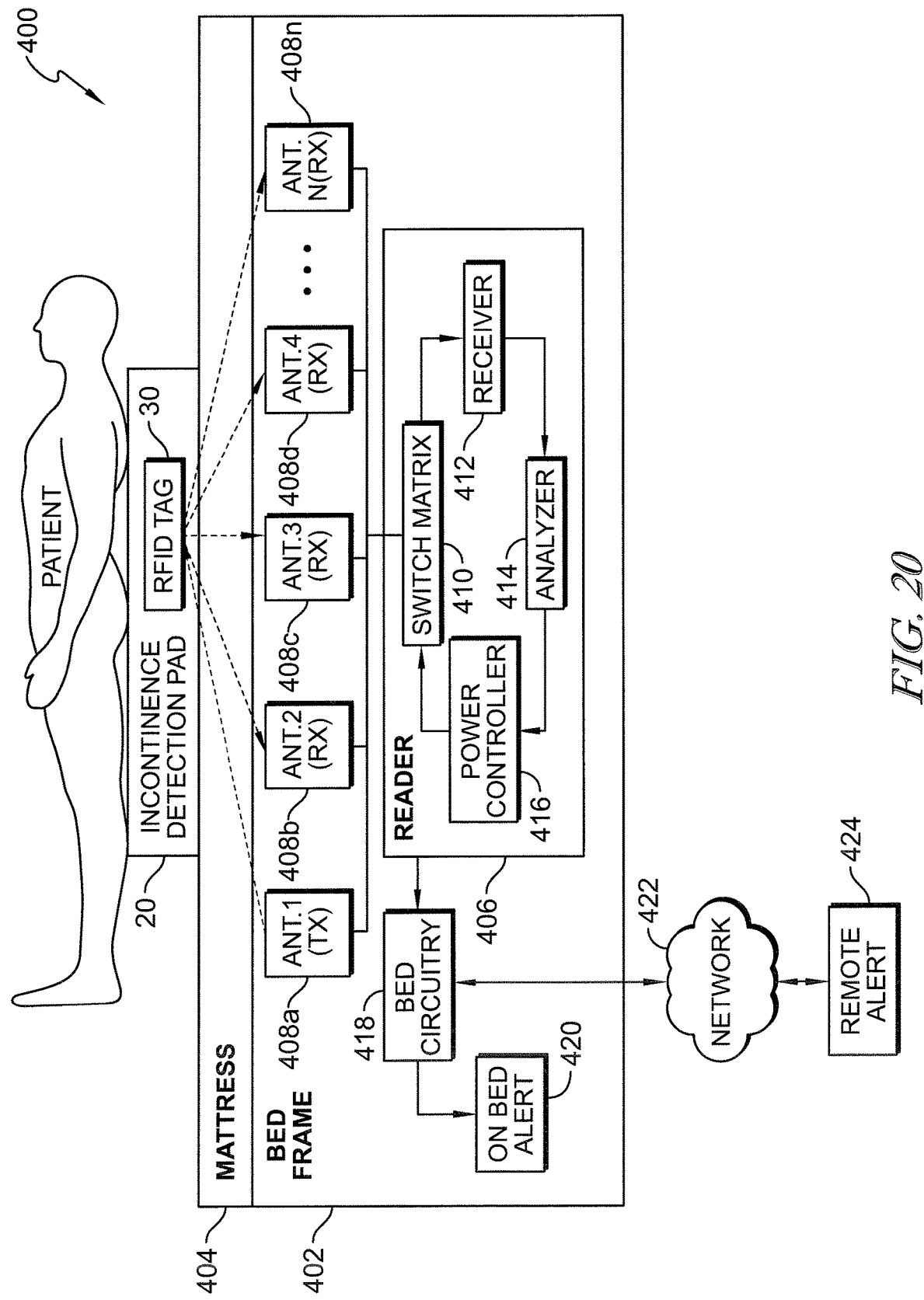
FIG. 20 is a block diagram of an incontinence detection system including a plurality of antenna couple to a bed frame, one of the antennae serving as a transmit antenna to generate a field to power up an RFID tag of an incontinence detection pad situated between a patient and a mattress on the bed frame, and others of the antennae serving as receive antennae to receive backscattered data from the RFID tag, the antennae being coupled to a reader that selects which of the antennae is the transmit antenna and that adjusts a power level to the transmit antennae to reduce the power level if the receive antennae that are able to read the backscattered data exceeds a predetermined number of receive antennae.

Referring now to FIG. 20 for purposes of further illustrating the concepts of the above discussion regarding Adaptive Power Control contemplated herein, a bed 400 includes a bed frame 402 and a mattress 404 supported on bed frame 402. Incontinence detection pad 20 is situated between mattress 404 and a patient and is operable to detect incontinence from the patient. Incontinence detection pad 20 is illustrated generically in FIG. 20 but any of the incontinence detection pads 20, 320 contemplated herein, as well as any of the incontinence detection pads contemplated in International Publication No. WO 2017/087452 A1 which is already incorporated herein by reference may just as well be used. A reader 406 is coupled to bed frame 404. A plurality of antennae 408a, 408b, 408c, 408d, 408n is also coupled to bed frame 402, such as being coupled to one or more sections of an articulated mattress-support deck (not shown) of bed frame 402.

Each antennae 408a, 408b, 408c, 408d, 408n is electrically coupled to a switch matrix 410 of reader 406. Switch matrix 410 is operable to determine which antenna 408a, 408b, 408c, 408d, 408n is the designated transmit antenna and which of antennae 408a, 408b, 408c, 408d, 408n are the receive antennae. In the illustrative example of FIG. 20, antenna 408a is designated as the transmit antennae and the remaining antennae 408b, 408c, 408d, 408n are the receive antennae. Reader 406 applies power to transmit antenna 408a which produces an electromagnetic field to power the passive RFID tag 30 of pad 20 and antennae 408b, 408c, 408d, 408n are activated one at a time by switch matrix 410 resulting in a receiver 412 of reader 406 being operated to "listen" for a backscattered signal emitted from tag 30 and received by the activated receive antenna 408b, 408c, 408d, 408n.

Reader 406 includes an analyzer 414 that is electrically coupled to receiver 412. Analyzer 414 is operable to analyze the backscattered signal, if any, received by receiver 412 from the activated receive antenna 408b, 408c, 408d, 408n. Thus, analyzer 414 determines the TX/RX SNR and the RSL FoM and also performs the averaging of the received backscattered signals. In some embodiments, analyzer 414 determines if the backscattered data indicates that a power flag has been set by the RFID tag 30. Based on the analysis of the signals from the various TX/RX pairs of antennae 408a, 408b, 408c, 408d, 408n, a power controller 416 of reader is operated to adjust the power level that is applied to the designated transmit antenna 408a, 408b, 408c, 408d, 408n. As noted above, the goal is to reduce the transmit power level so as to reduce the number of false wet positives that are induced in RFID tag 30 by the electromagnetic field generated by the transmit antenna 408a, 408b, 408c, 408d, 408n.

Reader 406 is coupled to bed circuitry 418 of bed 400. Thus, if the backscattered signal from RFID tag 30 includes data indicating that incontinence detection pad 20 is wet, reader 406 operates to notify bed circuitry 418 of the wet condition of pad 20 and, in turn, bed circuitry activates an on bed alert 420. Alert 420 includes, for example, an audible alert, a textual or graphical message shown on a display screen of bed 400, or an on bed alert light being illuminating in a particular manner (e.g., causing the alert light to illuminate a yellow or amber color). In some embodiments, bed circuitry 418 sends a message to a remote alert 424, such as via a network 422 of a healthcare facility. Remote alert 424 includes, for example, a remote computer, such as a master nurse station computer, which displays a textual or graphical message on a display indicating that the pad 20 is wet, a caregivers mobile device which displays a textual or graphical message indicating that the pad 20 is wet, or an indicator light (aka dome light) of a nurse call system that is located in a hallway adjacent the patient's room being illuminated in a particular manner.

So, based on the forgoing, the present disclosure contemplates a method of controlling an incontinence detection system. The method includes establishing a first antenna 408a, 408b, 408c, 408d, 408n of a plurality of antennae 408a, 408b, 408c, 408d, 408n as a transmit antenna that is used to wirelessly energize a passive RFID tag 30 of an incontinence detection pad 20 at a first power level. The plurality of antennae 408a, 408b, 408c, 408d, 408n includes N spaced apart antennae, with N being an integer equal to or greater than three. The method further includes establishing each of the plurality of antennae 408a, 408b, 408c, 408d, 408n, except for the first antenna, as receive antennae that each listen for backscattered data emitted from the passive RFID tag 30. The method further includes reducing the first power level to a second power level if the receive antennae that are able to read the backscattered data exceeds a predetermined number of receive antennae and the predetermined number being less than N−1.

In some embodiments, the method further includes analyzing signal to noise ratio between the transmit antenna and each of the receive antenna before reducing the first power level to the second power level. Alternatively or additionally, the method further includes analyzing a receive signal level (RSL) figure of merit (FoM) of the backscattered data before reducing the first power level to the second power level. Optionally, the RSL FoM of multiple emissions of backscattered data is averaged before reducing the first power level to the second power level. Further alternatively or additionally, the method further includes determining that an external power flag is set in the backscattered data before reducing the first power level to the second power level.

In some embodiments, the predetermined number of receive antennae includes two receive antennae. That is, the power level is reduced until only two receive antennae are able to receive the backscattered signal from tag 30. Alternatively, the predetermined number of receive antennae includes one receive antenna. That is, the power level is reduced until only one receive antenna is able to receive the backscattered signal from tag 30. In some embodiments, the first power level and the second power level lie within a range of about +20 decibel milliWatt (dBm) to about +33 dBm.

In some embodiments, the method further includes cycling through the plurality of antennae as being established as the transmit antenna with each of the remaining antennae of the plurality of antennae being established as the receive antenna for a period of time. Optionally, the plurality of antennae are coupled to a bistatic radio frequency (RF) switch matrix which is operable to establish which antenna of the plurality of antennae is the transmit antenna and to establish which antenna of the plurality of antennae is the receive antenna. See FIG. 8 and the related discussion in U.S. application Ser. No. 15/596,036 which is already incorporated herein by reference. In some embodiments, the method further includes operating the bistatic RF switch matrix to cause the transmit antenna to transmit using a frequency hopping scheme. The frequency hopping scheme may use 50 distinct frequencies, for example, with each frequency being used only once in a pseudo-random order before any of the 50 frequencies are repeated. In some embodiments, the 50 frequencies lie within a range between about 902 MegaHertz (MHz) and about 928 MHz.

Figure 21:
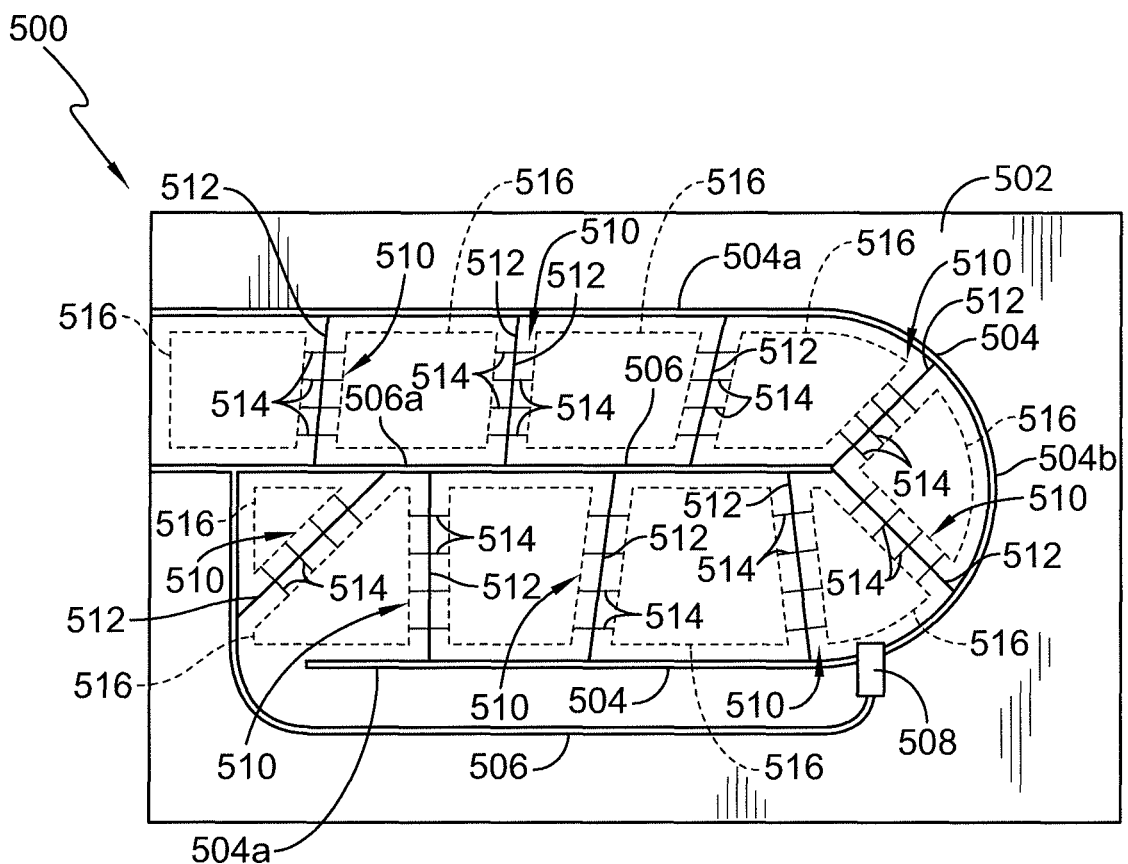
FIG. 21 is a top plan view showing another alternative embodiment of an incontinence detection pad having first and second electrode traces, a number of hydrophilic bridges interconnecting the first and second electrode traces, and hydrophobic zones between the bridges.

Referring now to FIG. 21, an absorbent article 500 includes a substrate 502, a first electrode 504 on the substrate 502, a second electrode 506 on the substrate 502 and circuitry 508 coupled to the electrodes 504, 506. The second electrode 506 is spaced from the first electrode 504. Circuitry 508 is operable to monitor whether a biofluid is present on the substrate in a sufficient volume (e.g., greater than a low volume as discussed above) by determining whether the first and second electrodes 504, 506 are in an open circuit configuration or a closed circuit configuration. The open circuit configuration is indicative of an absence of biofluid and the closed circuit configuration is indicative of a presence of biofluid. The absorbent article 500 further includes a plurality of high wick bridges 510 that interconnect the first and second electrodes 504, 506.

In the illustrative embodiment, the first electrode 504 include a pair of generally straight segment 504a interconnected by a generally semi-circular segment 504b. The second electrode 506 includes a generally straight segment 506a that is substantially parallel with, and located between, straight segments 504a. Each of the high wick bridges include a generally straight main segment 512 and a series of hash segments 514. In some embodiments, the main segment 512 of at least some of the high wick bridges 510 are substantially perpendicular to the first and second segments 504a, 506a of the respective electrodes 504, 506. In this regard about 80 degrees to about 110 degrees is considered to be substantially perpendicular according to the present disclosure.

In the illustrative embodiment, each has segment 514 of the series of hash segments 514 is substantially perpendicular with the associated main segment 512. The main segment 512 bisects each of the hash segments 514 in the illustrative example, but this need not be the case. Furthermore, the hash segments 514 are each of substantially equivalent lengths in the illustrative example, but this also does not need to be the case. Each of the high wick bridges 510 has four hash segments 514 associated with each main segment 512 but the present disclosure contemplates that more or less hash segments 514 than four, including no hash segments 514 at all, may be associated with the respective main segments 512. Different main segments 512 may have a different number of hash segments 514 associated therewith, if desired.

In some embodiments in including the illustrative embodiment, the absorbent article 500 further includes a hydrophobic material situated within each of a plurality of zones 516. Zones 516 are bounded generally by respective portions of the first and second electrodes 504, 506 and by respective pairs of adjacent high wick bridges 510. The hydrophobic material may comprise a hydrophobic coating or hydrophobic material of any of the types discussed hereinabove, for example. As shown in FIG. 21, the hydrophobic material in at least some of the zones 516 is quadrilateral in shape. Ends of the hash segments 514 each terminate at a respective boundary of a corresponding zone 516 in the illustrative embodiment. In other embodiments, the ends of hash segments 514 are spaced from, but are in close proximity to, a respective boundary of the hydrophobic material in each zone 516. It should be appreciated that the circuitry 508 may include a radio frequency identification (RFID) tag such as any of the passive RFID tags discussed hereinabove. Optionally, circuitry 508 may comprise an active RFID tag that is powered with a battery or other power source.

Liquid, such as urinary incontinence, runs off of the hydrophobic material of each of zones 516 and is collected by the hash segments 514 of the respective high wick bridges 510 situated between zones 516. Hash segments 514 direct the moisture or wetness to the respective main segment 512 of the corresponding high wick bridges 510. After an main segment 512 is wetted from one end to the other, a closed circuit configuration is established between electrodes 504, 506 and circuitry 508 provides a signal indicating that pad 500 is wet, either via backscattered data in response to being irradiated with energy in the case of a passive RFID tag, or via an active transmission in the case of an active RFID tag.

By providing pad 500 with high wick bridges 510 between electrodes 504, 506 and with hydrophobic zones 516, the sensitivity of pad 500 is increased as compared to a similarly constructed pad without bridges 510 or zones 516. That is, a smaller volume of fluid will result in a closed circuit configuration being created between electrodes 504, 506. Furthermore, by configuring bridges 510 and/or zones 516 appropriately, the fluid deposited on the pad 500 can be directed away from the regions of the pad 500 over which a patient is expected to be. Thus, skin breakdown due to moisture is alleviated or reduced in such embodiments. Once the moisture is directed way from the patient by the high wick bridges 510 and hydrophobic zones 516, the moisture is able to evaporate from the pad 500 more easily.

Embodiments of pad 500 having high wick bridges 510 but without hydrophobic zones 516 are contemplated by this disclosure as are embodiment having spaced apart hydrophobic zone 516 but without high wick bridges 510. It should be appreciated that pad 500 includes one or more of the various other layers of material discussed above. For example, substrate 502 of pad 500 comprises the backsheet (e.g., double layer of material as discussed above) in some embodiments and an absorbent core and a top sheet is also provided in the pad along with the various adhesive material to couple these layers together. A fluid filter layer of any of the types discussed above also may be included in pad 500 although, the purpose of the filter layer to prevent low volumes of fluid from creating false positive readings is at odds with the purpose of the high wick bridges 510 and hydrophobic zones 516 to increase the sensitivity of pad 500 to output "wet" readings at lower volumes of fluid. In any event, there may be situations in which a designer may wish to have a higher moisture detection sensitivity in one or more regions of pad 500, in which case bridges 510 and/or zones 516 are provided in such region(s), and to have a lower moisture detection sensitivity in other regions of the pad 500, in which case a fluid filter layer is provided in such other region(s).

Figure 22:
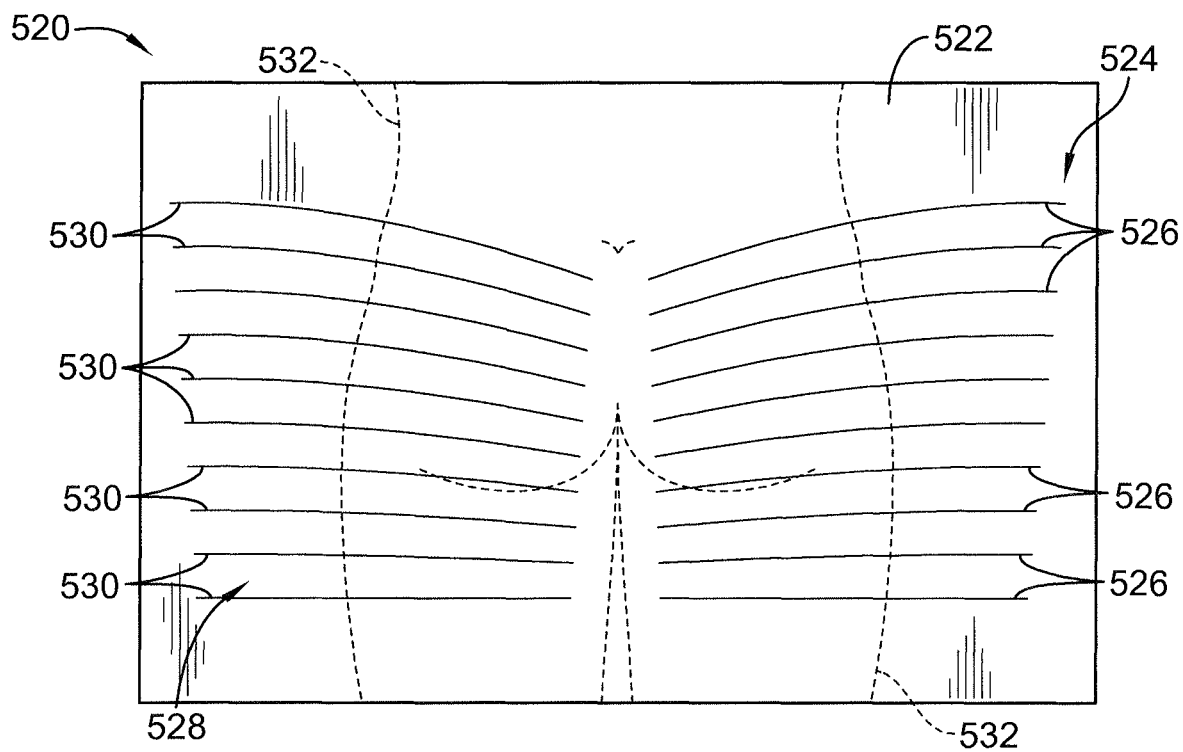
FIG. 22 is a top plan view of view of yet another alternative embodiment of an incontinence detection pad having a first series of spaced apart hydrophilic fluid guide paths on a right side of the pad and a second series of spaced apart hydrophilic fluid guide paths on a left side of the pad, the first and second hydrophilic guide paths being mirror images of each other.

Referring now to FIG. 22, an absorbent article 520 includes a substrate 522, a first series 524 of spaced apart hydrophilic fluid guide paths 526 located on a right side of the substrate 522, and a second series 528 of spaced apart hydrophilic fluid guide paths 530 located on a left side of the substrate 522. The first and second hydrophilic guide paths 526, 530 of the respective first series 524 and second series 528 are mirror images of each other in the illustrative example. Inner ends of each guide path 526 are spaced apart from a corresponding end of a companion guide path 530. The hydrophilic fluid guide paths 526, 530 are each configured to direct moisture away from a patient situated atop a central region of the substrate 522 as indicated by the patient footprint 532 (in dotted).

Each fluid guide path 526, 530 of the respective first and second series 524, 528 of fluid guide paths 526, 530 extend from the central region of the substrate 522 beyond the footprint 532 of the patient's body to a respective side region of the substrate beyond the footprint 532 of the patient's body. Thus, for discussion purposes, portions of pad 520 inside footprint 532 are considered to be in the central region of pad 520 or substrate 522, and portions of pad 520 outside of footprint 532 are considered to be the side regions of pad 520 or substrate 522.

Evaporation of moisture in the side regions of pad 520 on opposite sides of the footprint 532 produce a moisture gradient within the hydrophilic fluid guide paths 526, 530 so that moisture within the footprint 532 moves outwardly to the side regions away from the patient. Furthermore, pressure produced on the fluid guide paths 526, 530 by the patient in the central region results in moisture moving outwardly to the side regions away from the patient. In the illustrative example, the substrate 522 is generally rectangular in shape and each fluid guide path 526, 530 of the first and second series 524, 528 of guide paths 526, 530 is oriented generally along a long dimension of the substrate. With regard to the high wick bridges 510 and hydrophilic fluid guide paths discussed above, examples of suitable hydrophilic materials having high wick rates include the following materials: polypropylene, Meryl Skinlife®, SORBTEK™, and Poro-Tex expanded PTFE (ePTFE).

In some uses, pad 520 is placed upon a mattress having a microclimate management (MCM) layer at the top of the mattress. Air is blown through the MCM layer to wick moisture away from the patient above the MCM layer thereby to keep the interface between the patient and the mattress relatively dry. The air moving through the MCM layer will tend to dry out the side regions of pad 520 more so than the central region of pad 520 beneath the patient. As the side regions dry due to the air moving in the MCM layer, a moisture gradient is created so that moisture more readily moves from the central region of pad 520 to the side regions. This same phenomenon occurs due to exposure of the side regions of pad 520 to ambient air without the use of an MCM layer, but having an MCM layer with actively moved air enhances the evaporation rate at the side regions of pad 520.

In a variant embodiment, a hydrophobic material (e.g., layer or coating) is provided in the central region of pad 520 so that incontinence or other biofluid is spread away from the central region due to pressure by the weight of the patient in the central region. The hydrophobic material has side boundaries that terminate at or near the side regions of pad 520, such as in the vicinity of the dotted lines of footprint 532 so that an absorbent material, such as the illustrative fluid guide paths 526, 530, collect the moisture as it moves outwardly to the side regions from beneath the patient. Humidity adjacent the patient's is reduced in each of the embodiments just described in connection with FIG. 22. Thus, skin damage is reduced because the patient's exposure to urine and other biofluids is reduced.

As noted above in connection with FIG. 9B, backsheet 134 includes breathable low density polyethylene (LDPE) film 144 which serves as an upper layer of the backsheet 134 and a layer of polypropylene (PP) spunbond nonwoven material 148 which serves as a lower layer of the backsheet 134 when the associated incontinence detection pad is in use beneath a patient with the backsheet 134 at the bottom of the incontinence detection pad. In a similar manner, backsheet 334 of FIG. 19 includes upper layer 344 and lower layer 348. Backsheet 46 of incontinence detection pad 20 of FIGS. 1-3 is similarly constructed with a two-layer backsheet in some embodiments. The discussion below will refer to film 144 and nonwoven material 148 but the discussion is equally applicable to layers 344, 348 and to two-layer embodiments of pad 20 constructed with these same or substantially similar materials.

While LDPE film 144 is fluid impermeable, it is a breathable film which has moisture vapor permeability. Thus, film 144 is a microporous (breathable) polyethylene film. Of course, the PP spunbond nonwoven material 148 of backsheet is very porous to both air and liquid. The microporous nature of film 144 renders it porous to air and moisture vapor due to microfractures introduced by using a calcium carbonate filler. Although film 144 is not porous to water (e.g., film 144 is impermeable to liquid), it is so thin, on the order of about 0.001 inches in illustrative embodiments, that it has been found that the conductive ink of electrode traces 36a, 36b, 136a, 136b, 336a, 336b, as the case may be, sometimes seeps into the microfractures and/or water vapor accumulates beneath the associated incontinence detection pad to such an extent that electrodes 36a, 36b, 136a, 136b, 336a, 336b become electrically connected in a closed circuit arrangement from underneath the pad. This results in a false positive incontinence detection alarm being generated.

Also, when a soiled incontinence detection pad is removed from beneath a patient, caregivers typically clean the patient with wet sponges and/or towels which may get the underlying bedsheets wet and, in some instances, caregivers may change the bed sheets and wipe down an upper surface of the mattress ticking (e.g., the outer surface of the mattress). In either case, there is sometimes enough fluid or moisture from the sponges or towels, or left on the upper surface of the mattress ticking from the cleaning process, that the bed sheets become sufficiently damp or moist that the moisture is able to seep through the nonwoven material 148 and into the microfractures of the film 144, thereby resulting in electrodes 36a, 36b, 136a, 136b, 336a, 336b becoming electrically connected in a closed circuit arrangement from underneath the pad. This is another way in which false positive incontinence detection alarms may be being generated.

Figure 23:
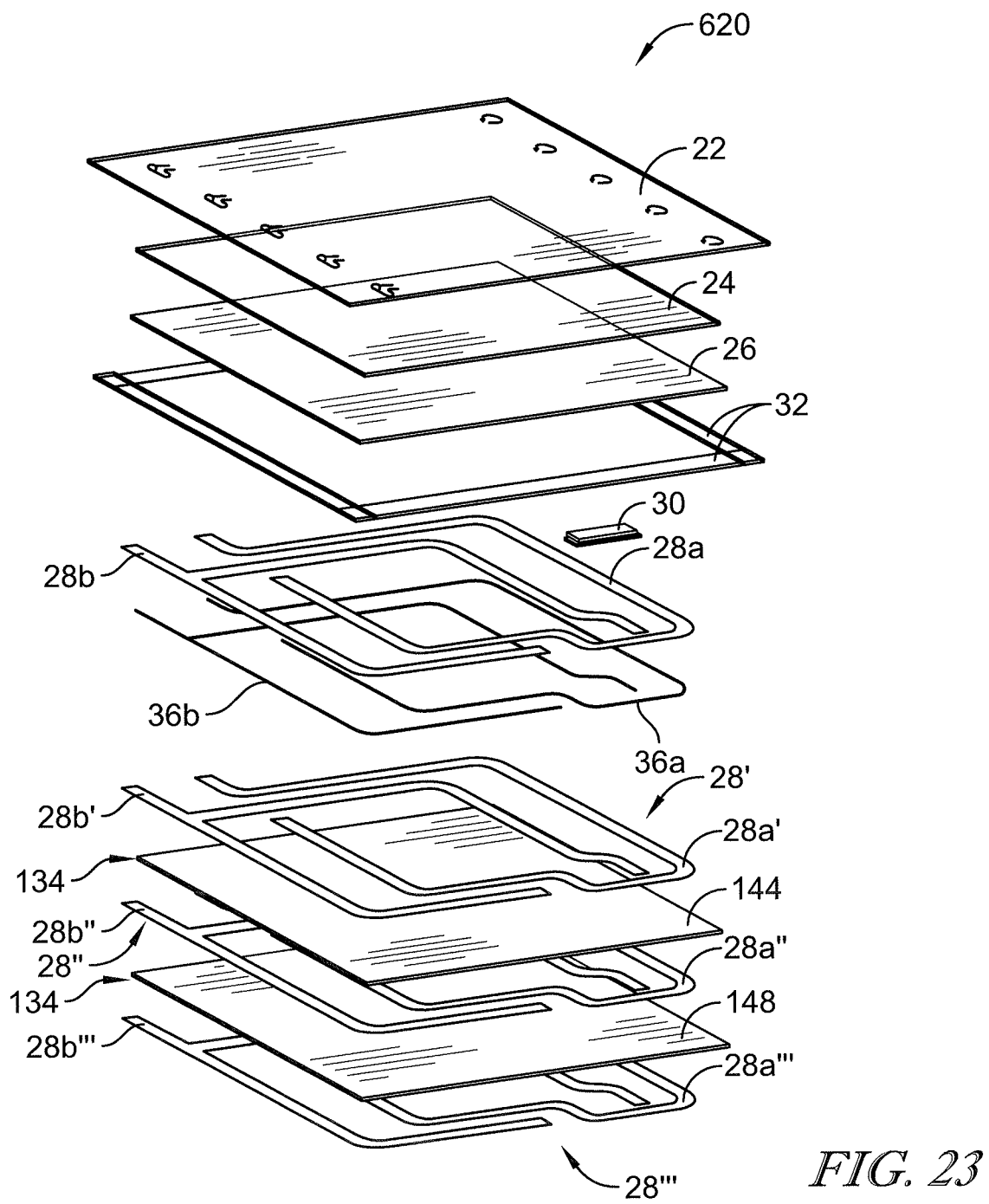
FIG. 23 is an exploded perspective view showing layers of an alternative embodiment of an incontinence detection pad including, from top to bottom, a topsheet of nonwoven material, a layer of slot coated adhesive beneath the topsheet, a moisture absorbent core beneath the layer of adhesive, a layer of peripheral hot melt adhesive, a passive radio frequency identification (RFID) tag beneath the layer of peripheral hot melt adhesive, a first fluid filter layer, first and second electrode traces having a geometry similar to that of the first fluid filter layer, a first option for a location of a second fluid filter layer in the incontinence detection pad, an upper layer of a backsheet, a second option for a location of the second fluid filter layer in the incontinence detection pad, a lower layer of the backsheet, and a third option for a location of the second fluid filter layer, the second fluid filter layer being shaped substantially the same as the geometry of the electrodes and the first fluid filter layer.

To alleviate the false alarming problem described in the preceding two paragraphs, the present disclosure contemplates that an alternative embodiment incontinence detection pad 620 has an additional liquid or fluid filter layer 28' or 28" or 28'" located underneath the electrode traces 36a, 36b as shown in FIG. 23. In one version of pad 620, liquid filter layer 28' includes liquid filter layer portions 28a', 28b' located directly beneath electrode traces 36a, 36b and above film 144 of the associated backsheet 134. Portions 28a', 28b' have the same geometry as respective electrode traces 36a, 36b, but are wider (e.g., about 3 mm to about 25 mm) than the width of electrode traces 36a, 36b (e.g., about 1 mm to about 3 mm). In fact, the geometry of portions 28a', 28b' beneath electrodes 36a, 36b is substantially the same as the geometry of portions 28a, 28b of the liquid filter layer above the electrodes 36a, 36b in the illustrative example, but this need not be the case in other embodiments.

In some embodiments, electrodes 36a, 36b are printed onto portions 28a', 28b', respectively, either before or after portions 28a', 28b' are applied to film 144. In other embodiments, electrodes 36a, 36b are printed on a bottom surface (as oriented in FIG. 23) of portions 28a, 28b of the overlying fluid filter layer. During manufacture, the bottom surface of portions 28a, 28b may be facing upwardly during the process of printing electrodes 36a, 36b thereon. In a further variant, the electrodes 36a, 36b are printed on a substrate 350 of an insert layer 330, as described above in connection with FIG. 19, and the insert layer 330 with electrodes 36a, 36b (and RFID tag 30) is situated beneath fluid filter layer portions 28a, 28b and above fluid filter layer portions 28a', 28b'.

In another version of pad 620, a liquid filter layer 28" includes liquid filter layer portions 28a", 28b" located beneath film 144 and above nonwoven material 148 of backsheet 134. Portions 28a", 28b" are aligned with electrodes 36a, 36b, respectively, and have the same basic geometry as electrodes 36a, 36b, but like layer 28', are wider (e.g., about 3 mm to about 25 mm) than the width of electrodes 36a, 36b (e.g., about 1 mm to about 3 mm). In yet another version of pad 620, a liquid filter layer 28'" includes liquid filter layer portions 28a'", 28b'" located beneath nonwoven material 148 of backsheet 134. Portions 28a'", 28b'" are aligned with electrodes 36a, 36b, respectively, and have the same basic geometry as electrodes 36a, 36b, but like layers 28' and 28", are wider (e.g., about 3 mm to about 25 mm) than the width of electrodes 36a, 36b (e.g., about 1 mm to about 3 mm). Thus, in some embodiments, the layers 28', 28", 28'" depicted in FIG. 23 are mutually exclusive in that only one of layers 28', 28", 28'" is present in any given version of pad 620. In other embodiments, any two of layers 28', 28", 28'" are present in further versions of pad 620. If desired, all three of layers 28', 28", 28'" are present in still a further variant of pad 620.

As shown in FIG. 23, in addition to electrodes 36a, 36b, backsheet 134, and one or more of fluid filter layers 28', 28", 28'", pad 620 also includes topsheet 22, layer 24 of slot coated adhesive beneath the topsheet 22, moisture absorbent core 26 beneath the layer 24 of adhesive, the upper fluid filter layer having portions 28a, 28b beneath the absorbent core 26, passive radio frequency identification (RFID) tag 30, and perimeter adhesive layer 32. The discussion above regarding elements 22, 24, 26, 28a, 28b, 30, 32, 36a, 36b, 134, 144, 148 in connection with various incontinence detection pad embodiments is equally applicable to incontinence detection pad 620 for these various components. Furthermore, the discussion above regarding the features of the filter layer 28a, 28b, including the materials from which filter layer 28a, 28b may be made, is equally applicable to filter layers 28', 28", 28'" and their respective portions 28a', 28b', 28a", 28b", 28a'", 28b'".

Optionally, in some embodiments of pad 620, filter layers 28', 28", 28'", as the case may be, and their respective portions 28a', 28b', 28a", 28b", 28a'", 28b'" are made of a material that is both fluid impermeable and moisture vapor impermeable. Vinyl material is an example of such material. It is also within the scope of the present disclosure that film 144 and/or nonwoven material 148 is made of a material that is less moisture vapor permeable, including making either or both of layers 144, 148 of backsheet 134 from a fluid impermeable and moisture vapor impermeable material such as vinyl material. However, it is preferable for patient comfort to have a breathable backsheet 134 if possible. Even in embodiments using fluid/moisture vapor impermeable filter layers 28', 28", 28'" having respective portions 28a', 28b', 28a", 28b", 28a'", 28b'", the majority of the surface area of backsheet 134 is still moisture vapor permeable or breathable.

Figure 24:
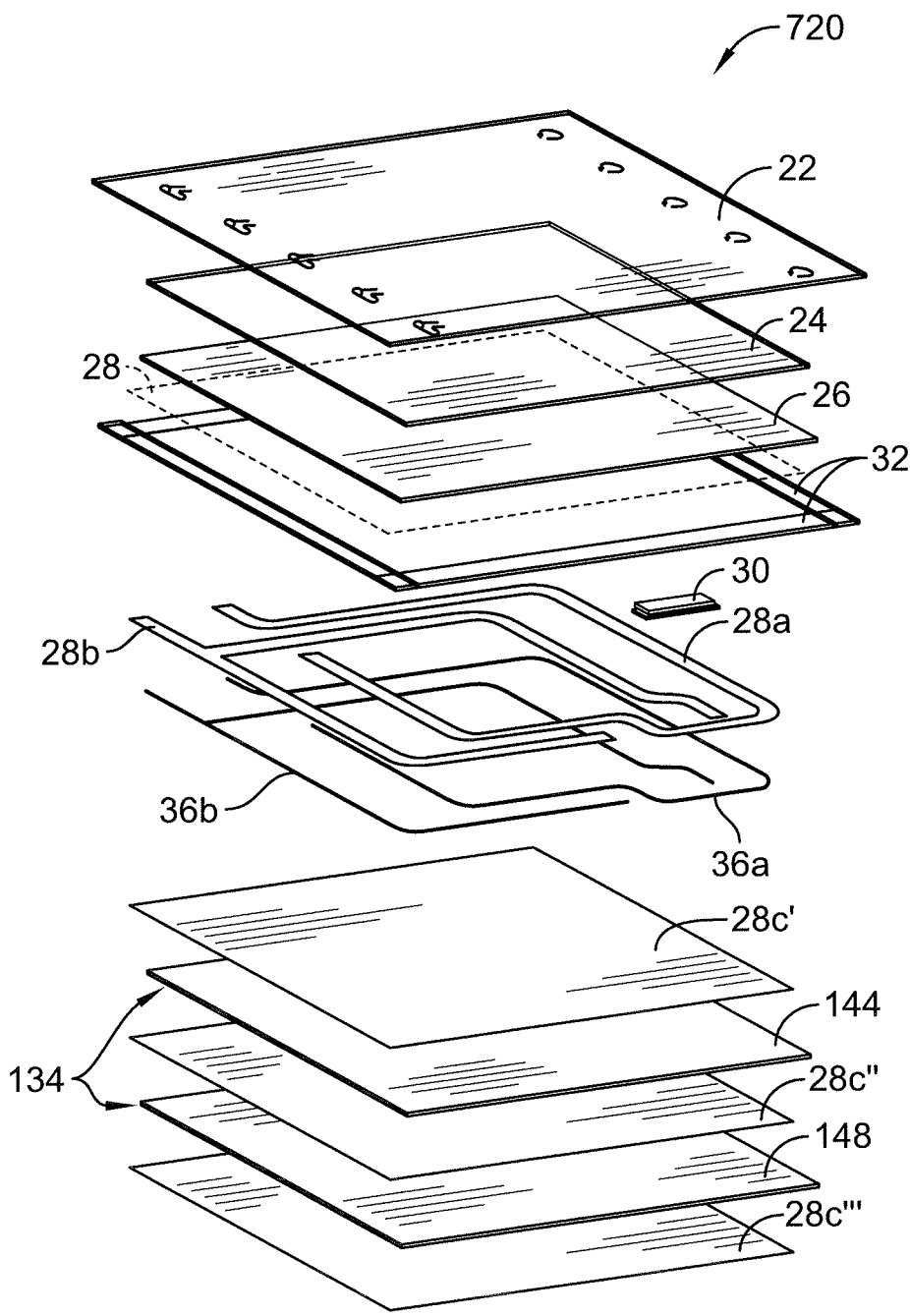
FIG. 24 is an exploded perspective view, similar to FIG. 23, but showing three options for the locations of a second fluid filter that is rectangular in shape rather than following the geometry of the first and second electrodes.

Referring now to FIG. 24, instead of having layers 28', 28", 28'" with portions 28a', 28b', 28a", 28b", 28a'", 28b'" that generally match the geometry of electrodes 36a, 36b, the present disclosure contemplates several versions of an incontinence detection pad 720 that have one or more rectangular fluid filter layers 28c', 28c", 28c'". In a first version of pad 720, fluid filter layer 28c' is located directly beneath electrode traces 36a, 36b and above film 144 of the associated backsheet 134. In some embodiments, electrodes 36a, 36b are printed onto layer 28c', either before or after layer 28c' is applied to film 144. In other embodiments, electrodes 36a, 36b are printed on a bottom surface (as oriented in FIG. 24) of portions 28a, 28b of fluid filter layer 28. During manufacture, the bottom surface of portions 28a, 28b may be facing upwardly during the process of printing electrodes 36a, 36b thereon as noted above. In a further variant, the electrodes 36a, 36b are printed on a substrate 350 of an insert layer 330, as described above in connection with FIG. 19, and the insert layer 330 with electrodes 36a, 36b (and RFID tag 30) is situated beneath fluid filter layer portions 28a, 28b and above fluid filter layer portions 28c'.

In another version of pad 720, a liquid filter layer 28c" is located beneath film 144 and above nonwoven material 148 of backsheet 134. In yet another version of pad 720, a liquid filter layer 28c'" is located beneath nonwoven material 148 of backsheet 134. Thus, in some embodiments, the layers 28c', 28c", 28c'" depicted in FIG. 24 are mutually exclusive in that only one of layers 28c', 28c", 28c'" is present in any given version of pad 720. In other embodiments, any two of layers 28c', 28c", 28c'" are present in further versions of pad 720. If desired, all three of layers 28c', 28c", 28c'" are present in still a further variant of pad 620. Fluid filter layers 28c', 28c", 28c'" shown in FIG. 24 have outer peripheries that are coextensive with the outer peripheries of layers 144, 148 of backsheet 134 and/or with the outer periphery of topsheet 22. In other embodiments, fluid filter layers 28c', 28c", 28c'" have outer peripheries that are coextensive with absorbent core 26.

In still further versions of pad 720, fluid filter layer 28a, 28b is omitted and a fluid filter layer 28 (shown in phantom in FIG. 24) having a rectangular shape is used instead. This fluid filter layer 28 may be used in any of the embodiments of pad 720 described herein in lieu of fluid filter layer 28*a*, 28*b*. Thus, pads 720 having upper fluid filter layer 28 in combination with any one or more of lower fluid filter layers 28*c'*, 28*c"*, 28*c'"* are contemplated by this disclosure. The discussion above of fluid filter layer 28 of FIG. 1 in connection with incontinence detection pad 20 is equally applicable to the fluid filter layer 28 when used in any of the contemplated embodiments of pad 720.

As shown in FIG. 24, in addition to electrodes 36*a*, 36, backsheet 134, and one or more of fluid filter layers 28*c'*, 28*c"*, 28*c'"*, pad 670 also includes topsheet 22, layer 24 of slot coated adhesive beneath the topsheet 22, moisture absorbent core 26 beneath the layer 24 of adhesive, fluid filter layer 28 (in phantom) or fluid filter layer 28*a*, 28*b* beneath the absorbent core 26, passive radio frequency identification (RFID) tag 30, and perimeter adhesive layer 32. The discussion above regarding elements 22, 24, 26, 28, 28*a*, 28*b*, 30, 32, 36*a*, 36*b*, 134, 144, 148 in connection with various incontinence detection pad embodiments is equally applicable to incontinence detection pad 720. Furthermore, the discussion above regarding the features of filter layer 28 and filter layer 28*a*, 28*b*, including the materials from which filter layer 28 and filter layer 28*a*, 28*b* may be made, is equally applicable to filter layers 28*c'*, 28*c"*, 28*c'"*.

Optionally, in some embodiments of pad 720, filter layers 28*c'*, 28*c"*, 28*c'"*, as the case may be, are made of a material that is both fluid impermeable and moisture vapor impermeable. As noted above, vinyl material is an example of such material. It is also within the scope of the present disclosure that film 144 and/or nonwoven material 148 of pad 720 is made of a material that is less moisture vapor permeable, including making either or both of layers 144, 148 of backsheet 134 from a fluid impermeable and moisture vapor impermeable material such as vinyl material.

Figure 25:
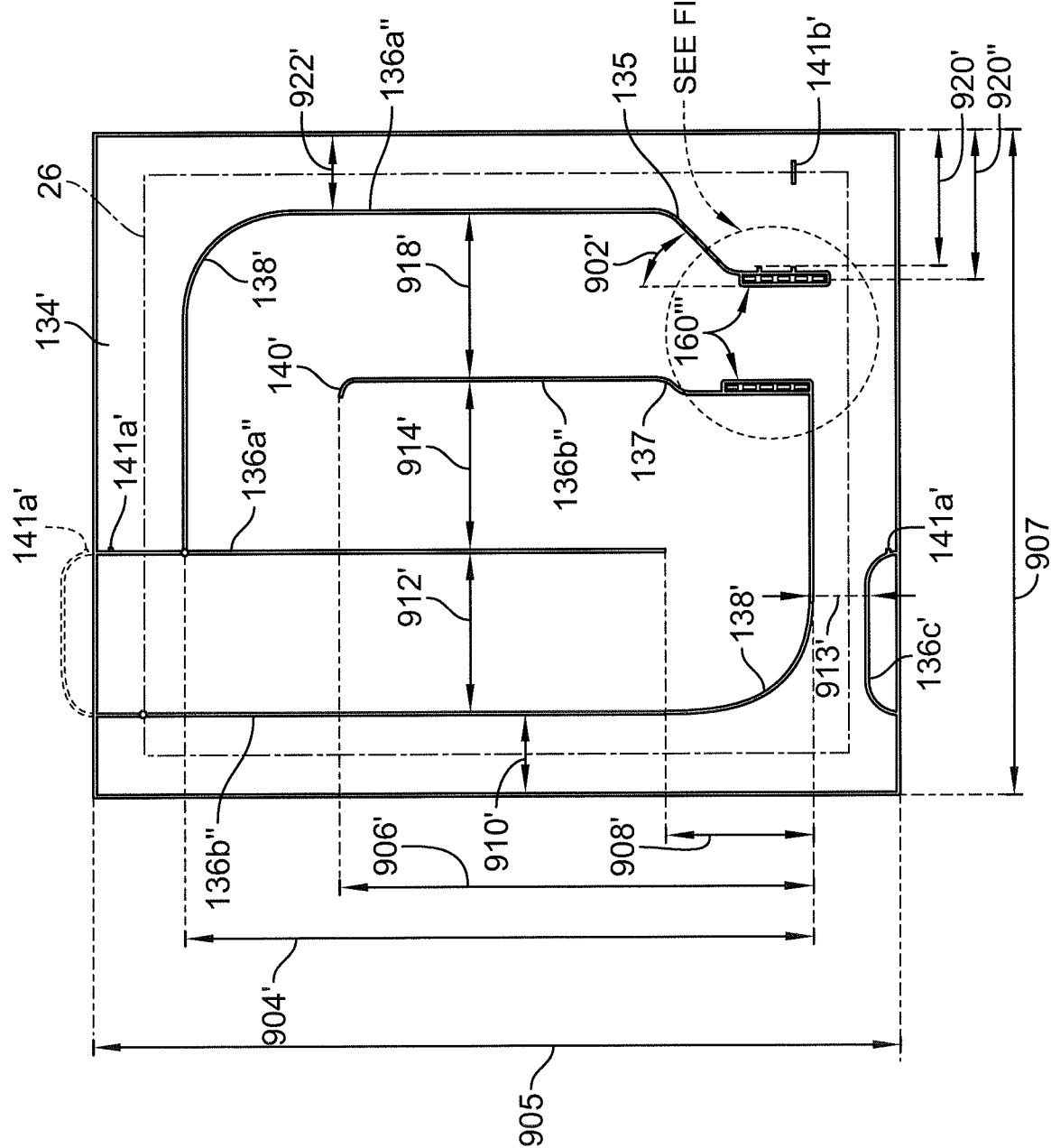
FIG. 25 is a top plan view of another alternative embodiment backsheet showing the geometry of the electrode traces of the alternative embodiment backsheet.

Referring now to FIG. 25, an alternative embodiment backsheet 134' is shown having a different geometry or pattern of first and second electrode traces 136*a"*, 136*b"* as compared to the electrode traces 36*a*, 36*b* of the backsheet 34 shown in FIGS. 1-3 and as compared to the electrode traces 136*a*, 136*b* of the backsheet 134 shown in FIG. 9A. One of the differences is that traces 136*a"*, 136*b"* each include a quarter of a circle trace portion 138' having a radius of about 121.5 mm in the illustrative example. Trace portions 138' are located at diagonally opposite corner regions of backsheet 134'. Trace 136*b"* also includes a hook portion 140' at a terminal end thereof. Segments of electrode traces 136*a"*, 136*b"* other than portions 138', 140' are generally straight, although, electrode trace 136*a"* has an inclined segment 135 leading to redundancy means 160' of trace 136*a"* and electrode trace 136*b"* has an inclined segment 137 spaced above redundancy means 160''' in FIG. 25, with segment 135 being longer that segment 137. Other aspects of the patterns of traces 136*a"*, 136*b"* on backsheet 134' can be readily gleaned from a visual inspection of FIG. 25. Backsheet 134' also has registration marks 141*a'*, 141*b'* that are used during the manufacture of the incontinence detection pad in which backsheet 134' is included.

Still referring to FIG. 25, an overall length 905 of backsheet 134', and therefore the overall length of the associated incontinence detection pad, is about 900 mm and an overall width 907 of backsheet 134', and therefore the overall width of the associated incontinence detection pad, is about 750 mm in the illustrative embodiment. Absorbent core 26 is generally centered on backsheet 134' has as a length of about 790 mm and a width of about 660 mm (see the dotted line rectangle in FIG. 9A which represents the footprint of absorbent core 26). Furthermore, angle 902' is about 45 degrees in the illustrative embodiment.

Additional dimensions of illustrative backsheet 134' include the following: dimension 904' is about 697.0 mm, dimension 906' is about 525.0 mm, dimension 908' is about 163.5 mm, dimension 910' is about 88.5 mm, dimension 912' is about 182.0 mm, dimension 913' between a segment of electrode 136*b"* and a sacrificial trace portion 136*c'* is about 60.5 mm, dimension 914' is about 197.0 mm, dimension 918' is about 182.0 mm, dimension 920' is about 150.0 mm, dimension 920" is about 165 mm, and dimension 922' is about 88.5 mm. It should be appreciated that there is a tolerance range associated with each of the given dimensions. Such tolerance ranges include ranges as high as about +/−4.0 mm and as low as about +/−0.1 mm for the various dimensions and there is also a tolerance range of about +/−0.5 degrees for angle 902'.

The dimensions given for the illustrative example of FIG. 25 are provided for purposes of comparison such as, for example, dimension 914' is about 8.2% larger than dimension 912' or dimension 918'. Also, dimension 914 is more than twice that of dimension 910' or dimension 922'. Many other similar comparisons can be made based on each of the given dimensions associated with pad 134' such that each possible comparison is contemplated herein. In the illustrative example, dimension 904' is generally centered along the overall length 905 of backsheet 134'.

Referring now to FIG. 26, a portion of a film layer 950 is shown carrying six RFID tag circuits 952 which, in turn, include RFID electrical inlays 58' that are substantially the same as inlays 58 shown in FIGS. 5A and 5B, for example. The RFID tag circuits 952 also include the respective RFID integrate circuit (IC) chips that are coupled to each of inlays 58' but that are too small to be discernible in FIG. 26. In some embodiments, inlays 58' of FIG. 26 include gaps that are bridged by resistors 76 according to, for example, any one or more of the variants shown in FIGS. 5B-7D. In FIG. 26, the six RFID tag circuits 952 are arranged in three side-by-side columns with the leftmost column being referred to herein arbitrarily as the first column, the center column being referred to herein arbitrarily as the second column, and the rightmost column being referred to herein arbitrarily as the third column. While only two RFID tag circuits 952 are shown in each of the three illustrative columns, it should be understood that backing sheet 950 continues above and below the depicted circuits 952 of FIG. 26. Backing sheet 950 is flexible, as are inlays 58', and therefore may be supplied as a roll of material having a multitude of circuits 952 thereon arranged in three columns or, in alternative embodiments, more or less than three columns.

Due to the similarities of inlays 58' shown in FIG. 26 with inlays 58 shown, for example, in FIGS. 5A and 5B, the same reference numbers are used to denote like portions of inlays 58, 58'. Thus, inlays 58' each include a pair of large antenna patches 64, a first undulated trace 66 interconnecting patches 64, a first electrical contact pad 68, a second electrical contact pad 70, a second undulated trace 72 extending from contact pad 68 toward contact pad 70, and a third undulated trace 74 extending from contact pad 70 toward contact pad 68. However, unlike inlays 58, inlays 58' include a substantially straight, inclined segment 954 that interconnects the respective electrical contact pads 70 with the associated undulated trace 74. Similar to inlays 58, inlays 58' include a substantially straight segment 955 extending substantially horizontally when inlays 58' are oriented as shown in FIGS.

26 and 27. Segments 955 interconnect the respective electrical contact pad 68 with the associated undulated trace 72.

In the illustrative example, pads 70 on the left side of inlays 58' are offset upwardly with respect to the pads 68 on the right side of inlays 58' (when the inlays 58' are oriented as depicted in FIG. 26). As a result of this inlay geometry, the RFID electrical inlays 58' of adjacent columns are arranged on the backing sheet 950 so that, for example, the right pads 68 of the first column are substantially vertically aligned with the left pads 70 of the second column such that the right and left pads 68, 70 of the first and second columns, respectively, are spaced apart and alternate vertically along a hypothetical line 956 that extends through the right and left pads 68, 70 of the first and second columns. The right and left pads 68, 70 of the inlays 58' of the second and third columns are aligned vertically and alternate in a similar manner.

Still referring to FIG. 26, pads 70 are situated relative to antenna patches 64 such that that the left pad 70 of each RFID electrical inlay 58' is located beside the left antenna patch 64 whereby a hypothetical line 958, which is substantially perpendicular to hypothetical line 956, extends through a center of the left pad 70 and intersects the antenna patches 64 which comprise the antenna of the respective inlay 58'. Furthermore, the right pad 68 of each RFID electrical inlay 58' is located such that a hypothetical line 960, which is also substantially perpendicular to the hypothetical line 956, extends through a center of the right pad 68 and does not intersect the antenna patches 64 of the respective inlay 58'.

During manufacture of the RFID tags having inlays 58' stripes of conductive adhesive 962 are applied to backing sheet 950 over the respective electrical contact pads 68, 70. The stripes of conductive adhesive 962 are about twice as wide as electrical contact pads 68, 70 in the illustrative example FIG. 26. In other embodiments, the width of the stripes of conductive adhesive 962 is less wide or wider, as desired. After the conductive adhesive 962 is applied to backing sheet 950, the backing sheet 950 is cut to separate the columns of inlays 58' from each other. According to this disclosure, a cut pattern or cutline 964 weaves back and forth through each stripe of conductive adhesive 962. In the embodiment of FIG. 26, the cutline 964 is substantially sinusoidal in shape. The sinusoidal cutlines 964 are in phase in the stripes of conductive adhesive 962 such that the peaks of the sinusoidal cutlines 964 are aligned with each other horizontally and the valleys of sinusoidal cutlines 964 are aligned with each other horizontally.

In the stripes of electrically conductive adhesive 962 between the first and second columns, and between the second and third columns, the sinusoidal cutlines 964 weave back and forth between the alternating electrical contact pads 68, 70. The geometry of the sinusoidal cutlines 964 is such that contact pad 68 of each inlay 58' is located adjacent a valley of the adjacent sinusoidal cutline 964 and the associated electrical contact pad 70 of the same inlay 58' is located adjacent a peak of the adjacent sinusoidal cutline 964. By aligning electrical contact pads 68, 70 in between the first and second columns, and in between the second and third columns, and by having a cut pattern 964 that weaves back and forth between the electrical contact pads 68, 70, a savings in the amount of electrically conductive adhesive being used is achieved as compared to other arrangements, such as that shown in FIG. 5A, that do not have any of the electrical contact pads 68, 70 aligned in adjacent columns.

Referring now to FIG. 27, after the columns are separated from each other along the cutlines 964, a set of lateral cuts or cutlines 966 above and below the respective RFID tag circuits 952 are made widthwise to separate the circuits 952 from each other. In the illustrative example, the lateral cuts 966 are straight but other shapes of lateral cutlines 966 may be used in other embodiments. In some embodiments, the three separated columns of RFID tag circuits 952 are each placed on a wider backing sheet or layer 968 after the substantially sinusoidal cuts 964 shown in FIG. 26 have been made. In such embodiments, the lateral cuts 966 extend all the way across the wider backing layer 968 between opposite edges 970 of the layer 968. Thus, although only one column of circuits 952 are shown in FIG. 27 with an optional backing sheet 968, it should be appreciated that all three columns from FIG. 26 are handled similarly after separation from each other.

Although the embodiment of FIGS. 26 and 27 are shown with sinusoidal shaped cutlines 964, the present disclosure contemplates cutlines of other shapes. For example, as shown in FIG. 28, a square wave cutline 964' may be used if desired. A rectangular wave is also considered to be within the scope of the term "square wave" according to this disclosure. Thus, any stepped pattern using right angle cut patterns similar to cutline 964' of FIG. 28 is considered to be a "square wave" cutline herein. As another example of an alternative embodiment, a triangle wave cutline 964" may be used as shown in FIG. 29. Although FIGS. 28 and 29 show the alternative cutlines 964', 964" weaving back and forth within the stripes of electrically conductive adhesive 962 between the aligned, alternating electrical contact pads 68, 70, it should be appreciated that these same shaped cutlines 964', 964", respectively, may be used for the outside stripes of electrically conductive adhesive 962 having only pads 68 or only pads 70, as the case may be.

Referring now to FIG. 30, another alternative is shown in which electrically conductive adhesive 962' is applied to backing sheet 950 intermittently as dashes or patches of adhesive 962' rather than as a continuous stripe of electrically conductive adhesive 962. The intermittent stripe or patches of adhesive 962' are applied over the respective electrical contact pads 68, 70, as the case may be, with gaps or spaces of the backing sheet 950 that lack any adhesive separating the patches of adhesive 962'. A further savings in adhesive material usage is achieved by applying the adhesive 962' intermittently. In some embodiments, the intermittent patches of adhesive 962' are applied to the outermost column edges (e.g., the leftmost edge of the first column and the rightmost edge of the third column) over respective electrical contact pads 68, 70, whereas continuous stripes of electrically conductive adhesive 962 are applied to the two middle stripes of adhesive that are shared between the first and second columns, and between the second and third columns. In other embodiments, all four stripes of adhesive may be applied intermittently as separated patches over the respective electrical contact pads 68, 70.

Figure 31A:
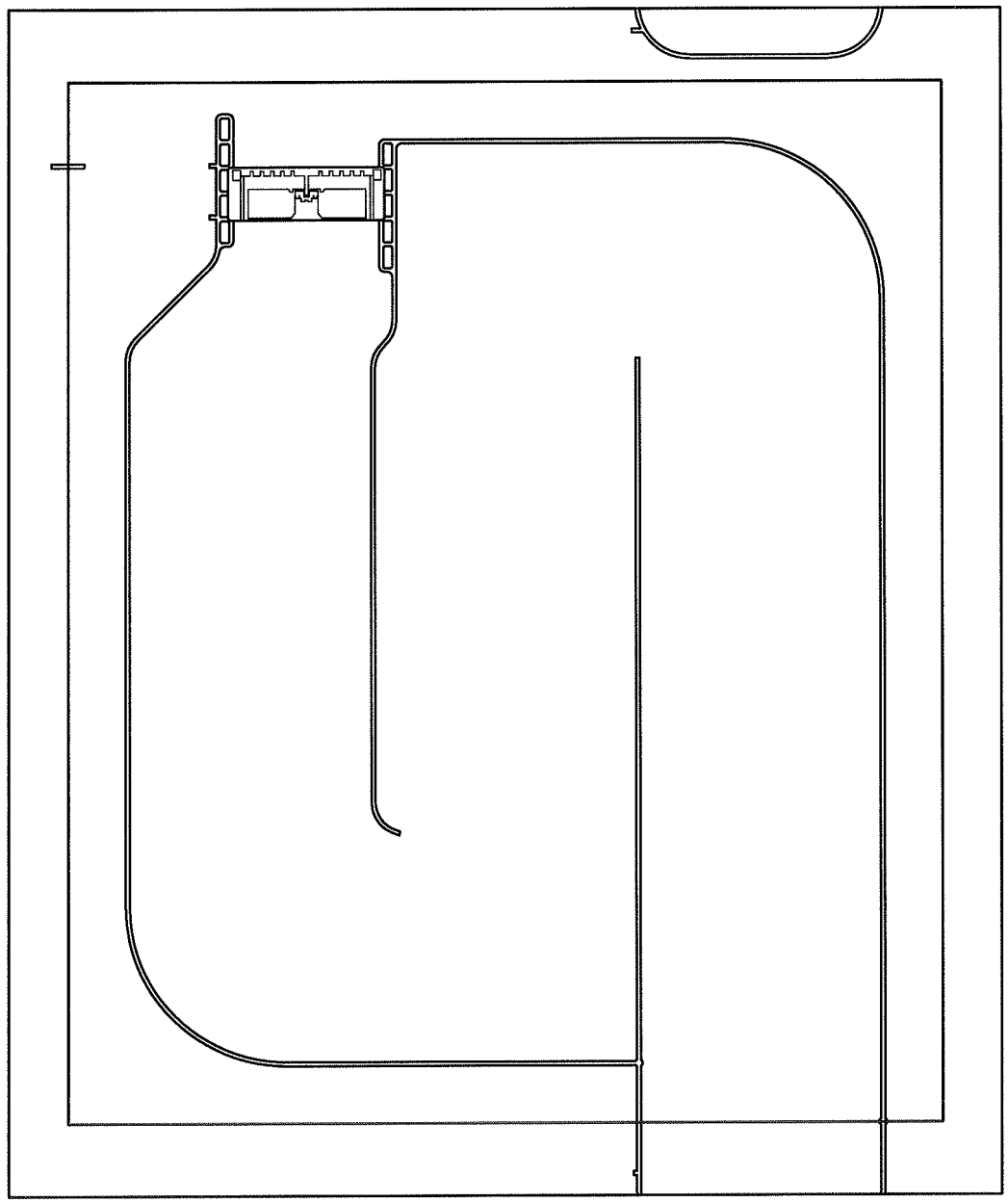
FIG. 31A is a top plan view of an incontinence detection pad, similar to FIG. 25, showing a substantially rectangular outer perimeter of the incontinence detection pad, a smaller substantially rectangular outline of an absorbent core of the incontinence detection pad within the outer perimeter, the outline of the electrode traces, a sacrificial trace at the right hand side of the incontinence detection pad, and the RFID tag attached to ladder-shaped portions of the electrode traces.
Figure 31B:
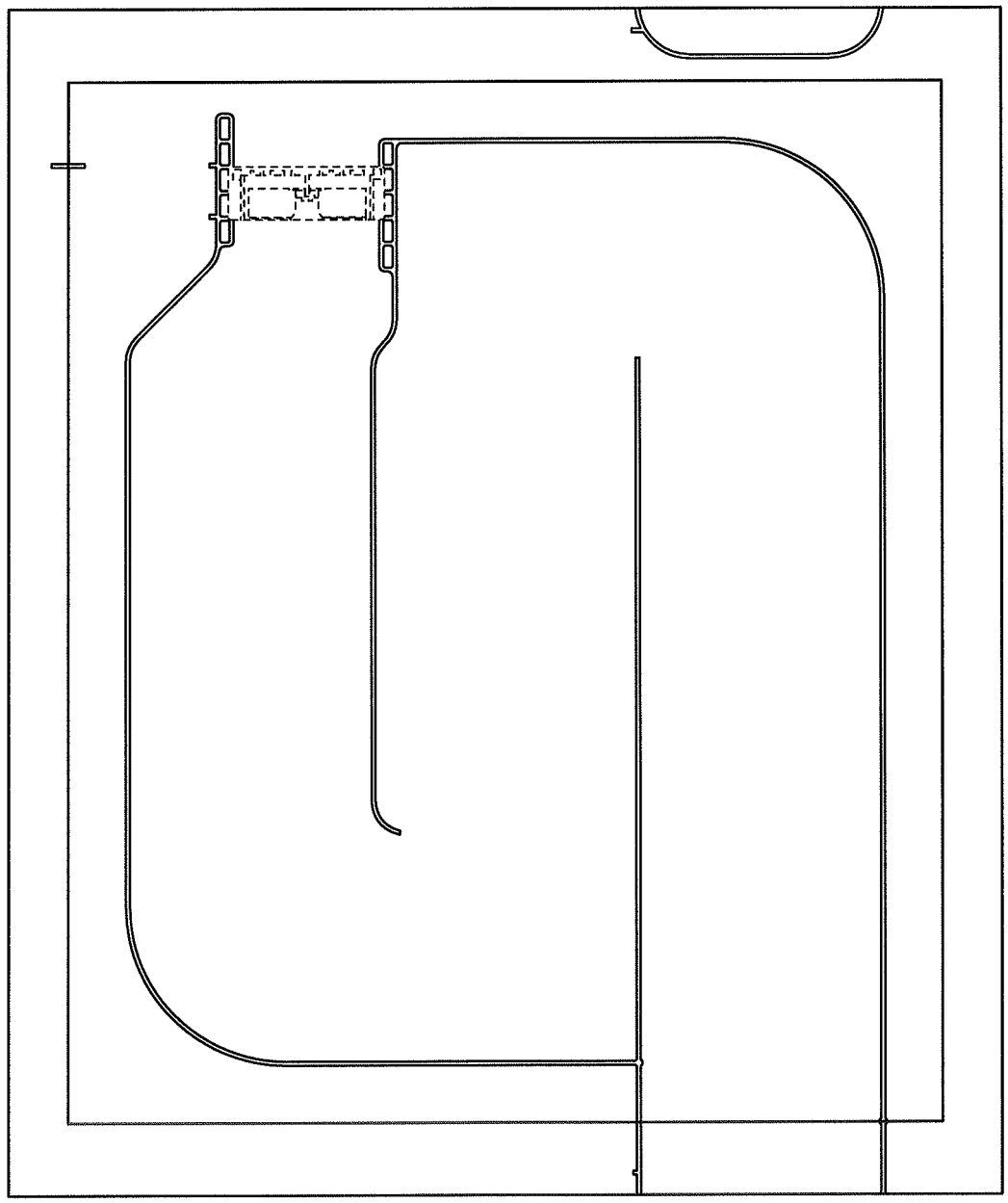
FIG. 31B is a top plan view of the incontinence detection pad, similar to FIG. 31A, showing the RFID tag dotted out.
Figure 31C:
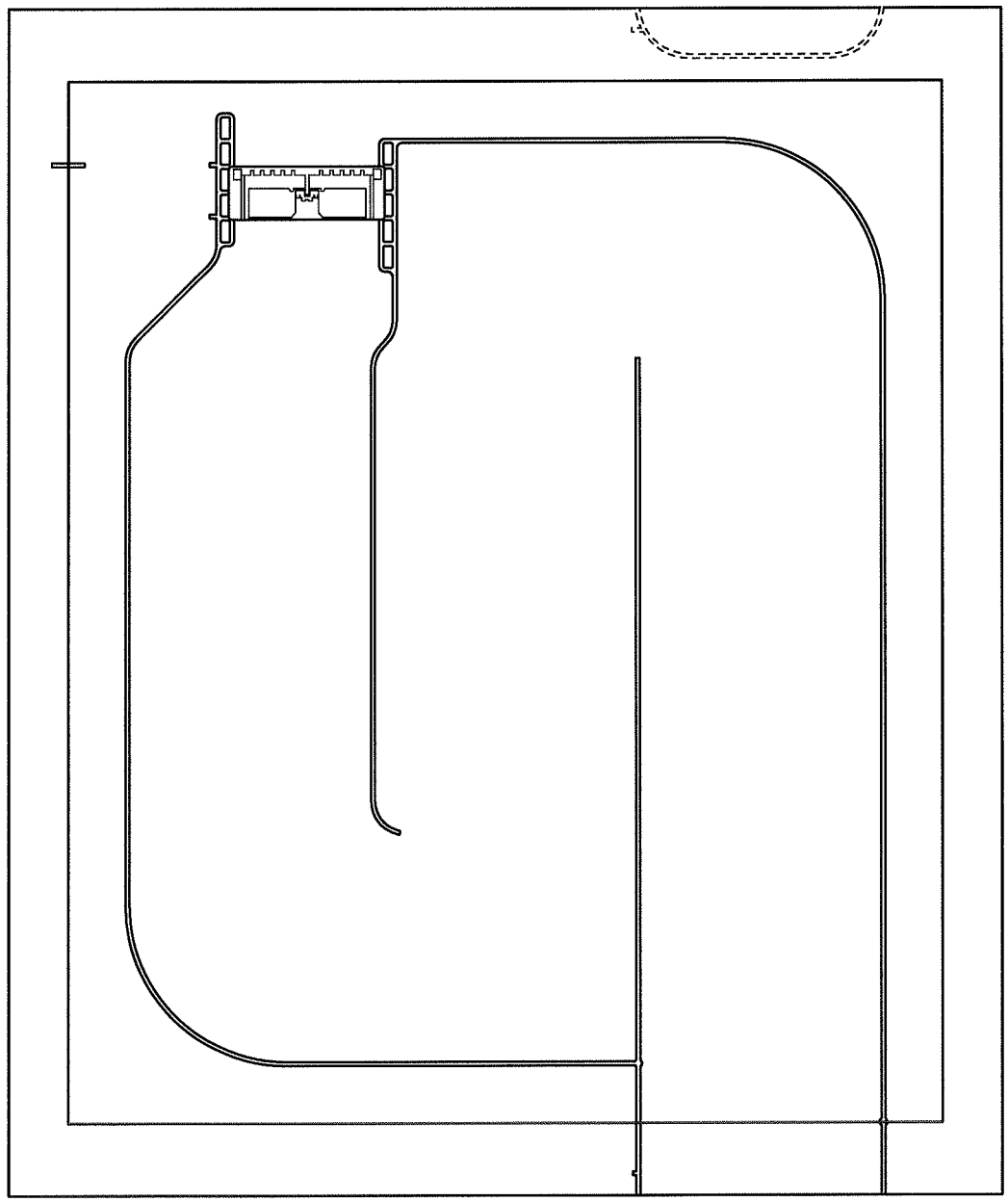
FIG. 31C is a top plan view of the incontinence detection pad, similar to FIG. 31A, showing the sacrificial trace dotted out.
Figure 31D:
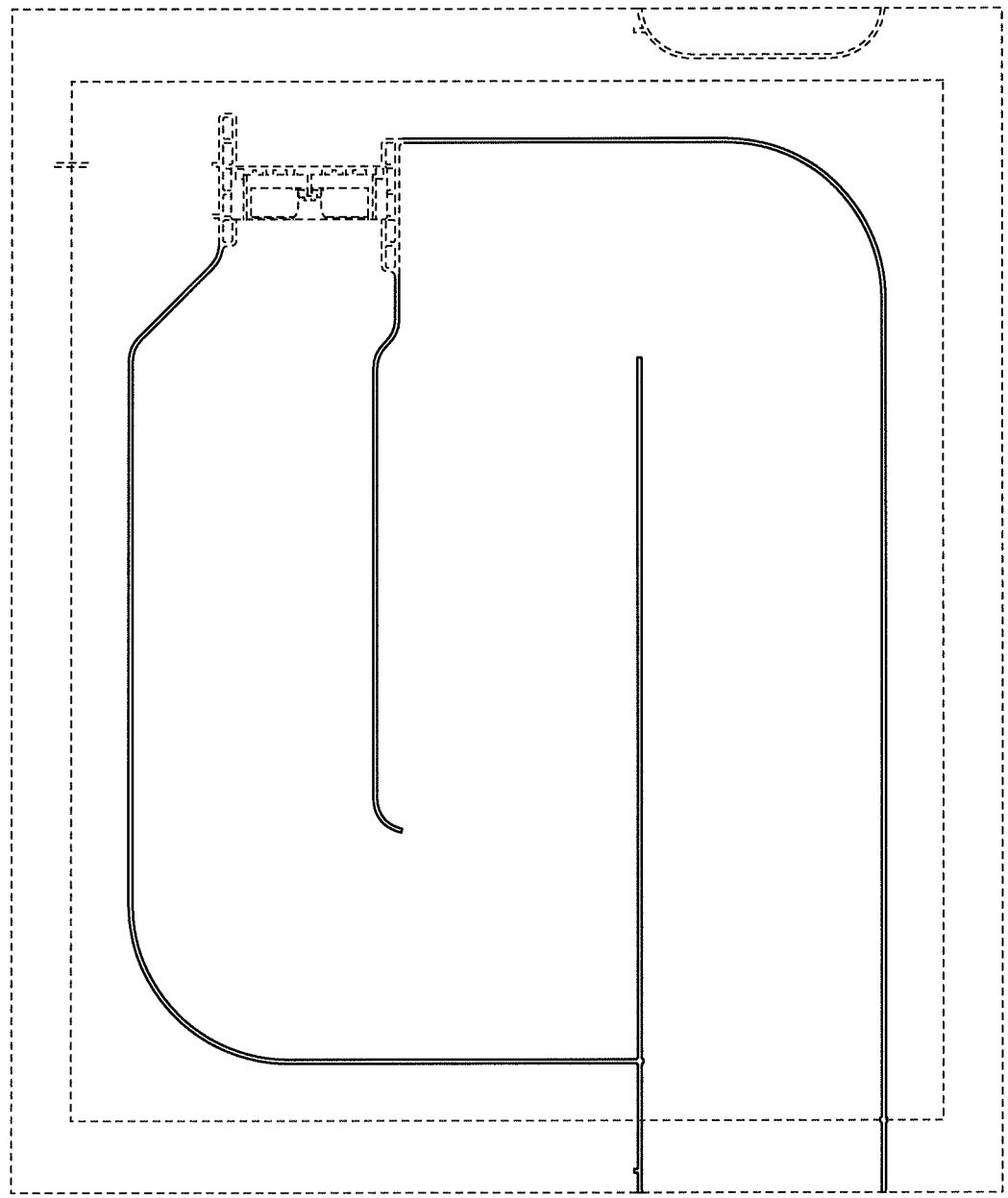
FIG. 31D is a top plan view of the incontinence detection pad, similar to FIG. 31A, showing all portions of the electrode traces, except for the ladder-shaped portions, in solid and everything else dotted out.
Figure 31E:
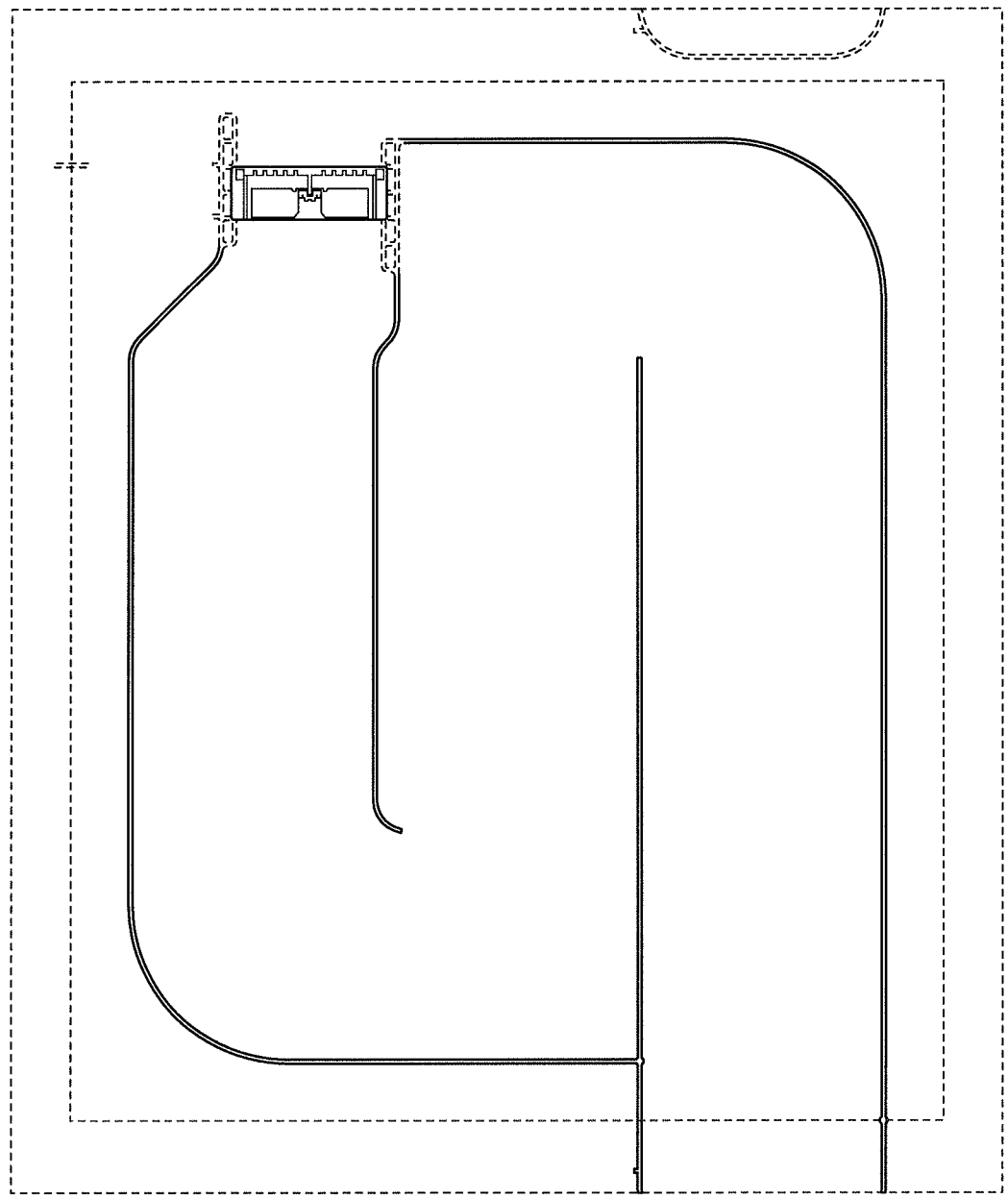
FIG. 31E is a top plan view of the incontinence detection pad, similar to FIG. 31D, but also having the RFID tag in solid.
Figure 31F:
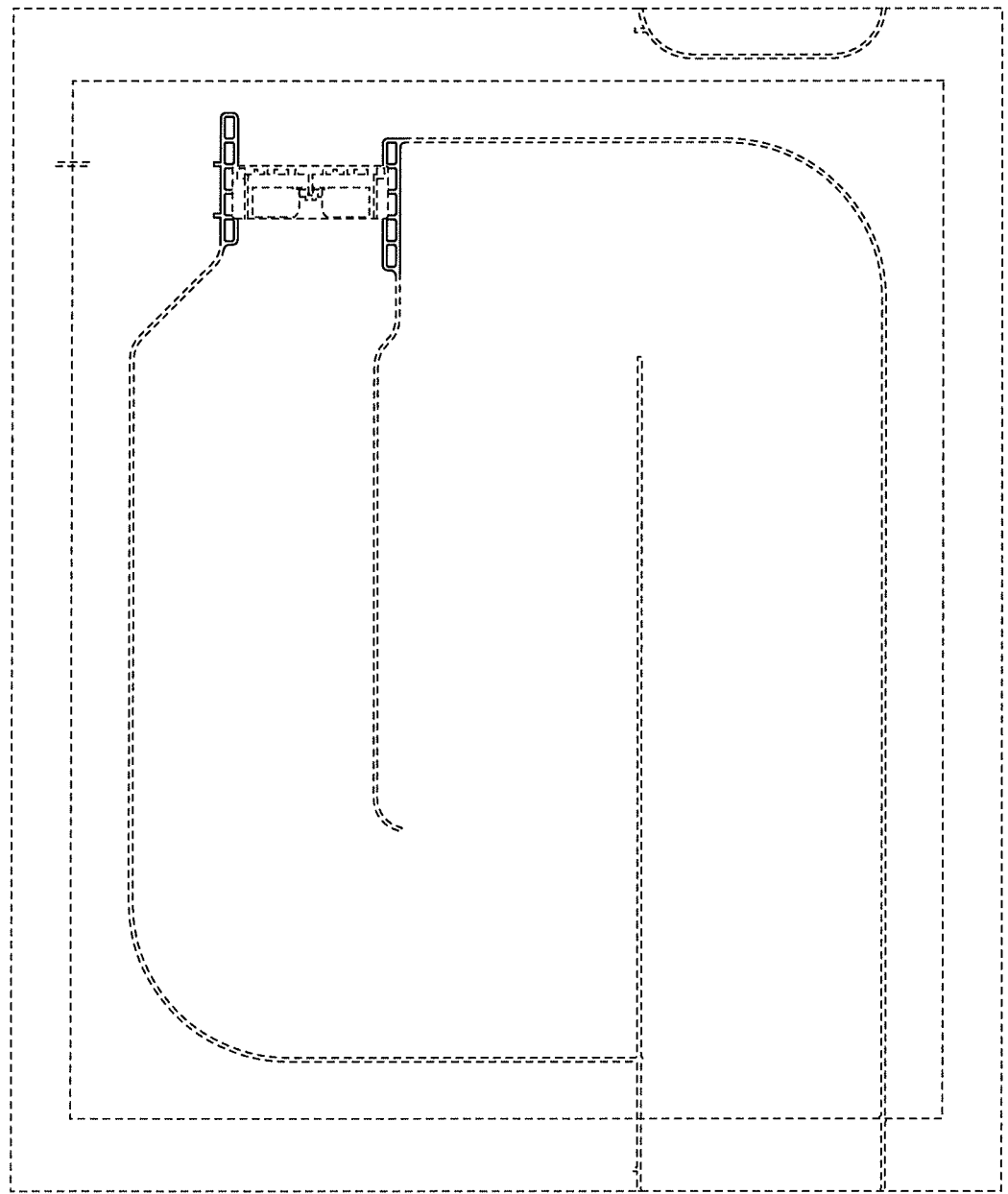
FIG. 31F is a top plan view of the incontinence detection pad, similar to FIG. 31A, showing the ladder-shaped portions of the electrode traces in solid and everything else dotted out.
Figure 31G:
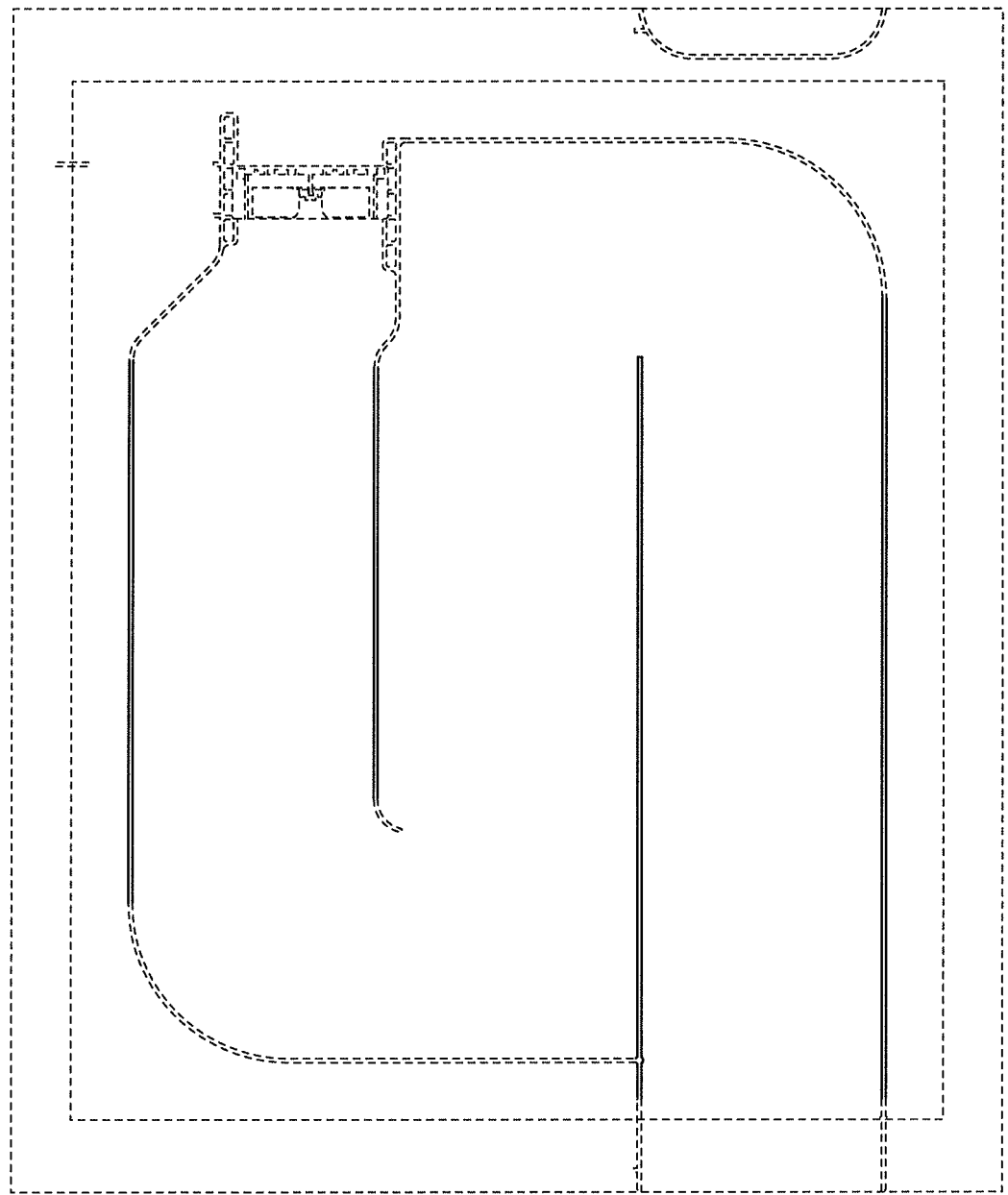
FIG. 31G is a top plan view of the incontinence detection pad, similar to FIG. 31A, showing horizontal portions of the electrode traces in solid and everything else dotted out.
Figure 31H:
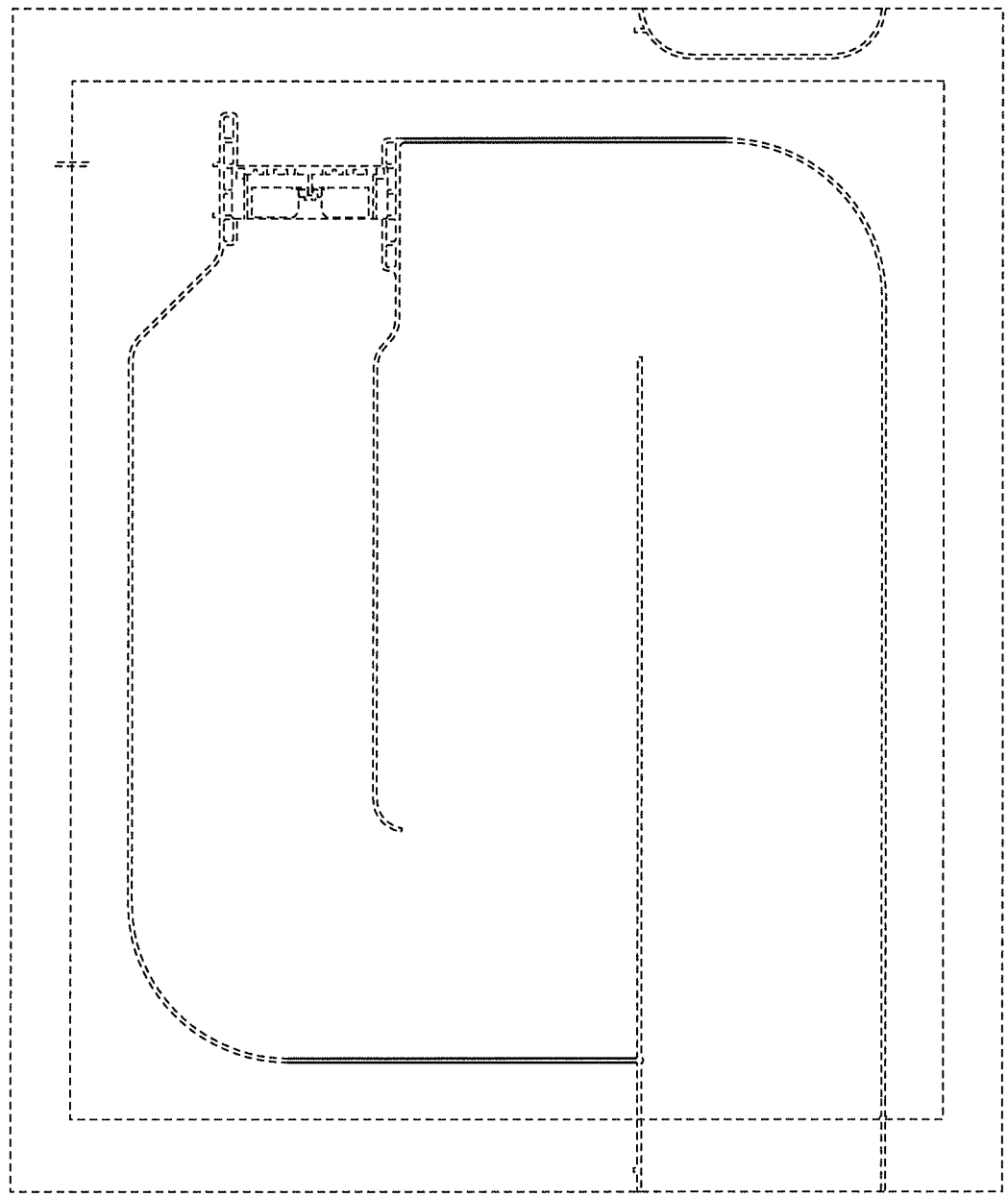
FIG. 31H is a top plan view of the incontinence detection pad, similar to FIG. 31A, showing vertical portions of the electrode traces in solid and everything else dotted out.
Figure 31I:
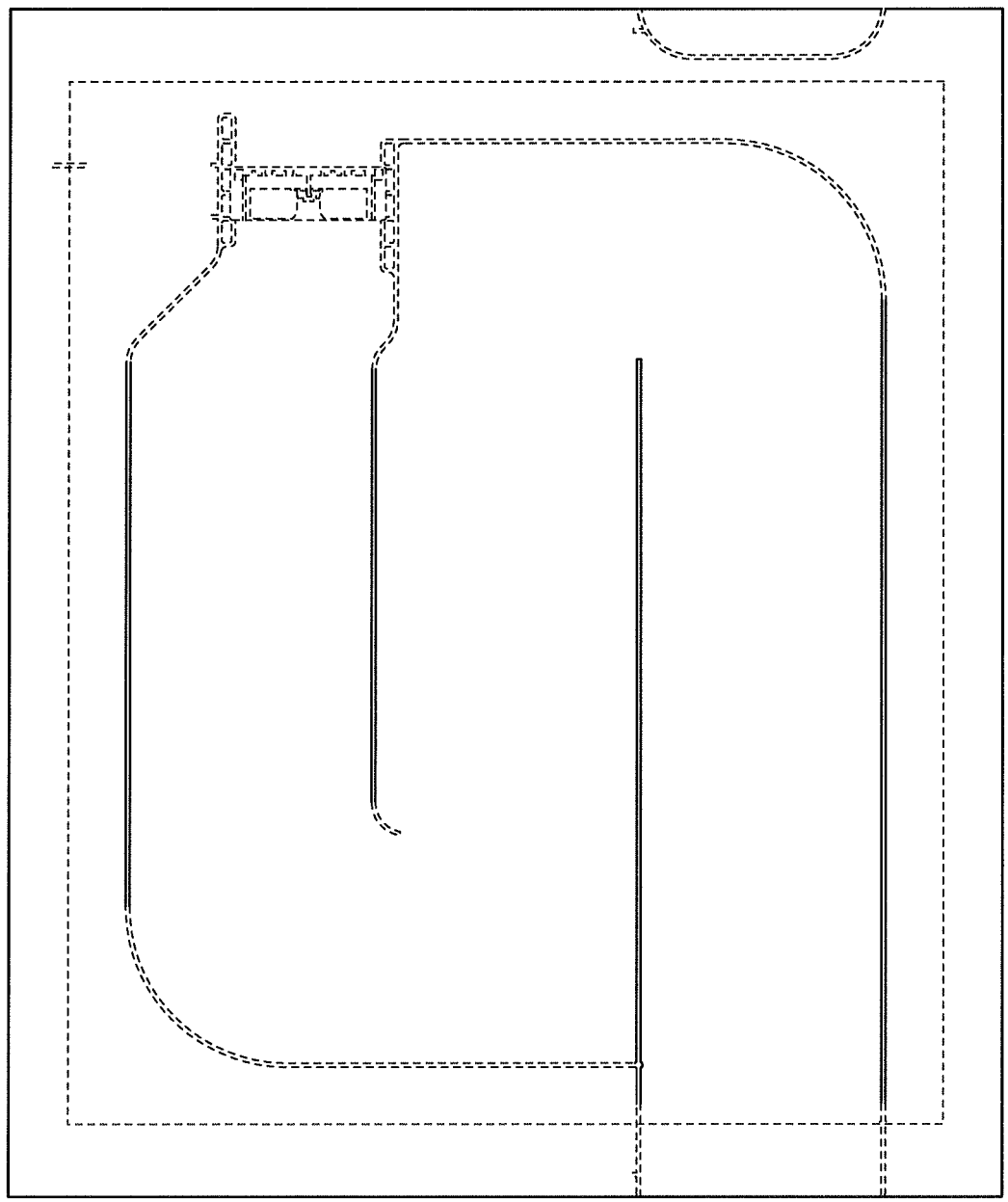
FIG. 31I is a top plan view of the incontinence detection pad, similar to FIG. 31G, but having the substantially rectangular outer perimeter of the incontinence detection pad shown in solid.
Figure 31J:
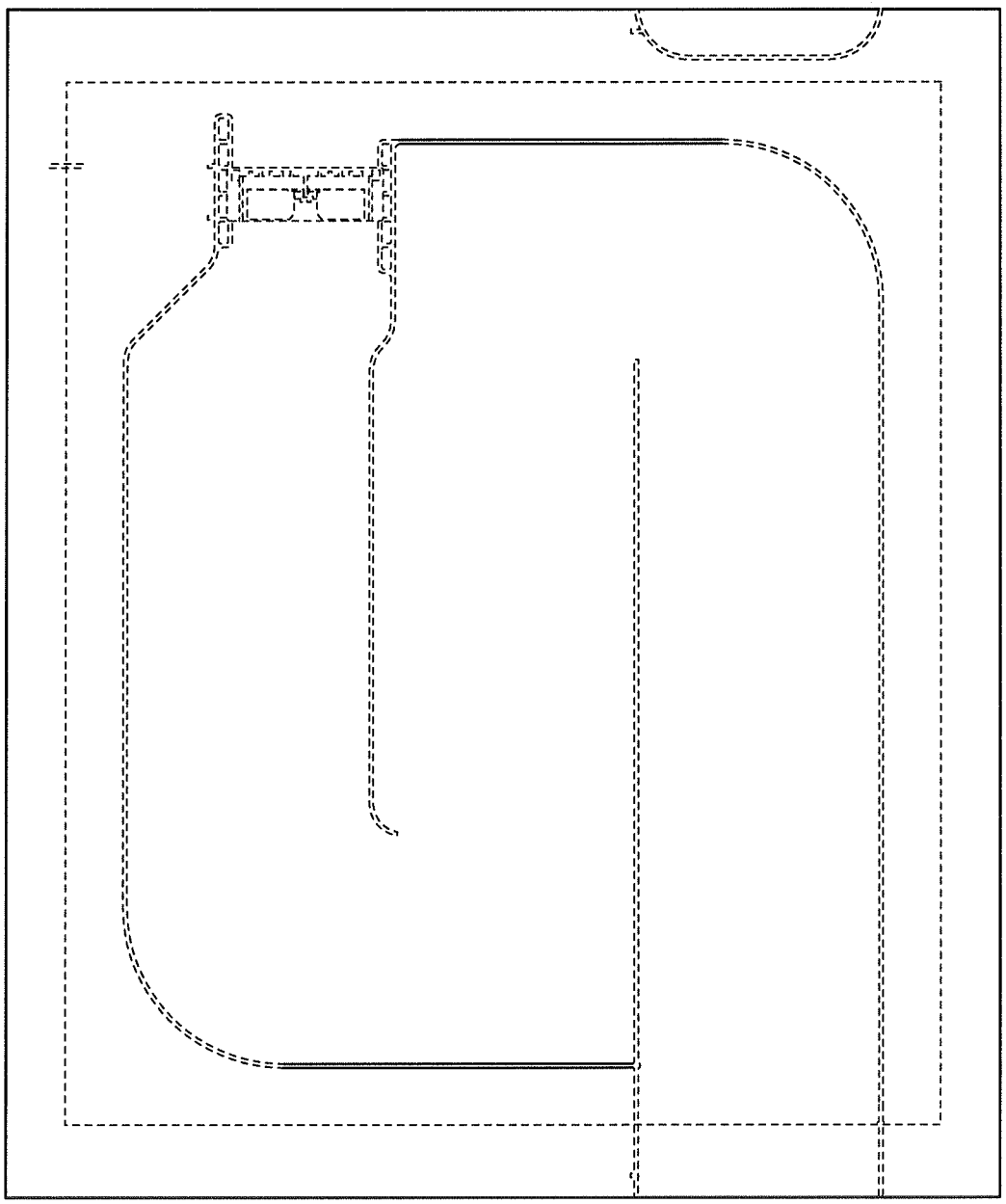
FIG. 31J is a top plan view of the incontinence detection pad, similar to FIG. 31H, but having the substantially rectangular outer perimeter of the incontinence detection pad shown in solid.
Figure 31K:
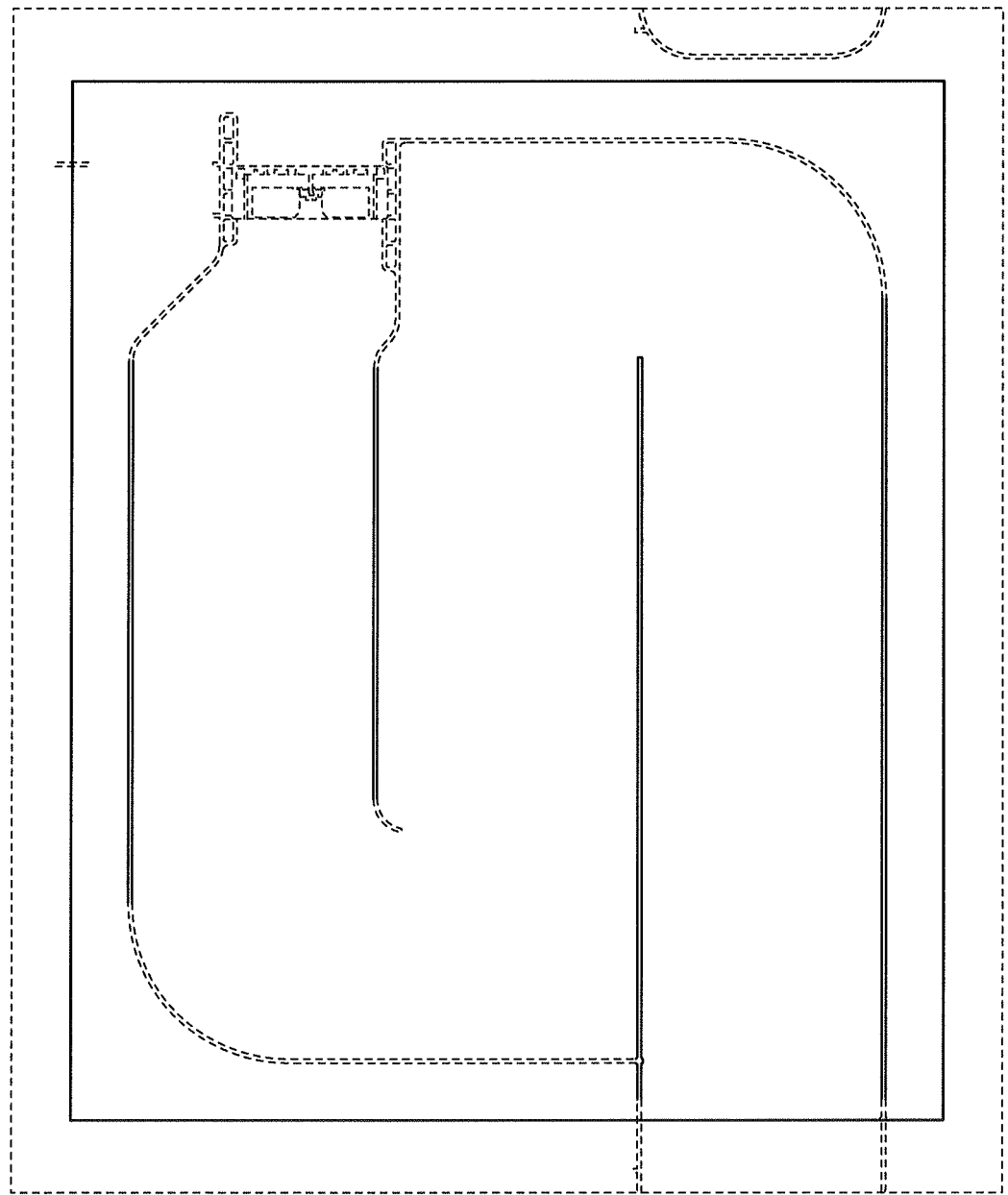
FIG. 31K is a top plan view of the incontinence detection pad, similar to FIG. 31G, but having the smaller substantially rectangular outline of the absorbent core of the incontinence detection pad in solid.
Figure 31L:
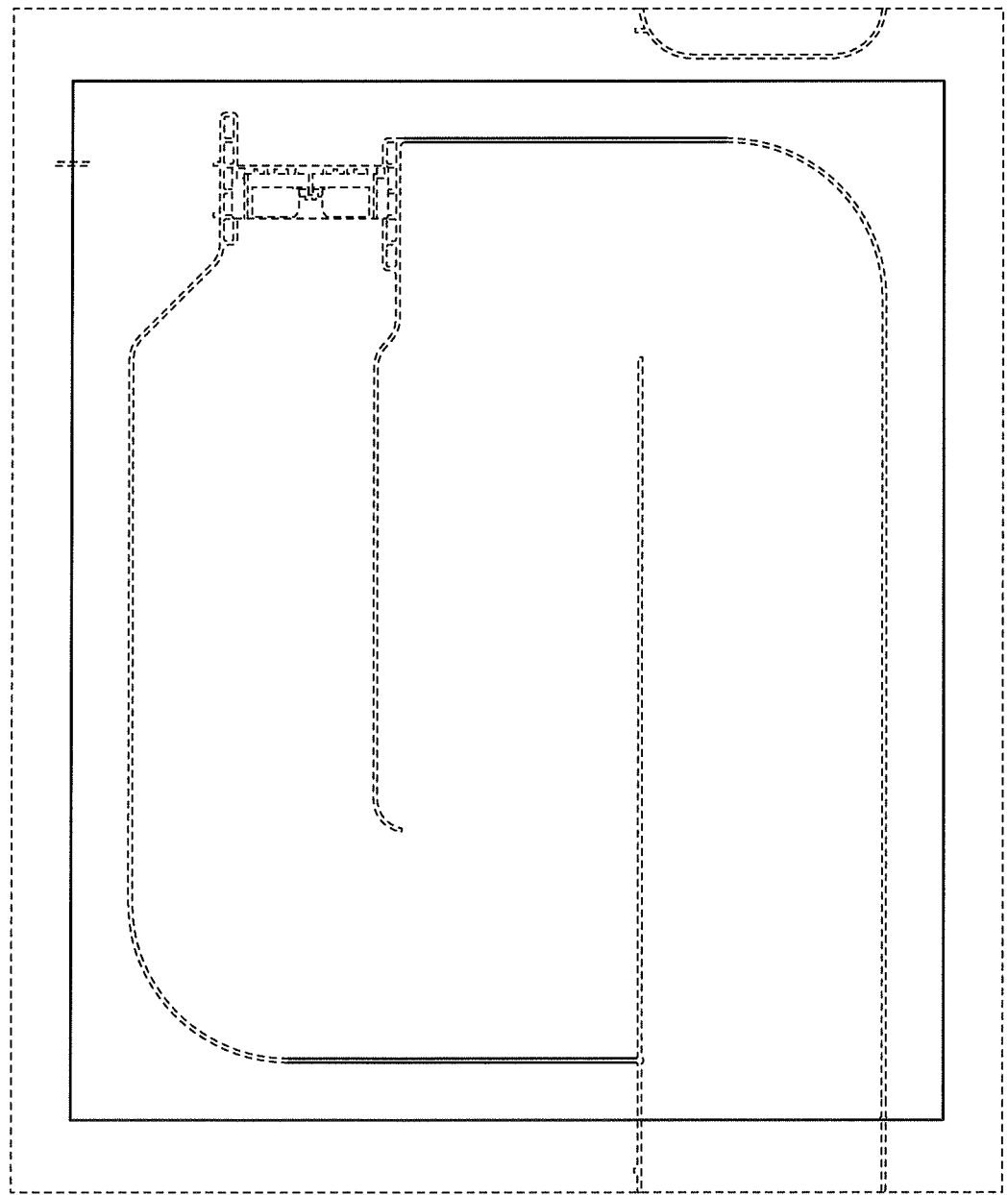
FIG. 31L is a top plan view of the incontinence detection pad, similar to FIG. 31H, but having the smaller substantially rectangular outline of the absorbent core of the incontinence detection pad in solid.
Figure 31M:
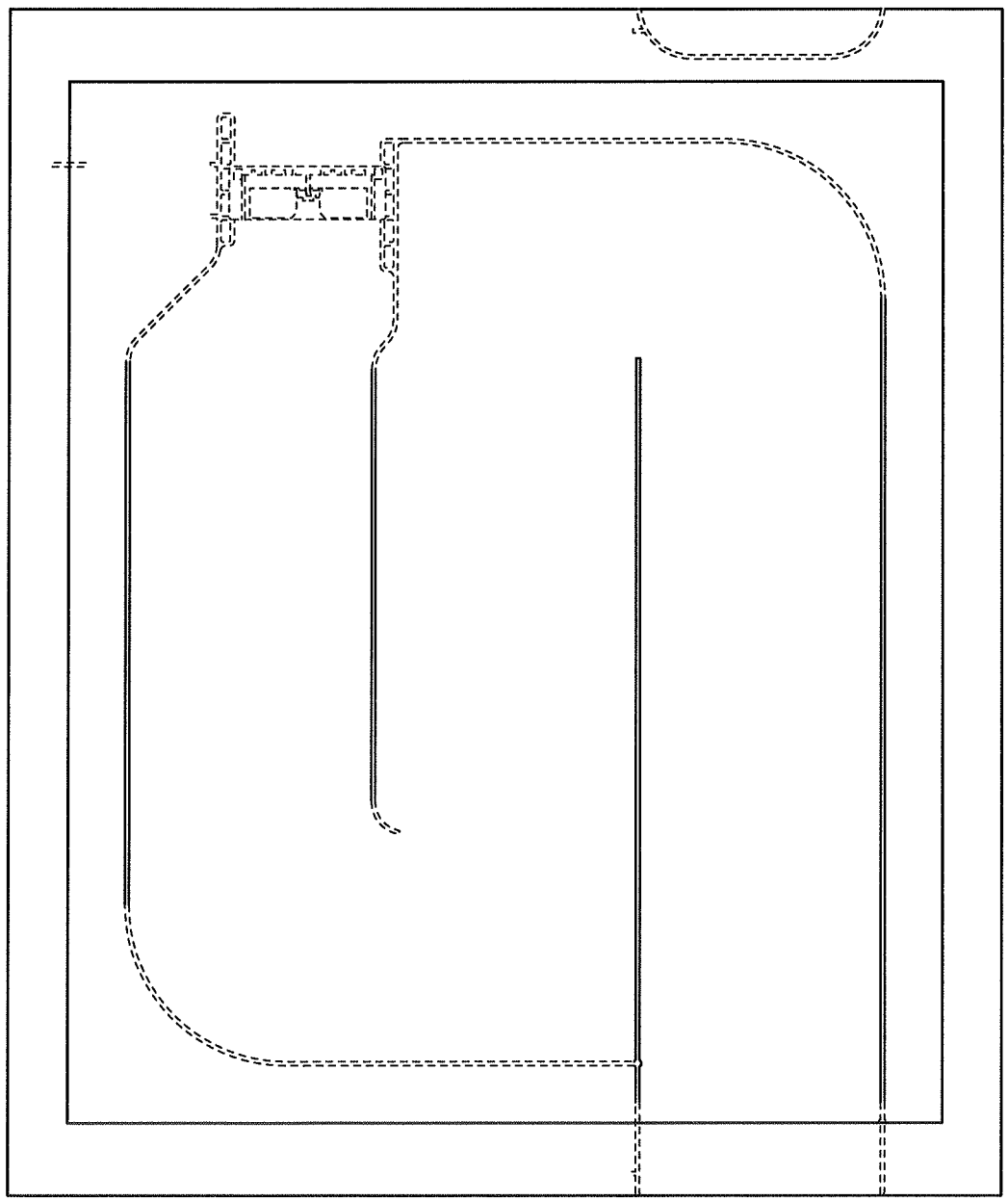
FIG. 31M is a top plan view of the incontinence detection pad, similar to FIG. 31G, but having the substantially rectangular outer perimeter of the incontinence detection pad shown in solid and having the smaller substantially rectangular outline of the absorbent core of the incontinence detection pad in solid.
Figure 31N:
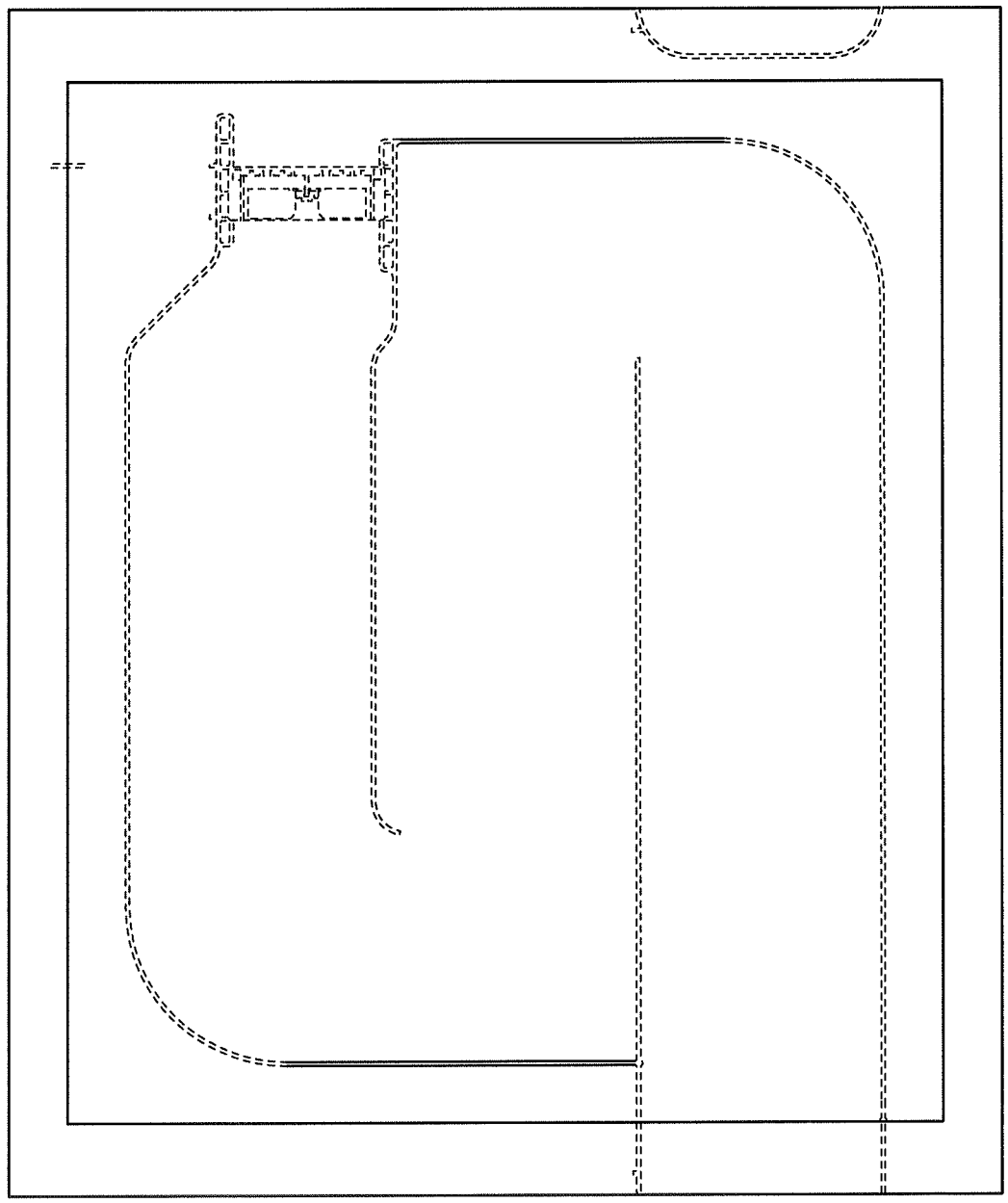
FIG. 31N is a top plan view of the incontinence detection pad, similar to FIG. 31H, but having the substantially rectangular outer perimeter of the incontinence detection pad shown in solid and having the smaller substantially rectangular outline of the absorbent core of the incontinence detection pad in solid.

FIGS. 31A-31N show the ornamental features of an incontinence detection pad according to the present disclosure and may form the basis for future design patent applications claiming priority to the present disclosure. It is contemplated that surface shading may be added, as desired, to any portion of any of FIGS. 31A-31N in such future design patent applications. Furthermore, with regard to such future design patent applications, it is contemplated that any portions of FIGS. 31A-31N that are shown in solid line may be dotted out, as desired, and that any portions of FIGS. 31A-31N that are shown in dotted line may instead be shown in solid line, as desired, such that all combinations and permutations of solid and dotted line depictions of the incontinence detection pad of FIGS. 31A-31N, with or without surface shading being included on any portion thereof, are contemplated by this disclosure.

Although certain illustrative embodiments have been described in detail above, variations and modifications exist within the scope and spirit of this disclosure as described and as defined in the following claims.

The invention claimed is:

1. A method comprising
providing a backing sheet that carries a plurality of RFID electrical inlays, each RFID electrical inlay including at least one antenna portion and a pair of electrical contact portions, each of the pair of electrical contact portions terminating at an electrical contact pad such that one of the electrical contact pads is a right pad and such that another electrical contact pad is a left pad of the respective RFID electrical inlay, wherein some of the RFID electrical inlays are arranged on the backing sheet in adjacent first and second columns having the right pads of the first column substantially aligned with the left pads of the second column such that the right and left pads of the first and second columns, respectively, are spaced apart and alternate along a first hypothetical line extending through the right and left pads of the first and second columns, and
cutting the backing sheet along a cutline that weaves back and forth between the alternating right and left pads of the first and second columns,
wherein some of the RFID electrical inlays are arranged on the backing sheet in a third column that is adjacent the second column with the right pads of the second column substantially aligned with the left pads of the third column such that the right and left pads of the second and third columns, respectively, are spaced apart and alternate along a second, hypothetical line extending through the right and left pads of the second and third columns, and
cutting the backing sheet along a second cutline that weaves back and forth between the alternating right and left pads of the second and third columns.

2. The method of claim 1, wherein after cutting the backing sheet along the cutline, the first column is separated from the second column and further comprising attaching the first column to a second backing sheet that is wider than the first column.

3. The method of claim 1, where the cutline is substantially sinusoidal in shape.

4. The method of claim 1, where the cutline is shaped as a triangle wave or a square wave.

5. The method of claim 1, wherein after cutting the backing sheet along the cutline, the first column is separated from the second column and further comprising cutting the first column widthwise to separate each of the RFID electrical inlays of the first column from one another.

6. The method of claim 5, further comprising cutting the second column widthwise to separate each of the RFID electrical inlays of the second column from one another.

7. The method of claim 1, further comprising, prior to cutting the backing sheet along the cutline, applying electrically conductive adhesive over the right and left pads of the RFID electrical inlays of the first and second columns.

8. The method of claim 7, wherein applying the electrically conductive adhesive over the right and left pads of the RFID electrical inlays of the first and second columns comprises applying the electrically conductive adhesive as a substantially continuous stripe over the right and left pads of the RFID electrical inlays of the first and second columns.

9. The method of claim 1, wherein after cutting the backing sheet along the second cutline, the third column is separated from the second column and further comprising attaching the third column to a second backing sheet that is wider than the third column.

10. The method of claim 1, wherein the second cutline is substantially sinusoidal in shape.

11. The method of claim 1, wherein the second cutline is shaped as a triangle wave or a square wave.

12. The method of claim 1, wherein after cutting the backing sheet along the second cutline, the third column is separated from the second column and further comprising cutting the third column widthwise to separate each of the RFID electrical inlays of the third column from one another.

13. The method of claim 12, further comprising cutting the second column widthwise to separate each of the RFID electrical inlays of the second column from one another.

14. The method of claim 1, further comprising, prior to cutting the backing sheet along the second cutline, applying electrically conductive adhesive over the right and left pads of the RFID electrical inlays of the second and third columns.

15. The method of claim 14, wherein applying the electrically conductive adhesive over the right and left pads of the RFID electrical inlays of the second and third columns comprises applying the electrically conductive adhesive as a substantially continuous stripe over the right and left pads of the RFID electrical inlays of the second and third columns.

16. The method of claim 1, wherein at least one electrical contact portion of each of the pair of electrical contact portions of each RFID electrical inlay includes a gap formed therein to subdivide the at least one electrical contact portion into a first lead segment and a second lead segment, and further comprising a first resistor placed across the gap to electrically interconnect the first and second lead segments.

17. The method of claim 1, wherein both of the electrical contact portions of the pair of electrical contact portions of each RFID electrical inlay includes a gap formed therein to thereby provide a pair of gaps which subdivide the respective electrical contact portions into a first lead segment and a second lead segment, and further comprising first and second resistors placed across the pair of gaps of the pair of electrical contact portions of each RFID electrical inlay to electrically interconnect the respective first and second lead segments.

18. A method comprising
providing a backing sheet that carries a plurality of RFID electrical inlays, each RFID electrical inlay including at least one antenna portion and a pair of electrical contact portions, each of the pair of electrical contact portions terminating at an electrical contact pad such that one of the electrical contact pads is a right pad and such that another electrical contact pad is a left pad of the respective RFID electrical inlay, wherein some of the RFID electrical inlays are arranged on the backing sheet in adjacent first and second columns having the right pads of the first column substantially aligned with the left pads of the second column such that the right and left pads of the first and second columns, respectively, are spaced apart and alternate along a first hypothetical line extending through the right and left pads of the first and second columns,
cutting the backing sheet along a cutline that weaves back and forth between the alternating right and left pads of the first and second columns, and
assembling each RFID electrical inlay of the plurality of RFID electrical inlays into a respective RFID tag of a plurality of RFID tags, and attaching each RFID tag of the plurality of RFID tags to a respective absorbent article having first and second electrode traces with redundancy means that electrically couple to corresponding pairs of the electrical connect pads of the associated RFID electrical inlay.

19. The method of claim 18, wherein each respective absorbent article includes a plurality of high wick bridges interconnecting the first and second electrode traces.

20. The method of claim 18, wherein each respective absorbent article includes a topsheet made of a fluid permeable material, an absorbent core situated beneath the topsheet, and a substrate situated beneath the absorbent core, the first and second electrode traces being formed on the substrate, and wherein each respective absorbent article further comprises a fluid filter layer situated so as to inhibit a low volume of fluid from being able to reach the first and second electrode traces.

\* \* \* \* \*